US011286252B2

(12) United States Patent
Feng et al.

(10) Patent No.: US 11,286,252 B2
(45) Date of Patent: Mar. 29, 2022

(54) ALKENE SPIROCYCLIC COMPOUNDS AS FARNESOID X RECEPTOR MODULATORS

(71) Applicant: BRISTOL-MYERS SQUIBB COMPANY, Princeton, NJ (US)

(72) Inventors: Jianxin Feng, Bensalem, PA (US); Chunjian Liu, Pennington, NJ (US); Yanting Huang, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 85 days.

(21) Appl. No.: 16/760,810

(22) PCT Filed: Oct. 31, 2018

(86) PCT No.: PCT/US2018/058313
§ 371 (c)(1),
(2) Date: Apr. 30, 2020

(87) PCT Pub. No.: WO2019/089665
PCT Pub. Date: May 9, 2019

(65) Prior Publication Data
US 2021/0179599 A1    Jun. 17, 2021

Related U.S. Application Data

(60) Provisional application No. 62/580,073, filed on Nov. 1, 2017.

(51) Int. Cl.
C07D 413/14    (2006.01)
C07D 261/08    (2006.01)
C07D 413/04    (2006.01)
C07D 413/12    (2006.01)
C07D 417/14    (2006.01)
C07D 471/04    (2006.01)
C07D 513/04    (2006.01)

(52) U.S. Cl.
CPC ......... C07D 413/14 (2013.01); C07D 261/08 (2013.01); C07D 413/04 (2013.01); C07D 413/12 (2013.01); C07D 417/14 (2013.01); C07D 471/04 (2013.01); C07D 513/04 (2013.01)

(58) Field of Classification Search
CPC .. C07D 413/14; C07D 471/14; C07D 471/04; C07D 413/12; C07D 513/04; C07D 413/04; C07D 261/08
USPC .................................................. 514/210.16
See application file for complete search history.

(56) References Cited

U.S. PATENT DOCUMENTS 8,158,665 B2    4/2012  Caldwell et al.
8,907,095 B2    12/2014 Xia et al.
9,539,244 B2    1/2017  Kinzel et al.
9,751,874 B2    9/2017  Gege et al.
10,562,910 B2 * 2/2020  Wang ................. C07D 491/044
2003/0130296 A1  7/2003  Bauer et al.
2004/0048316 A1  3/2004  Haffner et al.
2006/0258725 A1  11/2006 Boggs et al.
2008/0096921 A1  4/2008  Navas, III et al.
2008/0167356 A1  7/2008  Caldwell et al.
2008/0306125 A1  12/2008 Bell et al.
2009/0093524 A1  4/2009  Bell et al.
2009/0270460 A1  10/2009 Bell et al.
2010/0035918 A1  2/2010  Guckian et al.
2010/0152166 A1  6/2010  Genin et al.
2010/0184809 A1  7/2010  Kremoser et al.
2010/0210660 A1  8/2010  Kremoser et al.
2010/0249179 A1  9/2010  Deaton et al.

(Continued)

FOREIGN PATENT DOCUMENTS

CN    106146483 A    11/2016
CN    106632294 A    5/2017

(Continued)

OTHER PUBLICATIONS

Claudel, Thierry et al., "The Farnesoid X Receptor: A Novel Drug Target?", Expert Opin. Investig. Drugs, vol. 13(9), pp. 1135-1148, (2004).

(Continued)

Primary Examiner — Kahsay Habte
(74) Attorney, Agent, or Firm — Gary Greenblatt

(57) ABSTRACT

The present invention provides compounds of Formula (I), or stereoisomers, tautomers, or pharmaceutically acceptable salts or solvates thereof, wherein all the variables are as defined herein. These compounds modulate the activity of farnesoid X receptor (FXR), for example, as agonists. This invention also relates to pharmaceutical compositions comprising these compounds and methods of treating a disease, disorder, or condition associated with FXR dysregulation, such as pathological fibrosis, transplant rejection, cancer, osteoporosis, and inflammatory disorders, by using the compounds and pharmaceutical compositions.

(I)

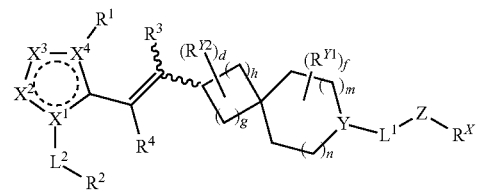

13 Claims, No Drawings

(56) References Cited

U.S. PATENT DOCUMENTS

| | | |
|---|---|---|
| 2011/0034507 A1 | 2/2011 | Akwabi-Ameyaw et al. |
| 2011/0092512 A1 | 4/2011 | Ackermann et al. |
| 2011/0230493 A1 | 9/2011 | Long et al. |
| 2012/0232116 A1 | 9/2012 | Kremoser et al. |
| 2013/0261108 A1 | 10/2013 | Tully et al. |
| 2013/0331349 A1 | 12/2013 | Tully et al. |
| 2014/0039007 A1 | 2/2014 | Tully et al. |
| 2014/0221659 A1 | 8/2014 | Kinzel et al. |
| 2015/0218187 A1 | 8/2015 | Koul et al. |
| 2015/0366856 A1 | 12/2015 | Tully et al. |
| 2016/0176861 A1 | 6/2016 | Gege et al. |
| 2017/0298068 A1 | 10/2017 | Gege et al. |
| 2017/0304270 A1 | 10/2017 | Or et al. |
| 2017/0304271 A1 | 10/2017 | Or et al. |
| 2017/0304272 A1 | 10/2017 | Or et al. |
| 2017/0333399 A1 | 11/2017 | Or et al. |
| 2017/0355693 A1 | 12/2017 | Blomgren et al. |
| 2017/0355694 A1 | 12/2017 | Gege |
| 2017/0368038 A1 | 12/2017 | Badman et al. |
| 2019/0002452 A1 | 1/2019 | Zhang et al. |

FOREIGN PATENT DOCUMENTS

| | | |
|---|---|---|
| CN | 107021958 A | 8/2017 |
| EP | 3034499 A1 | 6/2016 |
| EP | 3034501 A1 | 6/2016 |
| EP | 3401315 A1 | 11/2018 |
| WO | 199313101 A1 | 7/1993 |
| WO | 199817276 A1 | 4/1998 |
| WO | 2006006490 A1 | 1/2006 |
| WO | 2007076260 A2 | 7/2007 |
| WO | 2008051942 A2 | 5/2008 |
| WO | 2008094556 A2 | 8/2008 |
| WO | 2009009059 A1 | 1/2009 |
| WO | 2009149795 A2 | 12/2009 |
| WO | 2010058318 A1 | 5/2010 |
| WO | 2011006935 A2 | 1/2011 |
| WO | 2011045292 A1 | 4/2011 |
| WO | 2012087520 A1 | 6/2012 |
| WO | 2013007387 A1 | 1/2013 |
| WO | 2013186159 A1 | 12/2013 |
| WO | 2014054053 A1 | 4/2014 |
| WO | 2015172747 A1 | 11/2015 |
| WO | 2016096115 A1 | 6/2016 |
| WO | 2017049173 A1 | 3/2017 |
| WO | 2017133521 A1 | 8/2017 |
| WO | 2017145040 A1 | 8/2017 |
| WO | 2017145041 A1 | 8/2017 |
| WO | 2018059314 A1 | 4/2018 |
| WO | 2018170165 A1 | 9/2018 |
| WO | 2018170166 A1 | 9/2018 |
| WO | 2018170167 A1 | 9/2018 |
| WO | 2018170173 A1 | 9/2018 |
| WO | 2018170182 A1 | 9/2018 |

OTHER PUBLICATIONS

Crawley, Matthew Lantz, "Farnesoid X receptor modulators: a patent review," Expert Opinion on Therapeutic Patents, (2010) 20:8, pp. 1047-1057.

International Preliminary Report on Patentability No. PCT/US2018/058313, dated May 5, 2020.

International Search Report for PCT/US2018/058313, filed Oct. 31, 2018.

Sepe, Valentina et al., "Farnesoid X Receptor Modulators 2014-present: A Patent Review", Expert Opinion on Therapeutic Patents, vol. 28, No. 5, pp. 351-364 (2018).

Tully, David C. et al., "Discovery of Tropifexor (LJN452), a Highly Potent Non-bile Acid FXR Agonist for the Treatment of Cholestatic Liver Diseases and Nonalcoholic Steatohepatitis (NASH)", Journal of Medicinal Chemistry, vol. 60, pp. 9960-9973 (2017).

* cited by examiner

ALKENE SPIROCYCLIC COMPOUNDS AS FARNESOID X RECEPTOR MODULATORS

CROSS REFERENCE

This application is a 371 application of International Application No. PCT/US2018/058313 filed on Oct. 31, 2018, which claims the benefit of U.S. Provisional Application Ser. No. 62/580,073, filed Nov. 1, 2017, the content of each is hereby fully incorporated by reference in its entirety for all purposes.

The present invention relates generally to compounds useful as farnesoid X receptor (FXR) modulators, pharmaceutical compositions comprising such compounds and to their use in therapy, especially in the treatment or prophylaxis of diseases, disorders, and conditions for which an FXR modulator is indicated.

FXR or NR1H4 (nuclear receptor subfamily 1, group H, member 4) is a nuclear receptor that can activate the expression of specific target genes in a ligand-dependent manner. FXR is expressed in the liver, throughout the gastrointestinal tract, colon, ovary, adrenal gland, kidney, and in the gall bladder and biliary tree in humans. FXR forms a heterodimer with Retinoid X Receptor (RXR) and binds to specific response elements in target genes to regulate gene transcription (B. M. Forman et al., Cell 1995; 81: 687; W. Seol et al., Mol. Endocrinol. 1995; 9: 72). The FXR/RXR heterodimer typically binds to an inverted repeat of a consensus hexanucleotide sequence (AGGTCA) separated by a single nucleotide, i.e. an IR-1 sequence. The relevant physiological ligands of FXR are bile acids including chenodeoxycholic acid and its taurine-conjugate (D. J. Parks et al., Science 1999; 284: 1365; M. Makishima et al., Science 1999; 284: 1362). FXR activation regulates the expression of multiple genes that encode enzymes and transporters involved in bile acid synthesis, influx, and efflux from the liver and intestine resulting in a net decrease in total endogenous bile acids in a negative feedback loop. FXR is involved in paracrine and endocrine signaling by upregulating the expression of the cytokine Fibroblast Growth Factor 15 (rodents) or 19 (primates), which can also contribute to the regulation of bile acid concentrations (Holt et al., Genes Dev. 2003; 17: 1581; Inagaki et al., Cell Metab 2005; 2: 217). Therefore, FXR is considered to be a master regulator of bile acid homeostasis.

One use of FXR agonists is for the treatment of diseases in which bile acids are dysregulated, including cholestatic diseases (e.g. primary biliary cirrhosis and primary sclerosing cholangitis) that can lead to fibrosis, cirrhosis, cholangiocarcinoma, hepatocellular carcinoma, liver failure, and death. While elevated bile acid concentrations in the liver have deleterious effects, bile acids also affect the microflora and integrity of the small intestine. Obstruction of bile flow in humans or rodents causes proliferation of intestinal bacteria and mucosal injury, which can lead to bacterial translocation across the mucosal barrier and systemic infection (Berg, Trends Microbiol. 1995; 3: 149-154). Mice lacking FXR have increased ideal levels of bacteria and a compromised epithelial barrier, while activation of intestinal FXR plays an important role in preventing bacterial overgrowth and maintaining the integrity of the intestinal epithelium (Inagaki et al., Proc Natl Acad Sci 2006; 103: 3920-3925). Over time, FXR null mice spontaneously develop hepatocellular carcinoma, and this can be abrogated by selective re-activation of FXR in the intestine (Degirolamo et al., Hepatology 61: 161-170). Pharmacological activation of FXR with a small molecule agonist or transgenic expression of FXR in the intestine can normalize bile acid concentrations, decrease cellular proliferation in hepatic bile ducts, and reduce inflammatory cell infiltration, necrotic area, and liver fibrosis in rodent models of cholestasis (Liu et al., J. Clin. Invest. 2003; 112:1678-1687; Modica et al., Gastroenterology. 2012; 142: 355-365). Some of these beneficial effects observed in preclinical models of cholestasis have translated to human patients, and the FXR agonist, obeticholic acid (OCA or OCALIVA™), has been approved for the treatment of primary biliary cirrhosis (https://www.fda.gov/newsevents/newsroom/pressannouncements/ucm503964.htm).

In addition to controlling bile acid homeostasis, FXR agonists regulate the hepatic expression of hundreds of genes encoding proteins involved in cholesterol and lipid metabolism and transport, glucose homeostasis, inflammation, chemotaxis, and apoptosis among other pathways (Zhan et al., PLoS One 2014; 9: e105930; Ijssennagger et al., J Hepatol 2016; 64: 1158-1166). Consistent with these broad effects on gene expression, FXR agonists have also been investigated in preclinical models of fibrosis, cancer, inflammatory diseases, and metabolic disorders, including dyslipidemia, obesity, type 2 diabetes, nonalcoholic fatty liver disease (NAFLD) and metabolic syndrome (Crawley, Expert Opin. Ther. Patents 2010; 20:1047-1057).

FXR agonists are also being investigated in human clinical trials for the treatment of NAFLD, a more advanced form of fatty liver disease, nonalcoholic steatohepatitis (NASH), and associated complications. NAFLD is one of the most common causes of chronic liver disease in the world today (Vernon et al., Aliment Pharmacol Ther 2011; 34:274-285). The risk factors for developing NAFLD include obesity, type 2 diabetes mellitus (T2DM), insulin resistance, hypertension, and dyslipidemia. In a 6-week clinical trial in T2DM patients with NAFLD, the FXR agonist OCA statistically significantly improved insulin sensitivity and reduced body weight, showing beneficial effects on some of these risk factors (Mudaliar et al., Gastroenterology 2013; 145: 574-582). NASH is the most severe and progressive form of NAFLD and includes the histological findings of hepatic steatosis, inflammation, and ballooning degeneration with varying amounts of pericellular fibrosis (Sanyal et al., Hepatology 2015; 61:1392-1405). In a 72-week clinical trial in patients with NASH, OCA statistically significantly improved hepatic steatosis, lobular inflammation, hepatocyte ballooning, and fibrosis as assessed by histological analyses of liver biopsies (Neuschwander-Tetri et al., Lancet 2015; 385: 956-965). These data also suggest the potential for FXR agonists to show benefit on clinical outcomes given that NASH is the second leading cause of hepatocellular carcinoma (HCC) and liver transplantation in the United States (Wong et al., Hepatology 2014; 59: 2188-2195).

The present invention provides novel compounds for treating a disease, disorder, or condition associated with farnesoid X receptor (FXR) activity in a patient in need thereof.

SUMMARY OF THE INVENTION

In one aspect, the present invention provides compounds of Formula (I) and (II) as well as the subgenera and species thereof, including stereoisomers, tautomers, pharmaceutically acceptable salts, and solvates thereof, which are useful as FXR modulators.

In another aspect, the present invention also provides processes and intermediates for making the compounds of the present invention.

In another aspect, the present invention also provides pharmaceutical compositions comprising a pharmaceutically acceptable carrier and at least one of the compounds of the present invention or stereoisomers, tautomers, pharmaceutically acceptable salts, or solvates thereof.

In another aspect, the compounds of the invention may be used in therapy, either alone or in combination with one or more additional therapeutic agents.

The compounds of the invention may be used in the treatment of a disease, disorder, or condition associated with activity of farnesoid X receptor (FXR) in a patient in need of such treatment by administering a therapeutically effective amount of the compound, or a stereoisomer, a tautomer, or a pharmaceutically acceptable salt or solvate thereof, to the patient. The disease, disorder, or condition may be related to pathological fibrosis. The compounds of the invention can be used alone, in combination with one or more compounds of the present invention, or in combination with one or more, e.g., one to two, other therapeutic agents.

The compounds of the invention may be used, either as a single agent or in combination with other agents, in the treatment of a disease, disorder, or condition selected from nonalcoholic steatohepatitis (NASH), non-alcoholic fatty liver disease (NAFLD), chronic kidney disease, diabetic kidney disease, primary sclerosing cholangitis (PSC), and primary biliary cirrhosis (PBC). The compounds of the invention may be used, either as a single agent or in combination with other agents, in the treatment of idiopathic pulmonary fibrosis (IPF).

The compounds of the invention may be used for the manufacture of a medicament for the treatment of a disease, disorder, or condition in a patient in need of such treatment.

Other features and advantages of the invention will be apparent from the following detailed description and claims.

DETAILED DESCRIPTION

The present application provides compounds, including all stereoisomers, solvates, prodrugs and pharmaceutically acceptable salt and solvate forms thereof, according to Formula (I). The present application also provides pharmaceutical compositions containing at least one compound according to Formula (I), or a stereoisomer, a tautomer, or a pharmaceutically acceptable salt or a solvate thereof, and optionally at least one additional therapeutic agent. Additionally, the present application provides methods for treating a patient suffering from a FXR-modulated disease or disorder such as for example, biliary fibrosis, liver fibrosis, renal fibrosis, Non-Alcoholic Fatty Liver Disease (NAFLD), Non-Alcoholic Steato-Hepatitis (NASH), primary sclerosing cholangitis (PSC), primary biliary cirrhosis (PBC), and pancreatic fibrosis, by administering to a patient in need of such treatment a therapeutically effective amount of a compound of the present invention, or a stereoisomer, a tautomer, or a pharmaceutically acceptable salt or a solvate thereof, and optionally in combination with at least one additional therapeutic agent.

I. Compounds of the Invention

In one embodiment, the present invention provides a compound of Formula (I):

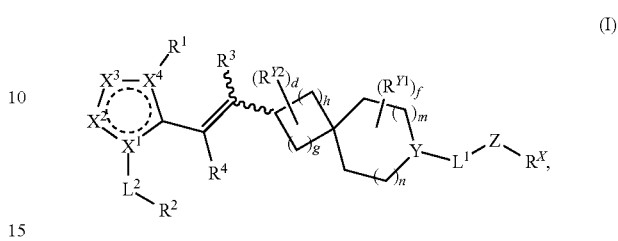

or a stereoisomer, a tautomer, or a pharmaceutically acceptable salt or solvate thereof; wherein $X^1$ and $X^4$ are each independently C or N;

$X^2$ and $X^3$ are each independently $CR^5$, N, $NR^6$, O, or S;

Y is $CR^7$, or N:

m and n are each independently an integer of 0, 1, or 2;

h and g are each independently an integer of 1 or 2;

d and f are each independently an integer of 0, 1, 2, or 3;

Z is 6- to 10-membered aryl, 5- to 10-membered heteroaryl, 3- to 10-membered carbocyclyl, or 4- to 10-membered heterocyclyl, wherein the aryl, heteroaryl carbocyclyl, and heterocyclyl are independently substituted with 0 to 5 $R^8$;

$L^1$ is a covalent bond, O, S, $NR^{17}$, $-S(O)_2-$, $C_{1-3}$ alkylene, $C_{1-3}$ heteroalkylene, $C_{2-4}$ alkenylene, $C_{2-4}$ alkynylene, aryl, or a 5- to 6-membered heteroaryl containing 1 to 4 heteroatoms independently selected from N, O, and S; wherein the alkylene, heteroalkylene, aryl, and heteroaryl are each independently substituted with 0 to 3 $R^{11}$;

$L^2$ is a covalent bond, O, S, $NR^{18}$, $C_{1-3}$ alkylene, or $C_{1-3}$ heteroalkylene, wherein the alkylene and heteroalkylene are independently substituted with 0 to 3 $R^{16}$;

$R^X$ is $-L^3-R^Z$;

$L^3$ is a covalent bond, a $C_{1-3}$ alkylene, or $-C(O)NR^{12}-CH_2-$, wherein the $C_{1-3}$ alkylene is substituted with 0 to 3 $R^{15}$;

$R^Z$ is $-CN$, $-C(O)OR^{13}$, $-C(O)NR^{14a}R^{14b}$,

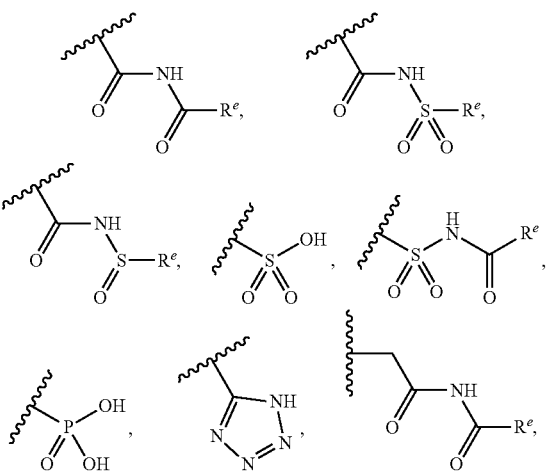

-continued

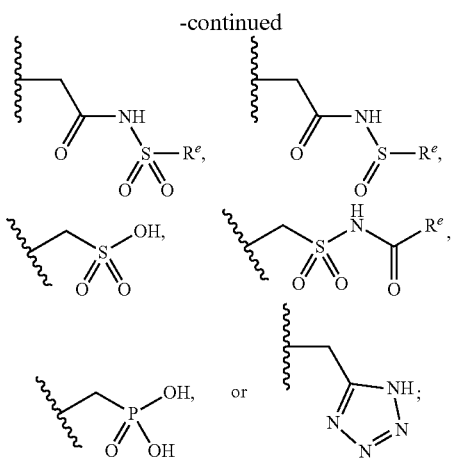

$R^e$ is $C_{1-6}$ alkyl, $C_{3-6}$ cycloalkyl, haloalkyl, hydroxyalkyl, aminoalkyl, alkoxyalkyl, or haloalkoxyalkyl;

$R^{Y1}$ and $R^{Y2}$ are each independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy; or alternatively two $R^{Y1}$, together with the carbon atoms to which they are attached, form a bridge moiety; and with the proviso that when Y is N and $R^{Y1}$ is attached to a carbon atom adjacent to Y, then $R^{Y1}$ is not halo, cyano, hydroxyl, amino, alkoxy, or haloalkoxy;

$R^1$ is $C_{1-6}$ alkyl, $C_{3-5}$ cycloalkyl, or $C_{4-6}$ heterocyclyl, wherein the alkyl and cycloalkyl are independently substituted with 0 to 3 $R^9$;

$R^2$ is 6- to 10-membered aryl, 5- to 10-membered heteroaryl, 3- to 10-membered carbocyclyl, or 4- to 10-membered heterocyclyl, wherein the aryl, heteroaryl, carbocyclyl, and heterocyclyl are independently substituted with 0 to 5 $R^{10}$;

$R^3$ and $R^4$ are each independently hydrogen, $C_{1-6}$ alkyl, haloalkyl, hydroxyalkyl, aminoalkyl, alkoxyalkyl, or haloalkoxyalkyl;

$R^5$ and $R^7$ are each independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy;

$R^6$, $R^{17}$ and $R^{18}$ are each independently hydrogen, $C_{1-6}$ alkyl, haloalkyl, hydroxyalkyl, aminoalkyl, alkoxyalkyl, haloalkoxyalkyl, alkoxy, or haloalkoxy;

$R^8$ and $R^{10}$ are each independently halo, cyano, hydroxyl, amino, oxo, —$OR^a$, —$SR^a$, =S, —$NR^cR^c$, =NH, =N—OH, =$NR^a$, =N—$OR^a$, —$NO_2$, —$S(O)_2R^a$, —$S(O)_2NHR^b$, —$S(O)_2NR^cR^c$, —$S(O)_2OR^b$, —$OS(O)_2R^b$, —$OS(O)_2OR^b$, —$P(O)(OR^b)(OR^b)$, —$C(O)R^b$, —$C(NR^b)R^b$, —$C(O)OR^b$, —$C(O)NR^cR^c$, —$C(NR^b)NR^cR^c$, —$OC(O)R^b$, —$NR^bC(O)R^b$, —$OC(O)OR^b$, —$NR^bC(O)OR^b$, —$OC(O)NR^cR^c$, —$NR^bC(O)NR^cR^c$, —$NR^bC(NR^b)R^b$, —$NR^bC(NR^b)NR^cR^c$, $C_{1-6}$ alkyl, $C_{1-6}$ haloalkyl, aryl, arylalkyl, heteroaryl, carbocyclyl, or heterocyclyl; wherein the alkyl, aryl, heteroaryl, carbocyclyl, and heterocyclyl, by themselves or as part of another group, are each independently substituted with 0 to 5 $R^d$.

$R^a$ is each independently $C_{1-6}$ alkyl, haloalkyl, hydroxyalkyl, aminoalkyl, alkoxyalkyl, haloalkoxyalkyl, aryl, arylalkyl, heteroaryl, heteroarylalkyl, carbocyclyl, carbocyclylalkyl, heterocyclyl, or heterocyclylalkyl;

$R^b$ is each independently hydrogen or $R^a$;

$R^c$ is each independently $R^b$ or alternatively, the two $R^c$ are taken together with the nitrogen atom to which they are bonded form a 4-, 5-, 6- or 7-membered heterocyclyl;

$R^d$ is each independently $R^a$, alkoxy, haloalkoxy, alkylamino, cycloalkylamino, heterocyclylamino, haloalkyl, hydroxyalkyl, aminoalkyl, cycloalkoxy, heterocyclyloxy, haloalkoxy, alkoxyalkoxy, haloalkylamino, alkoxyalkylamino, haloalkoxyalkylamino, arylamino, aralkylamino, aryloxy, aralkyloxy, heteroaryloxy, heteroarylalkyloxy, alkylthio, halo, cyano, hydroxyl, amino, oxo, —$OR^a$, —$SR^a$, =S, —$NR^cR^c$, =NH, =N—OH, =$NR^a$, =N—$OR^a$, —$NO_2$, —$S(O)_2R^a$, —$S(O)_2NHR^b$, —$S(O)_2NR^cR^c$, —$S(O)_2OR^b$, —$OS(O)_2R^b$, —$OS(O)_2OR^b$, —$P(O)(OR^b)(OR^b)$, —$C(O)R^b$, —$C(NR^b)R^b$, —$C(O)OR^b$, —$C(O)NR^cR^c$, —$C(NR^b)NR^cR^c$, —$OC(O)R^b$, —$NR^bC(O)R^b$, —$OC(O)OR^b$, —$NR^bC(O)OR^b$, —$NR^bC(O)NR^cR^c$, —$NR^bC(NR^b)R^b$, or —$NR^bC(NR^b)NR^cR^c$;

$R^9$ is each independently halo, cyano, hydroxyl, amino, or $C_{1-6}$ alkyl;

$R^{11}$ and $R^{16}$ are each independently halo, oxo, cyano, hydroxyl, amino, $C_{1-6}$ alkyl, $C_{3-6}$ cycloalkyl, $C_{4-6}$ heterocyclyl, alkylamino, haloalkyl, hydroxyalkyl, aminoalkyl, alkoxyalkyl, haloalkoxyalkyl, alkoxy, or haloalkoxy;

$R^{12}$ are each independently hydrogen or $C_{1-4}$ alkyl;

$R^{13}$ is hydrogen, $C_{1-10}$ alkyl, or glycosyl;

$R^{14a}$ and $R^{14b}$ are each independently hydrogen, $C_{1-6}$ alkyl, $C_{3-6}$ cycloalkyl, $C_{4-6}$ heterocyclyl, alkylamino, haloalkyl, hydroxyalkyl, aminoalkyl, alkoxyalkyl, haloalkoxyalkyl, alkoxy, or haloalkoxy; and $R^{15}$ are each independently halo, oxo, cyano, hydroxyl, amino, alkyl, alkoxy, or alkylamino; or alternatively, two $R^{15}$, taken together with the atom(s) to which they are attached, form a carbocyclyl or heterocyclyl moiety.

It should be understood by one skilled in the art that the dashed circle in Formula (I) denotes an aromatic ring formed by $X^1$, $X^2$, $X^3$, $X^4$, and the carbon atom; and the wavy or squiggly lines indicate the inclusion of geometric isomers, e.g., $R^3$ and $R^4$ can be at either cis or trans positions.

In any one of the preceding embodiments of Formula (I), $X^2$ is N or $NR^6$.

In any one of the preceding embodiments of Formula (I), two $R^{Y1}$, together form a $C_{1-3}$ alkylene bridge moiety. $(R^{Y1})_f$ denotes one or more optional substituent groups on any of the suitable ring member atoms, and each of $R^{Y1}$ is independent and can be the same or different.

In any one of the preceding embodiments of Formula (I), the

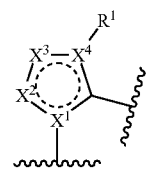

moiety is

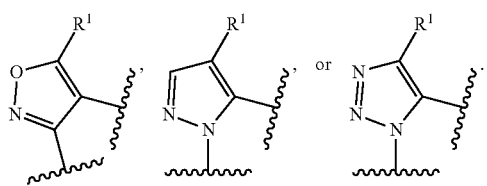

In any one of the preceding embodiments of Formula (I), L is a covalent bond, O, S, NH, $C_{1-3}$ alkylene, —($C_{1-3}$ alkylene)$_a$-O—($C_{1-3}$ alkylene)$_b$-, —($C_{1-3}$ alkylene)$_a$-S—($C_{1-3}$ alkylene)$_b$-, or —($C_{1-3}$ alkylene)$_a$-NH—($C_{1-3}$ alkylene)$_b$-, wherein the $C_{1-3}$ alkylene is substituted with 0 to 3 $R^{11}$; and $L^2$ is a covalent bond.

In any one of the preceding embodiments of Formula (I), the

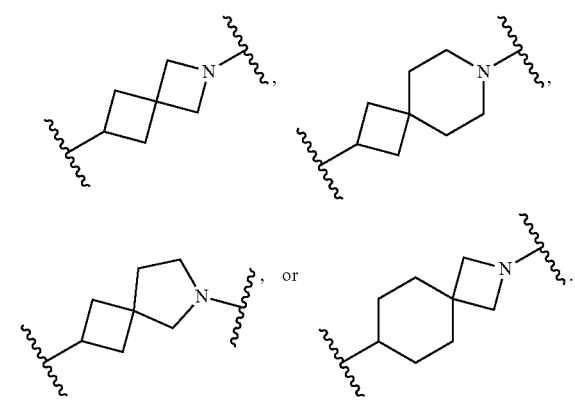

moiety is:

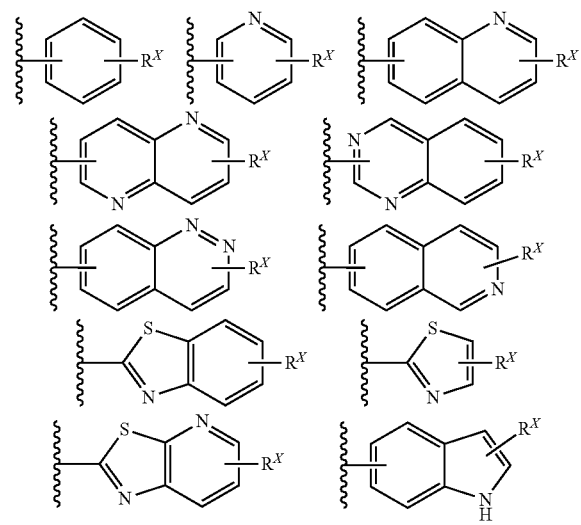

In any one of the preceding embodiments of Formula (I), Z is phenyl or 5- to 10-membered heteroaryl, wherein the phenyl and heteroaryl are independently substituted with 0 to 5 $R^8$, wherein $R^8$ is the same as defined above.

In any one of the preceding embodiments of Formula (I), $L^1$ is a covalent bond.

In any one of the preceding embodiments of Formula (I), —Z—$R^x$ is selected from

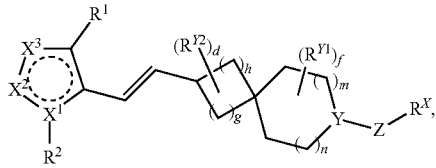

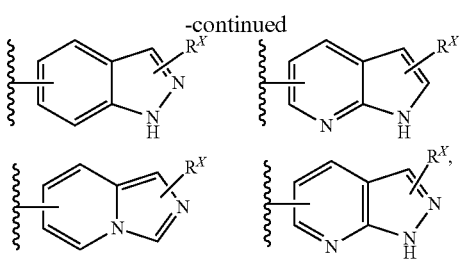

wherein the Z moiety is further substituted with 0 to 3 $R^8$, and $R^8$ is the same as defined above.

In any one of the preceding embodiments of Formula (I), Y is N.

In any one of the preceding embodiments of Formula (I), Y is CH; and $L^1$ is a covalent bond, O, S, or NH.

In any one of the preceding embodiments of Formula (I), $R^2$ is phenyl or 6-membered heteroaryl, wherein the phenyl or heteroaryl is substituted with 0 to 5 $R^{10}$.

In any one of the preceding embodiments of Formula (I), $L^2$ is a covalent bond.

In any one of the preceding embodiments of Formula (I), $R^3$ and $R^4$ are each independently hydrogen or $C_{1-6}$ alkyl.

In one embodiment of Formula (I), the compound is represented by Formula (II):

(II)

$X^1$ is C or N;
$X^2$ and $X^3$ are each independently CH, N, O, or S;
Z is phenyl or a 5- to 10-membered heteroaryl, wherein the phenyl and heteroaryl are independently substituted with 0 to 3 $R^8$;
$R^X$ is —C(O)O$R^{13}$;
each $R^Y$ is independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy;
f is an integer of 0, 1, or 2;
$R^1$ is $C_{1-6}$ alkyl or $C_{3-5}$ cycloalkyl, wherein the alkyl and cycloalkyl are independently substituted with 0 to 3 $R^9$;
$R^2$ is phenyl or 6-membered heteroaryl, wherein the phenyl and heteroaryl are substituted with 0 to 3 $R^{10}$; and
h, g, m, n, $R^8$, $R^9$, $R^{10}$, and $R^{13}$ are the same as defined in claim 1.

In any one of the preceding embodiments of Formula (II), the

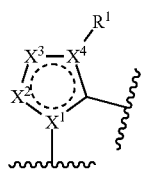

moiety is a ring moiety is

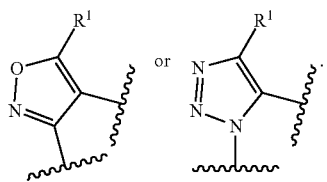

In any one of the preceding embodiments of Formula (II), $R^2$ is phenyl or pyridinyl, each of which is independently substituted with 0 to 3 $R^{10}$.

In any one of the preceding embodiments of Formula (II), m and n are both 1.

In any one of the preceding embodiments of Formula (II), f is 0.

In any one of the preceding embodiments of Formula (II), Z is a 5- or 6-membered monocyclic heteroaryl or 8- to 10-membered bicyclic heteroaryl, wherein the heteroaryl is independently substituted with 0 to 3 $R^8$.

In any one of the preceding embodiments of Formula (II), $R^X$ is —C(O)OH.

In one embodiment of Formula (I) or Formula (III), $X^1$ is C.

In one embodiment of Formula (I) or Formula (II), $X^2$ is N.

In one embodiment of Formula (I) or Formula (II), $X^3$ is O.

In one embodiment of Formula (I), $X^4$ is C.

In one embodiment of Formula (I), X is C and $X^4$ is C.

In one embodiment of Formula (I) or Formula (II), one of $X^2$ and $X^3$ is N and the other of $X^2$ and $X^3$ is O.

In one embodiment of Formula (I) or Formula (II), $X^2$ is N and $X^3$ is O.

In one embodiment of Formula (I) or Formula (II), $X^2$ is O and $X^3$ is N.

In one embodiment of Formula (I) or Formula (II), X is C; $X^2$ is N; and $X^3$ is O.

In one embodiment of Formula (I), X is C; one of $X^2$ and $X^3$ is N and the other of $X^2$ and $X^3$ is O; and $X^4$ is C.

In one embodiment of Formula (I), $X^1$ is C; $X^2$ is N; $X^3$ is O; and $X^4$ is C.

In one embodiment of Formula (I), $X^1$ is C; $X^2$ is O; $X^3$ is N; and $X^4$ is C.

In one embodiment of Formula (I) or Formula (II), $X^1$ is N; $X^2$ is N; and $X^3$ is N.

In one embodiment of Formula (I) or Formula (II), the

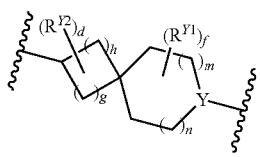

moiety is

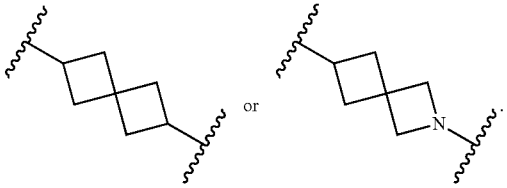

In one embodiment of Formula (I), $L^1$ is a covalent bond, $C_{1-3}$ alkylene, $C_{1-3}$ heteroalkylene, $C_{2-4}$ alkenylene, $C_{2-4}$ alkynylene, aryl, or a 5- to 6-membered heteroaryl containing 1 to 4 heteroatoms independently selected from N, O, and S; wherein the alkylene, heteroalkylene, aryl, and heteroaryl are each independently substituted with 0 to $3R^{11}$.

In one embodiment of Formula (I), $L^1$ is a covalent bond, $C_{1-3}$ alkylene, $C_{1-3}$ heteroalkylene, $C_{2-4}$ alkenylene, or $C_{2-4}$ alkynylene; wherein the alkylene and heteroalkylene are each independently substituted with 0 to 3 $R^{11}$.

In one embodiment of Formula (I), $L^1$ is a covalent bond, $C_{1-3}$ alkylene, —($C_{1-3}$ alkylene)-O—, or —O—($C_{1-3}$ alkylene)-, wherein the $C_{1-3}$ alkylene is substituted with 0 to $3R^{11}$.

In one embodiment of Formula (I), $L^1$ is a covalent bond, $C_{1-2}$ alkylene, —$CH_2O$—, or —$OCH_2$—, wherein the $C_{1-3}$ alkylene is substituted with 0 to 3 $R^D$.

In one embodiment of Formula (I), $L^1$ is a covalent bond or —$CH_2O$—.

In one embodiment of Formula (I) or Formula (II), Z is phenyl or 5- to 10-membered heteroaryl, wherein the phenyl and heteroaryl are independently substituted with 0 to $3R^8$.

In one embodiment of Formula (I) or Formula (II), Z is a 5-membered heteroaryl, 6-membered heteroaryl, 9-membered heteroaryl, or 10-membered heteroaryl, wherein the 5-membered heteroaryl, 6-membered heteroaryl, 9-membered heteroaryl, and 10-membered heteroaryl are independently substituted with 0 to 3 $R^8$.

In one embodiment of Formula (I) or Formula (II), Z is phenyl, pyrazolyl, pyridinyl, benzo[d]thiazolyl, thiazolo[5,4-b]pyridinyl, quinolinyl, isoquinolinyl, cinnolinyl, or naphthyridinyl, each substituted with 0 to 2 $R^8$.

In one embodiment of Formula (I) or Formula (II), $R^8$ is each independently F, Cl, cyano, hydroxyl, amino, —$OR^a$, —$NR^cR^c$, —$C(O)R^b$, —$C(O)OR^b$, —$C(O)NR^cR^c$, —$OC(O)R^b$, —$NR^bC(O)R^b$, —$NR^bC(O)OR^b$, $C_{1-4}$ alkyl, $C_{1-2}$ fluoroalkyl, carbocyclyl, or heterocyclyl; wherein the alkyl, carbocyclyl, and heterocyclyl, by themselves or as part of another group, are each independently substituted with 0 to 4 $R^d$.

In one embodiment of Formula (I) or Formula (II), $R^8$ is each independently F, Cl, —$OR^a$, —$NR^cR^c$, —$C(O)R^b$, —$C(O)OR^b$, —$C(O)NR^cR^c$, $C_{1-4}$ alkyl, $C_{1-2}$ fluoroalkyl, $C_{3-6}$ cycloalkyl, or 5- to 6-membered heterocyclyl; wherein the alkyl, cycloalkyl, and heterocyclyl, by themselves or as part of another group, are each independently substituted with 0 to 4 $R^d$.

In one embodiment of Formula (I) or Formula (II), $R^8$ is each independently F, —$CH_3$, —$CH_2CH_3$, —$CH(CH_3)_2$, —$CF_3$, —$CH_2OCH_3$, —$OCH_3$, -$OCD_3$, —$OCH_2CH_3$, —$OCH(CH_3)_2$, cyclopropyl, methylpiperazinyl, —O(cyclopropyl), —O(cyclobutyl), —O(fluorocyclobutyl), —O(oxetanyl), or —O(tetrahydrofuranyl).

In one embodiment of Formula (I) or Formula (II), $R^X$ is -L-$R^Z$, wherein $L^3$ is a covalent bond or a $C_{1-2}$ alkylene, wherein the $C_{1-2}$ alkylene is substituted with 0 to 3 $R^{15}$; and $R^Z$ is —CN, —$C(O)OR^{13}$, —$C(O)NR^{14a}R^{14b}$,

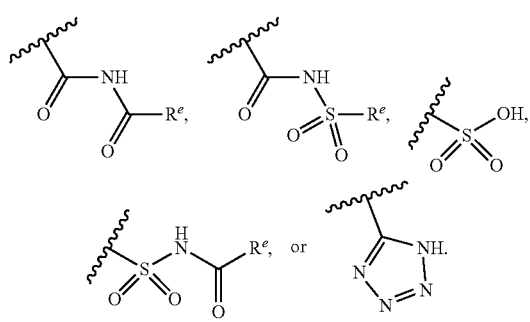

In one embodiment of Formula (I) or Formula (II), $R^X$ is -L-$R^Z$, wherein $L^3$ is a covalent bond or a $C_{1-2}$ alkylene, wherein the $C_{1-2}$ alkylene is substituted with 0 to 2 $R^{15}$; and $R^Z$ is —CN, —C(O)O$R^{13}$, or —C(O)N$R^{14a}R^{14b}$.

In one embodiment of Formula (I) or Formula (II), $R^X$ is —CN, —C(O)OH, —CH$_2$C(O)OH, or —C(O)NH$_2$.

In one embodiment of Formula (I), $R^3$ is hydrogen or —CH$_3$.

In one embodiment of Formula (I), $R^4$ is hydrogen or —CH$_3$.

In one embodiment of Formula (I), $R^3$ and $R^4$ are each independently hydrogen or —CH$_3$.

In one embodiment of Formula (I), $R^3$ is hydrogen and $R^4$ is hydrogen.

In one embodiment of Formula (I) or Formula (II), $R^1$ is $C_{1-4}$ alkyl, $C_{3-5}$ cycloalkyl, or $C_{4-6}$ heterocyclyl, wherein the alkyl and cycloalkyl are substituted with 0 to 3 $R^9$.

In one embodiment of Formula (I) or Formula (II), $R^1$ is $C_{1-3}$ alkyl or $C_{3-5}$ cycloalkyl, wherein the alkyl and cycloalkyl are substituted with 0 to 3 $R^9$.

In one embodiment of Formula (I) or Formula (II), $R^1$ is —CH(CH$_3$)$_2$ or $C_{3-4}$ cycloalkyl.

In one embodiment of Formula (I) or Formula (II), RI is —CH(CH$_3$)$_2$ or cyclopropyl.

In one embodiment of Formula (I) or Formula (II), $R^1$ is cyclopropyl.

In one embodiment of Formula (I) or Formula (II), $R^1$ is —CH(CH$_3$)$_2$.

In one embodiment of Formula (I) or Formula (II), $L^2$ is a covalent bond, O, N$R^{18}$, $C_{1-2}$ alkylene, —OCH$_2$—, or —CH$_2$O—.

In one embodiment of Formula (I) or Formula (II), $L^2$ is a covalent bond, $C_{1-2}$ alkylene, —OCH$_2$—, or —CH$_2$O—.

In one embodiment of Formula (I) or Formula (II), $L^2$ is a covalent bond or —CH$_2$—.

In one embodiment of Formula (I) or Formula (II), $R^2$ is phenyl, 5- to 6-membered heteroaryl, 3- to 6-membered carbocyclyl, or 4- to 6-membered heterocyclyl, wherein the phenyl, heteroaryl, carbocyclyl, and heterocyclyl are independently substituted with 0 to 5$R^{10}$.

In one embodiment of Formula (I) or Formula (II), $R^2$ is phenyl or 5- to 6-membered heteroaryl, wherein the phenyl and heteroaryl are independently substituted with 0 to 4 $R^{10}$.

In one embodiment of Formula (I) or Formula (II), $R^2$ is phenyl or 6-membered heteroaryl, wherein the phenyl and heteroaryl are independently substituted with 0 to 4 $R^{10}$.

In one embodiment of Formula (I) or Formula (II), $R^2$ is phenyl or pyridinyl, each substituted with 1 or 2 $R^{10}$.

In one embodiment of Formula (I) or Formula (II), $R^{10}$ is each independently F, Cl, cyano, hydroxyl, amino, $C_{1-3}$ alkyl, or $C_{1-2}$ fluoroalkyl.

In one embodiment of Formula (I) or Formula (II), $R^{10}$ is each independently F, Cl, —CH$_3$, —CH$_2$CH$_3$, —CH$_2$F, —CHF$_2$, or —CF$_3$.

In one embodiment of Formula (I) or Formula (II), $R^{10}$ is each independently Cl or —CF$_3$.

In one embodiment of Formula (I) or Formula (II), $R^2$ is phenyl, 5- to 6-membered heteroaryl, 3- to 6-membered carbocyclyl, or 4- to 6-membered heterocyclyl, wherein the phenyl, heteroaryl, carbocyclyl, and heterocyclyl are independently substituted with 0 to 5$R^{10}$; and $R^{10}$ is each independently F, Cl, cyano, hydroxyl, amino, $C_{1-3}$ alkyl, or $C_{1-2}$ fluoroalkyl.

In one embodiment of Formula (I) or Formula (II), $R^2$ is phenyl, 5- to 6-membered heteroaryl, 3- to 6-membered carbocyclyl, or 4- to 6-membered heterocyclyl, wherein the phenyl, heteroaryl, carbocyclyl, and heterocyclyl are independently substituted with 0 to 5$R^{10}$; and $R^{10}$ is each independently F, Cl, —CH$_3$, —CH$_2$CH$_3$, —CH$_2$F, —CHF$_2$, or —CF$_3$.

One embodiment provides a compound of Formula (I), or a stereoisomer, a tautomer, or a pharmaceutically acceptable salt or solvate thereof; wherein:
$X^1$ is C;
$X^2$ is N;
$X^3$ is O;
$X^4$ is C;

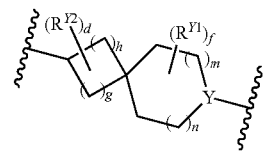

moiety is

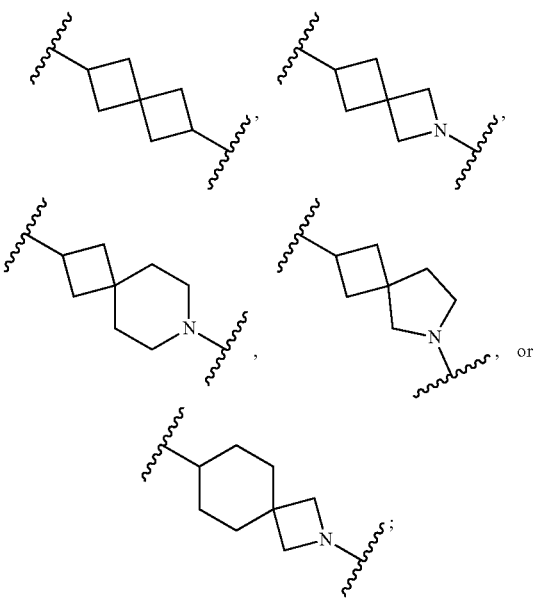

$L^1$ is a covalent bond, $C_{1-2}$ alkylene, —CH$_2$O—, or —OCH$_2$—;
$R^3$ and $R^4$ are each independently hydrogen or —CH$_3$;
Z is phenyl or 5- to 10-membered heteroaryl, wherein the phenyl and heteroaryl are independently substituted with 0 to 3 $R^8$;

$R^8$ is each independently F, Cl, —OR$^a$, —NR$^c$R$^c$, —C(O)R$^b$, —C(O)OR$^b$, —C(O)NR$^c$R$^c$, C$_{1-4}$ alkyl, C$_{1-2}$ fluoroalkyl, C$_{3-6}$ cycloalkyl, and 5- to 6-membered heterocyclyl; wherein the alkyl, cycloalkyl, and heterocyclyl, by themselves or as part of another group, are each independently substituted with 0 to 4 R$^d$.

$R^X$ is -L$^3$-R$^Z$;

L$^3$ is a covalent bond or C$_{1-2}$ alkylene, wherein the C$_{1-2}$ alkylene is substituted with 0 to 2R$^{15}$;

R$^Z$ is —CN, —C(O)OR$^{13}$, or —C(O)NR$^{14a}$R$^{14b}$;

R$^{13}$ is hydrogen and C$_{1-2}$ alkyl;

R$^{14a}$ and R$^{14b}$ are each independently hydrogen, C$_{1-2}$ alkyl, or cyclopropyl;

R$^1$ is cyclopropyl;

L$^2$ is a covalent bond, C$_{1-2}$ alkylene, —OCH$_2$—, or —CH$_2$O—;

R$^2$ is phenyl or 6-membered heteroaryl, wherein the phenyl and heteroaryl are substituted with 0 to 3 R$^{10}$;

R$^8$ is each independently F, Cl, cyano, hydroxyl, amino, —OR$^a$, —NR$^c$R$^c$, —C(O)R$^b$, —C(O)OR$^b$, —C(O)NR$^c$R$^c$, —OC(O)R$^b$, —NR$^b$C(O)R$^b$, —NR$^b$C(O)OR$^b$, C$_{1-4}$ alkyl, C$_{1-2}$ fluoroalkyl, carbocyclyl, or heterocyclyl; wherein the alkyl, carbocyclyl, and heterocyclyl, by themselves or as part of another group, are each independently substituted with 0 to 4 R$^d$;

R$^d$ is each independently F, Cl, C$_{1-2}$ alkyl, or C$_{1-2}$ fluoroalkyl; and R$^{10}$ is each independently F, Cl, cyano, hydroxyl, amino, C$_{1-3}$ alkyl, or C$_{1-2}$ fluoroalkyl.

One embodiment provides a compound of Formula (I), or a stereoisomer, a tautomer, or a pharmaceutically acceptable salt or solvate thereof; wherein:

X$^1$ is C;
X$^2$ is N;
X$^3$ is O;
X$^4$ is C;

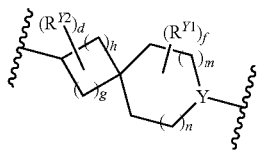

moiety is

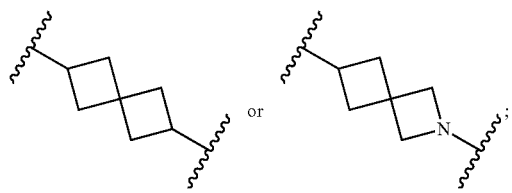 [SMILES: *C1CC2(C1)CC(*)C2 ; *C1CC2(C1)CN(*)C2]

L$^1$ is a covalent bond or —CH$_2$O—;

Z is phenyl, pyrazolyl, pyridinyl, benzo[d]thiazolyl, thiazolo[5,4-b]pyridinyl, quinolinyl, isoquinolinyl, cinnolinyl, or naphthyridinyl, each substituted with 0 to 2 R$^8$;

R$^X$ is —CN, —C(O)OH, —CH$_2$C(O)OH, or —C(O)NH$_2$;

RI is cyclopropyl;

L$^2$ is a covalent bond;

R$^2$ is phenyl or pyridinyl, each substituted with 1 or 2 R$^{10}$;

R$^3$ is hydrogen;

R$^4$ is hydrogen;

R$^8$ is each independently F, —CH$_3$, —CH$_2$CH$_3$, —CH(CH$_3$)$_2$, —CF$_3$, —CH$_2$OCH$_3$, —OCH$_3$, —OCD$_3$, —OCH$_2$CH$_3$, —OCH(CH$_3$)$_2$, cyclopropyl, methylpiperazinyl, —O(cyclopropyl), —O(cyclobutyl), —O(fluorocyclobutyl), —O(oxetanyl), or —O(tetrahydrofuranyl); and R$^{10}$ is each independently Cl or —CF$_3$.

In one embodiment, the present invention provides, inter alia, compounds selected from any one of the Examples as described in the specification, or a stereoisomer, a tautomer, or a pharmaceutically acceptable salt or solvate thereof.

II. Pharmaceutical Compositions, Therapeutic Utilities, and Combinations

In another embodiment, the present invention provides a composition comprising at least one of the compounds of the present invention, or a stereoisomer, a tautomer, or a pharmaceutically acceptable salt or a solvate thereof.

In another embodiment, the present invention provides a pharmaceutical composition comprising a pharmaceutically acceptable carrier and at least one of the compounds of the present invention or a stereoisomer, a tautomer, or a pharmaceutically acceptable salt or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, or a pharmaceutically acceptable salt or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising one or more additional therapeutic agents.

In another embodiment, the present invention provides a method for the treatment of a disease, disorder, or condition associated with dysregulation of bile acids in a patient in need of such treatment, and the method comprises administering a therapeutically effective amount of a compound of the present invention, or a stereoisomer, a tautomer, or a pharmaceutically acceptable salt or solvate thereof, to the patient.

In another embodiment, the present invention provides a method for the treatment of a disease, disorder, or condition associated with activity of farnesoid X receptor (FXR) in a patient in need of such treatment comprising administering a therapeutically effective amount of a compound of the present invention, or a stereoisomer, a tautomer, or a pharmaceutically acceptable salt or solvate thereof, to the patient.

In another embodiment, the present invention provides a method for the treatment of the disease, disorder, or condition comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for eliciting an farnesoid X receptor (FXR) agonizing effect in a patient comprising administering a therapeutically effective amount of a compound of the present invention, or a stereoisomer, a tautomer, or a pharmaceutically acceptable salt or solvate thereof, to the patient.

In some embodiments, the disease, disorder, or condition is associated with FXR dysfunction include pathological fibrosis, cancer, inflammatory disorders, metabolic, or cholestatic disorders.

In some embodiments, the disease, disorder, or condition is associated with fibrosis, including liver, biliary, renal, cardiac, dermal, ocular, and pancreatic fibrosis.

In other embodiments, the disease, disorder, or condition is associated with cell-proliferative disorders, such as cancer. In some embodiments, the cancer includes solid tumor growth or neoplasia. In other embodiments, the cancer includes tumor metastasis. In some embodiments, the cancer is of the liver, gall bladder, small intestine, large intestine, kidney, prostate, bladder, blood, bone, brain, breast, central nervous system, cervix, colon, endometrium, esophagus, genitalia, genitourinary tract, head, larynx, lung, muscle tissue, neck, oral or nasal mucosa, ovary, pancreas, skin, spleen, stomach, testicle, or thyroid. In other embodiments, the cancer is a carcinoma, sarcoma, lymphoma, leukemia, melanoma, mesothelioma, multiple myeloma, or seminoma.

Examples of diseases, disorders, or conditions associated with the activity of FXR that can be prevented, modulated, or treated according to the present invention include, but are not limited to, transplant injection, fibrotic disorders (e. g., liver fibrosis, kidney fibrosis), inflammatory disorders (e.g., acute hepatitis, chronic hepatitis, non-alcoholic steatohepatitis (NASH), irritable bowel syndrome (IBS), inflammatory bowel disease (IBD)), as well as cell-proliferative disorders (e.g., cancer, myeloma, fibroma, hepatocellular carcinoma, colorectal cancer, prostate cancer, leukemia, Kaposi's sarcoma, solid tumors).

The fibrotic disorders, inflammatory disorders, as well as cell-proliferative disorders that are suitable to be prevented or treated by the compounds of the present invention include, but are not limited to, non-alcoholic fatty liver disease (NAFLD), alcoholic or non-alcoholic steatohepatitis (NASH), acute hepatitis, chronic hepatitis, liver cirrhosis, primary biliary cirrhosis, primary sclerosing cholangitis, drug-induced hepatitis, biliary cirrhosis, portal hypertension, regenerative failure, liver hypofunction, hepatic blood flow disorder, nephropathy, irritable bowel syndrome (IBS), inflammatory bowel disease (IBD), abnormal pancreatic secretion, benign prostatic hyperplasia, neuropathic bladder disease, diabetic nephropathy, focal segmental glomerulosclerosis, IgA nephropathy, nephropathy induced by drugs or transplantation, autoimmune nephropathy, lupus nephritis, liver fibrosis, kidney fibrosis, chronic kidney disease (CKD), diabetic kidney disease (DKD), skin fibrosis, keloids, systemic sclerosis, scleroderma, virally-induced fibrosis, idiopathic pulmonary fibrosis (IPF), interstitial lung disease, non-specific interstitial pneumonia (NSIP), usual interstitial pneumonia (UIP), radiation-induced fibrosis, familial pulmonary fibrosis, airway fibrosis, chronic obstructive pulmonary disease (COPD), spinal cord tumor, hernia of intervertebral disk, spinal canal stenosis, heart failure, cardiac fibrosis, vascular fibrosis, perivascular fibrosis, foot-and-mouth disease, cancer, myeloma, fibroma, hepatocellular carcinoma, colorectal cancer, prostate cancer, leukemia, chronic lymphocytic leukemia, Kaposi's sarcoma, solid tumors, cerebral infarction, cerebral hemorrhage, neuropathic pain, peripheral neuropathy, age-related macular degeneration (AMD), glaucoma, ocular fibrosis, corneal scarring, diabetic retinopathy, proliferative vitreoretinopathy (PVR), cicatricial pemphigoid glaucoma filtration surgery scarring, Crohn's disease or systemic lupus erythematosus; keloid formation resulting from abnormal wound healing; fibrosis occurring after organ transplantation, myelofibrosis, and fibroids. In one embodiment, the present invention provides a method for the treatment of a fibrotic disorder, an inflammatory disorder, or a cell-proliferative disorder, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of a fibrotic disorder, an inflammatory disorder, or a cell-proliferative disorder thereof.

In another embodiment, the present invention also provides the use of a compound of the present invention for the manufacture of a medicament for the treatment of a fibrotic disorder, an inflammatory disorder, or a cell-proliferative disorder thereof.

In another embodiment, the present invention provides a method for the treatment of a fibrotic disorder, an inflammatory disorder, or a cell-proliferative disorder, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of a fibrotic disorder, an inflammatory disorder, or a cell-proliferative disorder.

The compounds of the present invention may be employed in combination with additional therapeutic agent(s), such as one or more anti-fibrotic and/or anti-inflammatory therapeutic agents.

In one embodiment, additional therapeutic agent(s) used in combined pharmaceutical compositions or combined methods or combined uses, are selected from one or more, preferably one to three, of the following therapeutic agents: TGFβ receptor inhibitors (for example, galunisertib), inhibitors of TGFβ synthesis (for example, pirfenidone), inhibitors of vascular endothelial growth factor (VEGF), platelet-derived growth factor (PDGF) and fibroblast growth factor (FGF) receptor kinases (for example, nintedanib), humanized anti-αvβ6 integrin monoclonal antibody (for example, 3G9), human recombinant pentraxin-2, recombinant human Serum Amyloid P, recombinant human antibody against TGFβ-1, -2, and -3, endothelin receptor antagonists (for example, macitentan), interferon gamma, c-Jun amino-terminal kinase (JNK) inhibitor (for example, 4-[[9-[(3S)-tetrahydro-3-furanyl]-8-[(2,4,6-trifluorophenyl)amino]-9H-purin-2-yl]amino]-trans-cyclohexanol,
3-pentylbenzeneacetic acid (PBI-4050), tetra-substituted porphyrin derivative containing manganese (III), monoclonal antibody targeting eotaxin-2, interleukin-13 (IL-13) antibody (for example, lebrikizumab, tralokinumab), bispecific antibody targeting interleukin 4 (IL-4) and interleukin 13 (IL-13), NK1 tachykinin receptor agonist (for example, Sar$^9$, Met($O_2$)$^{11}$-Substance P), Cintredekin Besudotox, human recombinant DNA-derived, IgG1 kappa monoclonal antibody to connective growth factor, and fully human IgG1 kappa antibody, selective for CC-chemokine ligand 2 (for example, carlumab, CCX140), antioxidants (for example, N-acetylcysteine), phosphodiesterase 5 (PDE5) inhibitors (for example, sildenafil), agents for treatment of obstructive airway diseases such as muscarinic antagonists (for example, tiotropium, ipatropium bromide), adrenergic 2 agonists (for example, salbutamol, salmeterol), corticosteroids (for example, triamcinolone, dexamethasone, fluticasone), immunosuppressive agents (for example, tacrolimus, rapamycin, pimecrolimus), and therapeutic agents useful for the treatment of fibrotic conditions, such as liver, biliary, and kidney fibrosis, Non-Alcoholic Fatty Liver Disease (NALFD), Non-Alcoholic Steato-Hepatitis (NASH), cardiac fibrosis, Idiopathic Pulmonary Fibrosis (IPF), and systemic sclerosis. The therapeutic agents useful for the treatment of such fibrotic conditions include, but are not limited to, FXR agonists (for example OCA, GS-9674, and LJN452), LOXL2 inhibitors (for example simtuzumab), LPA1 antagonists (for example, BMS-986020 and SAR 100842), PPAR modulators (for example, elafibrinor, pioglitazone, and saroglitazar, IVA337), SSAO/VAP-1 inhibitors (for example, PXS-4728A and SZE5302), ASK-1 inhibitors (for example GS-4997 or selonsertib), ACC inhibitors (for example, CP-640186 and NDI-010976 or GS-0976), FGF21 mimetics (for example, LY2405319 and BMS-986036), caspase inhibitors (for example, emricasan), NOX4 inhibitors (for example, GKT137831), MGAT2 inhibitor (for example, BMS-963272), αV integrin inhibitors (for example, abituzumab) and bile acid/fatty acid conjugates (for example aramchol). The FXR agonists of various embodiments of the present invention may also be used in combination with one or more therapeutic agents such as CCR2/5 inhibitors (for example, cenicriviroc), Galectin-3 inhibitors (for example, TD-139, GR-MD-02), leukotriene receptor antagonists (for example, tipelukast, montelukast), SGLT2 inhibitors (for example, dapagliflozin, remogliflozin), GLP-1 receptor agonists (for example, liraglutide and semaglutide), FAK inhibitors (for example, GSK-2256098), CB1 inverse agonists (for example, JD-5037), CB2 agonists (for example, APD-371 and JBT-101), autotaxin inhibitors (for example, GLPG1690), prolyl t-RNA synthetase inhibitors (for example, halofugenone), FPR2 agonists (for example, ZK-994), and THR agonists (for example, MGL:3196). In another embodiment, additional therapeutic agent(s) used in combined pharmaceutical compositions or combined methods or combined uses, are selected from one or more, preferably one to three, of immunoncology agents, such as Alemtuzumab, Atezolizumab, Ipilimumab, Nivolumab, Ofatumumab, Pembrolizumab, and Rituximab.

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g. as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The terms "treating" or "treatment" as used herein refer to an approach for obtaining beneficial or desired results, including clinical results, by using a compound or a composition of the present invention. For purposes of this invention, beneficial or desired clinical results include, but are not limited to, one or more of the following: decreasing the severity and/or frequency one or more symptoms resulting from the disease, disorder, or condition; diminishing the extent of or causing regression of the disease, disorder, or condition; stabilizing the disease, disorder, or condition (e.g., preventing or delaying the worsening of the disease, disorder, or condition); delay or slowing the progression of the disease, disorder, or condition; ameliorating the disease, disorder, or condition state; decreasing the dose of one or more other medications required to treat the disease, disorder, or condition; and/or increasing the quality of life.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.01 to about 1000 mg per day, and most preferably between about 0.01 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 0.1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., ASK-1 inhibitors, CCR2/5 antagonists, autotaxin inhibitors, LPA1 receptor antagonists or other pharmaceutically active material.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving FXR agonists. Such compounds may be provided in a commercial kit, for example, for use in pharmaceutical research involving FXR agonist activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof, and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of fibrosis and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

III. Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. As used herein, "a compound of the invention" or "compounds of the invention" means one or more compounds encompassed by any one of Formula (I), (IIa), and (IIb), or stereoisomers, tautomers, or pharmaceutically acceptable salts or solvates thereof.

As used herein, the term "alkyl" or "alkylene" is intended to include both branched and straight-chain saturated aliphatic hydrocarbon groups having the specified number of carbon atoms. While "alkyl" denotes a monovalent saturated aliphatic radical (such as ethyl), "alkylene" denotes a bivalent saturated aliphatic radical (such as ethylene). For example, "$C_1$ to $C_{10}$ alkyl" or "$C_{1-10}$ alkyl" is intended to include $C_1$, $C_2$, $C_3$, $C_4$, $C_5$, $C_5$, $C_7$, $C_8$, $C_9$, and $C_{10}$ alkyl groups. "$C_1$ to $C_{10}$ alkylene" or "$C_{1-10}$ alkylene", is intended to include $C_1$, $C_2$, $C_3$, $C_4$, $C_5$, $C_6$, $C_7$, $C_8$, $C_9$, and $C_{10}$ alkylene groups. Additionally, for example, "$C_1$ to $C_6$ alkyl" or "$C_{1-6}$ alkyl" denotes alkyl having 1 to 6 carbon atoms; and "$C_1$ to $C_6$ alkylene" or "$C_{1-6}$ alkylene" denotes alkylene having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an alkylamino (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —CH$_2$CH$_2$—O—CH$_3$, etc.), an alkylaminoalkyl (e.g., —CH$_2$NHCH$_3$, —CH$_2$N(CH$_3$)$_2$, etc.), or a thioalkyl ether (e.g.,—CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. While "alkenyl" denotes a monovalent radical, "alkenylene" denotes a bivalent radical. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. While "alkynyl" denotes a monovalent radical, "alkynylene" denotes a bivalent radical. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

As used herein, "arylalkyl" (a.k.a. aralkyl), "heteroarylalkyl" "carbocyclylalkyl" or "heterocyclylalkyl" refers to an acyclic alkyl radical in which one of the hydrogen atoms bonded to a carbon atom, typically a terminal or $sp^3$ carbon atom, is replaced with an aryl, heteroaryl, carbocyclyl, or heterocyclyl radical, respectively. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl, heteroarylalkyl, carbocyclylalkyl, or heterocyclylalkyl group can comprise 4 to 20 carbon atoms and 0 to 5 heteroatoms, e.g., the alkyl moiety may contain 1 to 6 carbon atoms.

The term "benzyl", as used herein, refers to a methyl group on which one of the hydrogen atoms is replaced by a phenyl group, wherein said phenyl group may optionally be substituted with 1 to 5 groups, preferably 1 to 3 groups, —OH, —OCH$_3$, Cl, F, Br, I, —CN, —NO$_2$, —NH$_2$, —NH(CH$_3$), —N(CH$_3$)$_2$, —CF$_3$, —OCF$_3$, —C(=O)CH$_3$, —SCH$_3$, —S(=O)CH$_3$, —S(=O)$_2$CH$_3$, —CH$_3$, —CH$_2$CH$_3$, —CO$_2$H, and —CO$_2$CH$_3$. "Benzyl" can also be represented by formula "Bn".

The term "lower alkoxy", "alkoxy" or "alkyloxy", "aryloxy" or "aralkoxy" refers to any of the above alkyl, aralkyl or aryl groups linked to an oxygen atom. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "lower alkylthio", "alkylthio", "thioalkoxy", "arylthio", or "aralkylthio" represents an alkyl, aryl, or aralkyl group as defined above with the indicated number of carbon atoms attached through a sulphur bridge; for example methyl-S— and ethyl-S—.

The term "alkanoyl" or "alkylcarbonyl" as used herein alone or as part of another group refers to alkyl linked to a carbonyl group. For example, alkylcarbonyl may be represented by alkyl-C(O)—. "$C_1$ to $C_6$ alkylcarbonyl" (or alkylcarbonyl), is intended to include $C_1$, $C_2$, $C_3$, $C_4$, $C_5$, and $C_6$ alkyl-C(O)— groups.

The term "alkylsulfonyl" or "sulfonamide" as used herein alone or as part of another group refers to alkyl or amino linked to a sulfonyl group. For example, alkylsulfonyl may be represented by —S(O)$_2$R', while sulfonamide may be represented by —S(O)$_2$NR$^c$R$^d$. R' is $C_1$ to $C_6$ alkyl; and R$^c$ and R$^d$ are the same as defined below for "amino".

The term "carbamate" as used herein alone or as part of another group refers to oxygen linked to an amido group. For example, carbamate may be represented by N(R$^c$R$^d$)—C(O)—O—, and R$^c$ and R$^d$ are the same as defined below for "amino".

The term "amido" as used herein alone or as part of another group refers to amino linked to a carbonyl group. For example, amido may be represented by N(R$^c$R$^d$)—C(O)—, and R$^c$ and R$^d$ are the same as defined below for "amino".

The term "amino" is defined as —NR$^{c1}$R$^{c2}$, wherein R$^{c1}$ and R$^{c2}$ are independently H or $C_{1-6}$ alkyl; or alternatively, R$^{c1}$ and R$^{c2}$, taken together with the atoms to which they are attached, form a 3- to 8-membered heterocyclic ring which is optionally substituted with one or more group selected from halo, cyano, hydroxyl, amino, oxo, $C_{1-6}$ alkyl, alkoxy, and aminoalkyl. When R$^{c1}$ or R$^{c2}$ (or both of them) is $C_{1-6}$ alkyl, the amino group can also be referred to as alkylamino. Examples of alkylamino group include, without limitation, —NH$_2$, methylamino, ethylamino, propylamino, isopropylamino and the like.

The term "aminoalkyl" refers to an alkyl group on which one of the hydrogen atoms is replaced by an amino group. For example, aminoalkyl may be represented by N(R$^{c1}$R$^{c2}$)-alkylene-. "$C_1$ to $C_6$" or "$C_{1-6}$" aminoalkyl" (or aminoalkyl), is intended to include $C_1$, $C_2$, $C_3$, $C_4$, $C_5$, and $C_6$ aminoalkyl groups.

The term "halogen" or "halo" as used herein alone or as part of another group refers to chlorine, bromine, fluorine, and iodine, with chlorine or fluorine being preferred.

"Haloalkyl" is intended to include both branched and straight-chain saturated aliphatic hydrocarbon groups having the specified number of carbon atoms, substituted with one or more halogens. "$C_1$ to $C_6$ haloalkyl" or "$C_{1-6}$ haloalkyl" (or haloalkyl), is intended to include $C_1$, $C_2$, $C_3$, $C_4$, $C_5$, and $C_6$ haloalkyl groups. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms. The term "polyhaloalkyl" as used herein refers to an "alkyl" group as defined above which includes from 2 to 9, preferably from 2 to 5, halo substituents, such as F or Cl, preferably F, such as polyfluoroalkyl, for example, CF$_3$CH$_2$, CF$_3$ or CF$_3$CF$_2$CH$_2$.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Other examples of haloalkoxy also include "fluoroalkoxy" which represents a fluoroalkyl group as defined above with the indicated number of carbon atoms attached through an oxygen bridge. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—. The term "polyhaloalkyloxy" as used herein refers to an "alkoxy" or "alkyloxy" group as defined above which includes from 2 to 9, preferably from 2 to 5, halo substituents, such as F or Cl, preferably F, such as polyfluoroalkoxy, for example, —OCH$_2$CF$_3$, —OCF$_3$, or —OCH$_2$CF$_2$CF$_3$.

"Hydroxyalkyl" is intended to include both branched and straight-chain saturated aliphatic hydrocarbon groups having the specified number of carbon atoms, substituted with 1 or more hydroxyl (OH). "$C_1$ to $C_6$ hydroxyalkyl" (or hydroxyalkyl), is intended to include $C_1$, $C_2$, $C_3$, $C_4$, $C_5$, and $C_6$ hydroxyalkyl groups.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

The term "cycloheteroalkyl" refers to cyclized heteroalkyl groups, including mono-, bi- or poly-cyclic ring systems. "$C_3$ to $C_7$ cycloheteroalkyl" or "$C_{3-7}$ cycloheteroalkyl" is intended to include $C_3$, $C_4$, $C_5$, $C_6$, and $C_7$ cycloheteroalkyl groups. Example cycloheteroalkyl groups include, but are not limited to, oxetanyl, tetrahydrofuranyl, tetrahydropyranyl, azetidinyl, pyrrolidinyl, piperidinyl, morpholinyl, and piperazinyl. Branched cycloheteroalkyl groups, such as piperidinylmethyl, piperazinylmethyl, morpholinylmethyl, pyridinylmethyl, pyridizylmethyl, pyrimidylmethyl, and pyrazinylmethyl, are included in the definition of "cycloheteroalkyl".

As used herein, the term "azacyclyl" refers to a cycloheteroalkyl containing one or more nitrogen atoms in the ring. Example azacyclyl groups include, but are not limited to, pyrrolidinyl, piperidinyl, morpholinyl, and piperazinyl.

As used herein, "carbocycle", "carbocyclyl", or "carbocyclic" is intended to mean any stable 3-, 4-, 5-, 6-, 7-, or 8-membered monocyclic or 5-, 6-, 7-, 8-, 9-, 10-, 11-, 12-, or 13-membered polycyclic (including bicyclic or tricyclic) hydrocarbon ring, any of which may be saturated or partially unsaturated. That is, the term "carbocycle", "carbocyclyl", or "carbocyclic" includes, without limitation, cycloalkyl and cycloalkenyl. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, indanyl, adamantyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, indanyl, and tetrahydronaphthyl. A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

Furthermore, the term "carbocyclyl", including "cycloalkyl" and "cycloalkenyl", as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons or 3 to 6 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

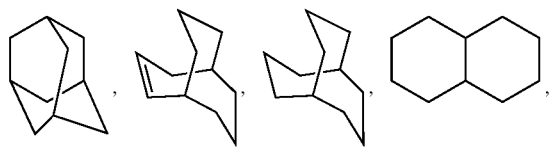

, any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated or partially unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, 1,2-dihydronaphthyl, 1,2,3,4-tetrahydronaphthyl, and indanyl.

As used herein, the term "aryl", as employed herein alone or as part of another group, refers to monocyclic or polycyclic (including bicyclic and tricyclic) aromatic hydrocarbons, including, for example, phenyl, naphthyl, anthracenyl, and phenanthranyl. Aryl moieties are well known and described, for example, in Lewis, R. J., ed., *Hawley's Condensed Chemical Dictionary*, 13th Edition, John Wiley & Sons, Inc., New York (1997). In one embodiment, the term "aryl" denotes monocyclic and bicyclic aromatic groups containing 6 to 10 carbons in the ring portion (such as phenyl or naphthyl including 1-naphthyl and 2-naphthyl). For example, "$C_6$ or $C_{10}$ aryl" or "$C_{6-10}$ aryl" refers to phenyl and naphthyl. Unless otherwise specified, "aryl", "$C_6$ or $C_{10}$ aryl", "$C_{6-10}$ aryl", or "aromatic residue" may be unsubstituted or substituted with 1 to 5 groups, preferably 1 to 3 groups, selected from —OH, —OCH$_3$, F, Cl, Br, I, —CN, —NO$_2$, —NH$_2$, —NH(CH$_3$), —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

As used herein, the term "heterocycle", "heterocyclyl", or "heterocyclic group" is intended to mean a stable 3-, 4-, 5-, 6-, or 7-membered monocyclic or 5-, 6-, 7-, 8-, 9-, 10-, 11-, 12-, 13-, or 14-membered polycyclic (including bicyclic and tricyclic) heterocyclic ring that is saturated, or partially unsaturated, and that contains carbon atoms and 1, 2, 3 or 4 heteroatoms independently selected from the group consisting of N, O and S; and including any polycyclic group in which any of the above-defined heterocyclic rings is fused to a carbocyclic or an aryl (e.g., benzene) ring. That is, the term "heterocycle", "heterocyclyl", or "heterocyclic group" includes non-aromatic ring systems, such as heterocycloalkyl and heterocycloalkenyl. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Examples of heterocyclyl include, without limitation, azetidinyl, piperazinyl, piperidinyl, piperidonyl, piperonyl, pyranyl, morpholinyl, tetrahydrofuranyl, tetrahydroisoquinolinyl, tetrahydroquinolinyl, morpholinyl, dihydrofuro[2,3-b]tetrahydrofuran.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. Examples of a bicyclic heterocyclic group are, but not limited to, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "heteroaryl" is intended to mean stable monocyclic and polycyclic (including bicyclic and tricyclic) aromatic hydrocarbons that include at least one heteroatom ring member such as sulfur, oxygen, or nitrogen. Heteroaryl groups include, without limitation, pyridinyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of heteroaryl include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathianyl, phenoxazinyl, phthalazinyl, pteridinyl, purinyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Examples of 5- to 10-membered heteroaryl include, but are not limited to, pyridinyl, furanyl, thienyl, pyrazolyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl. Examples of 5- to 6-membered heterocycles include, but are not limited to, pyridinyl, furanyl, thienyl, pyrrolyl, pyrazolyl, pyrazinyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, and triazolyl.

Unless otherwise indicated, "carbocyclyl" or "heterocyclyl" includes one to three additional rings fused to the carbocyclic ring or the heterocyclic ring (such as aryl, cycloalkyl, heteroaryl or cycloheteroalkyl rings, for example,

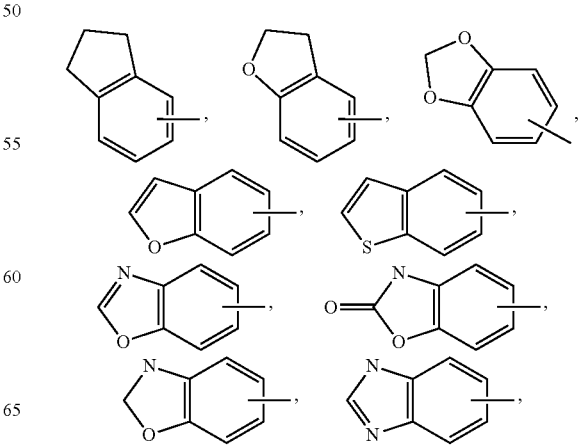

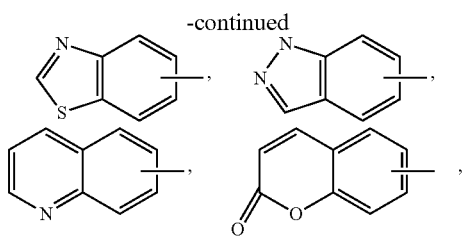

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, alkylaminocarbonyl, arylaminocarbonyl, alkoxy carbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

When any of the terms alkyl, alkenyl, alkynyl, cycloalkyl, carbocyclyl, heterocyclyl, aryl, and heteroaryl are used as part of another group, the number of carbon atoms and ring members are the same as those defined in the terms by themselves. For example, alkoxy, haloalkoxy, alkylamino, haloalkyl, hydroxy alkyl, aminoalkyl, haloalkoxy, alkoxyalkoxy, haloalkylamino, alkoxy alkylamino, haloalkoxy alkylamino, alkylthio, and the like each independently contains the number of carbon atoms which are the same as defined for the term "alkyl", such as 1 to 4 carbon atoms, 1 to 6 carbon atoms, 1 to 10 carbon atoms, etc. Similarly, cycloalkoxy, heterocyclyloxy, cycloalkylamino, heterocyclylamino, aralkylamino, arylamino, aryloxy, aralkyloxy, heteroaryloxy, heteroarylalkyloxy, and the like each independently contains ring members which are the same as defined for the terms "cycloalkyl", "heterocyclyl", "aryl", and "heteroaryl", such as 3 to 6-membered, 4 to 7-membered, 6 to 10-membered, 5 to 10-membered, 5 or 6-membered, etc.

In accordance with a convention used in the art, a bond pointing to a bold line, such as ⋎ as used in structural formulas herein, depicts the bond that is the point of attachment of the moiety or substituent to the core or backbone structure.

In accordance with a convention used in the art, a wavy or squiggly bond in a structural formula, such as

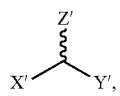

is used to depict a stereogenic center of the carbon atom to which X', Y', and Z' are attached and is intended to represent both enantiomers in a single figure. That is, a structural formula with such as wavy bond denotes each of the enantiomers individually, such as as well as a racemic mixture thereof. When a wavy or squiggly bond is attached to a double bond (such as C=C or C=N) moiety, it include cis- or trans- (or E- and Z-) geometric isomers or a mixture thereof.

It is understood herein that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the terms "pyridinyl" and "pyridyl" mean 2-, 3- or 4-pyridinyl; the term "thienyl" means 2- or 3-thienyl, and so forth.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

One skilled in the art will recognize that substituents and other moieties of the compounds of the present invention should be selected in order to provide a compound which is sufficiently stable to provide a pharmaceutically useful compound which can be formulated into an acceptably stable pharmaceutical composition. Compounds of the present invention which have such stability are contemplated as falling within the scope of the present invention.

The term "counter ion" is used to represent a negatively charged species such as chloride, bromide, hydroxide, acetate, and sulfate. The term "metal ion" refers to alkali metal ions such as sodium, potassium or lithium and alkaline earth metal ions such as magnesium and calcium, as well as zinc and aluminum.

As referred to herein, the term "substituted" means that at least one hydrogen atom (attached to carbon atom or heteroatom) is replaced with a non-hydrogen group, provided that normal valencies are maintained and that the substitution results in a stable compound. When a substituent is oxo (i.e., =O), then 2 hydrogens on the atom are replaced. Oxo substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N). The term "substituted" in reference to alkyl, cycloalkyl, heteroalkyl, cycloheteroalkyl, alkylene, aryl, arylalkyl, heteroaryl, heteroarylalkyl, carbocyclyl, and heterocyclyl, means alkyl, cycloalkyl, heteroalkyl, cycloheteroalkyl, alkylene, aryl, arylalkyl, heteroaryl, heteroarylalkyl, carbocyclyl, and heterocyclyl, respectively, in which one or more hydrogen atoms, which are attached to either carbon or heteroatom, are each independently replaced with one or more non-hydrogen substituent(s).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0, 1, 2, or 3R groups, then said group be unsubstituted when it is substituted with 0R group, or be substituted with up to three R groups, and at each occurrence R is selected independently from the definition of R.

Also, combinations of substituents and/or variables are permissible only if such combinations result in stable compounds.

As used herein, the term "tautomer" refers to each of two or more isomers of a compound that exist together in equilibrium, and are readily interchanged by migration of an atom or group within the molecule. For example, one skilled in the art would readily understand that a 1,2,3-triazole exists in two tautomeric forms as defined above:

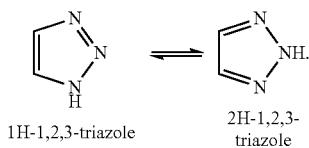

1H-1,2,3-triazole     2H-1,2,3-triazole

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

The compounds of the present invention can be present as salts, which are also within the scope of this invention. Pharmaceutically acceptable salts are preferred. As used herein, "pharmaceutically acceptable salts" refer to derivatives of the disclosed compounds wherein the parent compound is modified by making acid or base salts thereof. The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

If the compounds of the present invention have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of the present invention having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula (I) or their pharmaceutically acceptable salts, are also included.

Preferred salts of the compounds of Formula (I) which contain a basic group include monohydrochloride, hydrogensulfate, methanesulfonate, phosphate, nitrate or acetate.

Preferred salts of the compounds of Formula (I) which contain an acid group include sodium, potassium and magnesium salts and pharmaceutically acceptable organic amines.

In addition, the compounds of the present invention may have prodrug forms. Any compound that will be converted in vivo to provide the bioactive agent is a prodrug within the scope and spirit of the invention. The term "prodrug" as used herein encompasses both the prodrugs based on the carboxylic acid residue, i.e., "prodrug esters", and the prodrugs based on the arginine mimetics moiety, i.e., "prodrugs of arginine mimetics". Such prodrugs are preferably administered orally since hydrolysis in many instances occurs principally under the influence of the digestive enzymes. Parenteral administration may be used where the ester per se is active, or in those instances where hydrolysis occurs in the blood.

The compounds of the present invention contain a carboxy group which can form physiologically hydrolyzable esters that serve as prodrugs, i.e., "prodrug esters", by being hydrolyzed in the body to yield the compounds of the present invention per se. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. The "prodrug esters" can be formed by reacting the carboxylic acid moiety of the compounds of the present invention with either alkyl or aryl alcohol, halide, or sulfonate employing procedures known to those skilled in the art. Furthermore, various forms of prodrugs are well known in the art. For examples of such prodrug derivatives, see:

Bundgaard, H., ed., *Design of Prodrugs*, Elsevier (1985), and Widder, K. et al., eds., *Methods in Enzymology*, 112:309-396, Academic Press (1985);

Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

Bundgaard, H., *Adv. Drug Deliv. Rev.*, 8:1-38 (1992);

Bundgaard, H. et al., *J. Pharm. Sci.*, 77:285 (1988); and

Kakeya, N. et al., *Chem. Pharm. Bull.*, 32:692 (1984).

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999); Rautio, J. et al., *Nature Review Drug Discovery*, 17, 559-587, (2018).

The present invention is intended to include all isotopes of atoms occurring in the present compounds. Isotopes include those atoms having the same atomic number but different mass numbers. By way of general example and without limitation, isotopes of hydrogen include deuterium (symbol D or $^2$H) and tritium (symbol T or $^3$H). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

The term "solvate" means a physical association of a compound of this invention with one or more solvent molecules, whether organic or inorganic. This physical association includes hydrogen bonding. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

The term "glycosyl" means a monovalent free radical or substituent moiety obtained by removing the hemiacetal hydroxyl group from the cyclic form of a monosaccharide and, by extension, of a lower oligosaccharide. In one embodiment, the glycosyl group has the following structure:

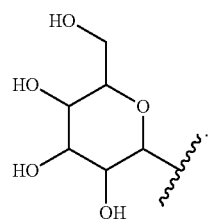

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RBF" for round bottom flask, "atm" for atmosphere, "psi" for pounds per square inch, "conc." for concentrated, "RCM" for ring-closing metathesis, "sat" or "sat'd" for saturated, "SFC" for supercritical fluid chromatography, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Abbreviations

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "m" for milliliter or milliliters, "µL" for microliter or microliters, "N" for normal, "M" for molar, "mmol" for millimole or millimoles, "min" for minute or minutes, "h" for hour or hours, "rt" for room temperature, "RBF" for round bottom flask, "atm" for atmosphere, "psi" for pounds per square inch, "conc." for concentrated, "RCM" for ring-closing metathesis, "sat" or "sat'd" for saturated, "SFC" for supercritical fluid chromatography, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Furthermore, the following abbreviations are employed in the Schemes, Examples and elsewhere herein:

Me methyl
Et ethyl
Pr propyl
i-Pr isopropyl
Bu butyl
i-Bu isobutyl
t-Bu tert-butyl
Ph phenyl
Bn benzyl
Boc or BOC tert-butyloxycarbonyl
Boc$_2$O di-tert-butyl dicarbonate
ACN acetonitrile
AcOH or HOAc acetic acid
AlCl$_3$ aluminum chloride
AIBN azobisisobutyronitrile
BBr$_3$ boron tribromide
BCl$_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz carbobenzyloxy
DCM or CH$_2$Cl$_2$ dichloromethane
CH$_3$CN or ACN acetonitrile
CDCl$_3$ deutero-chloroform
CHCl$_3$ chloroform
mCPBA or m-CPBA meta-chloroperbenzoic acid
Cs$_2$CO$_3$ cesium carbonate
Cu(OAc)$_2$ copper (II) acetate
Cy$_2$NMe N-cyclohexyl-N-methylcyclohexanamine
DBU 1,8-diazabicyclo[5.4.0]undec-7-ene
DCE 1,2 dichloroethane
DEA diethylamine
DMP or Dess-Martin 1,1,1-tris(acetyloxy)-1,1-dihydro-1,2-beniziodoxol-3-(1H)-one Periodinane
DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylpholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
Et$_3$N or TEA triethylamine
EtOAc ethyl acetate
Et$_2$O diethyl ether
EtOH ethanol
GMF glass microfiber filter
Grubbs II (1,3-bis(2,4,6-trimethylphenyl)-2-imidazolidinylidene)dichloro phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex hexanes
HOBt or HOBT 1-hydroxybenzotriazole
H$_2$O$_2$ hydrogen peroxide
IBX 2-iodoxybenzoic acid
H$_2$SO$_4$ sulfuric acid
Jones reagent CrO$_3$ in aqueous H$_2$SO$_4$, 2 M
K$_2$CO$_3$ potassium carbonate
K$_2$HPO$_4$ potassium phosphate dibasic
KOAc potassium acetate
K$_3$PO$_4$ potassium phosphate
LAH lithium aluminum hydride
LG leaving group
LiOH lithium hydroxide
MeOH methanol
MgSO$_4$ magnesium sulfate
MsCl methanesulfonyl chloride
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NCS N-chlorosuccinimide
NH$_3$ ammonia
NH$_4$Cl ammonium chloride
NH$_4$OH ammonium hydroxide
NH$_4$COOH ammonium formate
NMM N-methylmorpholine
OTf triflate or trifluoromethanesulfonate
Pd$_2$(dba)$_3$ tris(dibenzylideneacetone)dipalladium(0)
Pd(OAc)$_2$ palladium(II) acetate
Pd/C palladium on carbon
Pd(dppf)Cl$_2$ [1,1'-bis(diphenylphosphino)-ferrocene]dichloropalladium(II)
Ph$_3$PCl$_2$ triphenylphosphine dichloride
PG protecting group
POCl$_3$ phosphorus oxychloride
PPTS pyridinium p-toluenesulfonate
i-PrOH or IPA isopropanol
PS Polystyrene
PtO$_2$ platinum oxide
rt room temperature
RuPhos-Pd-G2 chloro(2-dicyclohexylphosphino-2',6'-diisopropoxy-1,1'-biphenyl)[2-(2'-amino-1,1'-biphenyl)]palladium(II)
SEM-Cl 2-(trimethysilyl)ethoxymethyl chloride
SiO$_2$ silica oxide
SnCl$_2$ tin(II) chloride
TBAI tetra-n-butylammonium iodide
TFA trifluoroacetic acid
THF tetrahydrofuran
TMSCHN$_2$ trimethylsilyldiazomethane
T3P propane phosphonic acid anhydride
TRIS tris (hydroxymethyl) aminomethane
pTsOH p-toluenesulfonic acid
TsCl p-tolunesulfonyl chloride

IV. Methods of Preparation

The compounds of the present invention can be prepared in a number of ways well known to one skilled in the art of organic synthesis using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Restrictions to the substituents that are compatible with the reaction conditions will be readily apparent to one skilled in the art and alternate methods must then be used. It will also be recognized that another major consideration in the planning of any synthetic route in this field is the judicious choice of the protecting group used for protection of the reactive functional groups present in the compounds described in this invention. A particularly useful compendium of synthetic methods which may be applicable to the preparation of compounds of the present invention may be found in Larock, R. C., *Comprehensive Organic Transformations*, VCH, New York (1989).

The compounds of the present invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula (I) falling into a given class may be compatible with some of the reaction conditions required in some of the methods described. Such restrictions to the substituents, which are compatible with the reaction conditions, will be readily apparent to one skilled in the art and alternate methods must be used. A particularly useful compendium of synthetic methods which may be applicable to the preparation of compounds of the present invention may be found in Larock, R. C., *Comprehensive Organic Transformations*, VCH, New York (1989).

Generic Schemes

Compounds of the present invention, represented by Formula (I), Formula (II), or any subgenera or species thereof, can be prepared according to the general routes shown in SCHEMES 1 to 5 below.

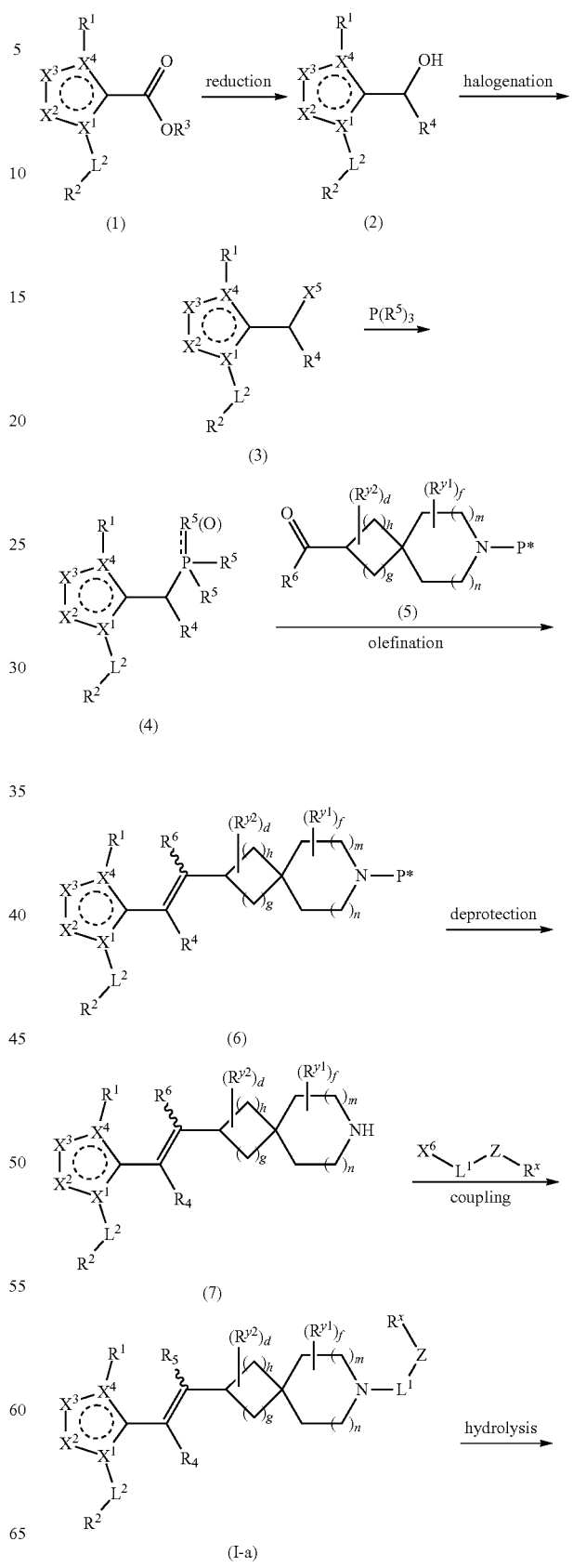

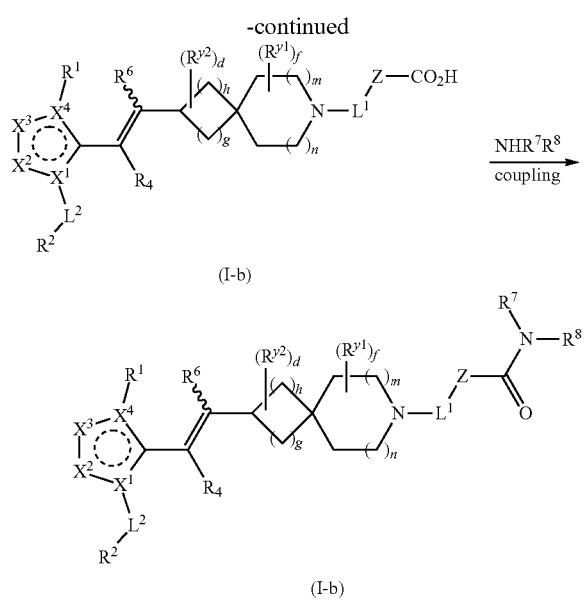

(I-b)

(I-b)

Scheme 1 describes a method of preparing compounds of Formula I-a, I-b and I-c, a subset of Formula I. Reduction of the ester intermediate 1 can be accomplished by a number of reagents including, but not limited to LiAlH$_4$, DIBAL-H, or LiBH$_4$ in an appropriate solvent such as Et$_2$O or THF to give primary alcohol intermediate 2. The resulting hydroxyl of intermediate 2 can be converted to halogenated intermediate 3 by the Appel reaction (PPh$_3$, CX$_4$) in a solvent such as, but not limited to DCM, or by heating 2 with aqueous HBr, or HCl in a solvent such as, but not limited to DCE. Intermediate 3 can be converted to the corresponding phosphonium 4 by the reaction of the halide 3 with reagents such as, but not limited to PPh$_3$ in a refluxing solvent such as toluene. Wittig olefination between phosphonium 4 and ketone or aldehyde 5 (commercially available or readily prepared by methods known to one skilled in the art) can be used to obtain an E-Z mixture of alkene 6 under conditions that include treatment of phosphonium 4 with a base such as, but not limited to, LiHMDS, LDA, NaH, KOtBu, or n-BuLi followed by addition of 5 in a suitable solvent such as THF. The olefin isomers can typically be separated by SiO$_2$ or SFC chromatography. Alternatively, heating 3 neat in a trialkoxy phosphite such as, but not limited to, triethoxy phosphite can yield the corresponding phosphonate 4. Homer-Wadsworth-Emmons (HWE) olefination can be employed to couple 4 and 5 under conditions similar to those described for Wittig olefination. The alkene 6 obtained under HWE olefination conditions typically favors formation of the E isomer and if a mixture of E-Z isomers is obtained they can be separated by SiO$_2$ or SFC chromatography. Removal of the protecting group P* can be accomplished by a variety of conditions that will vary depending on the nature of P* and on compatibility with other functional groups present in 6. In most examples P*=Boc, and appropriately acidic conditions (i.e. TFA, HCl) can be used to facilitate removal of the protecting group to give intermediate 7. However, if alternative protecting groups are required for functional group compatibility, then they can be removed by methods known to one skilled in the art. Additional methods for protecting group removal may be found in Greene, T. and Wuts, P. G. M., Protecting Groups in Organic Synthesis, John Wiley & Sons, Inc., New York, N.Y., 2006 and references therein. Intermediate 7 can be converted to products I-a through coupling with $X^6$-$L^1$-Z—R (commercially available or readily prepared by methods known to one skilled in the art, where $X^6$ represents a halide, triflate or equivalent) under conditions that are well-known to one skilled in the art. The products I-a can be obtained through a variety of C—N bond forming reactions between intermediate 7 and a suitable aryl halide, triflate or equivalent. Some examples include, but are not limited to, Pd-catalyzed Buchwald-Hartwig reaction, Cu-mediated Ullmann coupling, Ni-mediated amination, or nucleophilic aromatic substitution (SNAr). Alternatively, the Cu-catalyzed Chan-Evans-Lam coupling can be employed if $X^6$ represents a boronic acid or ester which can be commercially available or obtained by borylation of the corresponding aryl halide. In each case, optimization of variables for the coupling reaction such as catalyst, ligand, solvent, base, additives and temperature may be required. If I-a contains an ester or nitrile it can be hydrolyzed to the corresponding carboxylic acid I-b under conditions such as but not limited to treatment with NaOH or LiOH in solvents consisting of MeOH, THF, and water at a temperature suitable to enable the hydrolysis. Acid-mediated hydrolysis of particular esters, such as a tert-butyl ester, may be required in some cases to obtain I-b. Examples I-c can be obtained by the coupling of I-b with $R^7$—N—$R^8$ (commercially available or readily prepared by methods known to one skilled in the art) utilizing coupling reagents such as but not limited to, T3P, EDC, DCC or CDI in the presence of a suitable base, for example triethylamine, Hunig's base, or pyridine with or without additives such as HOBT or DMAP in an appropriate solvent such as dichloromethane, ethyl acetate, DMF or THF. In each case the specific conditions utilized to obtain I-c, including temperature and concentration, may require optimization.

SCHEME 2

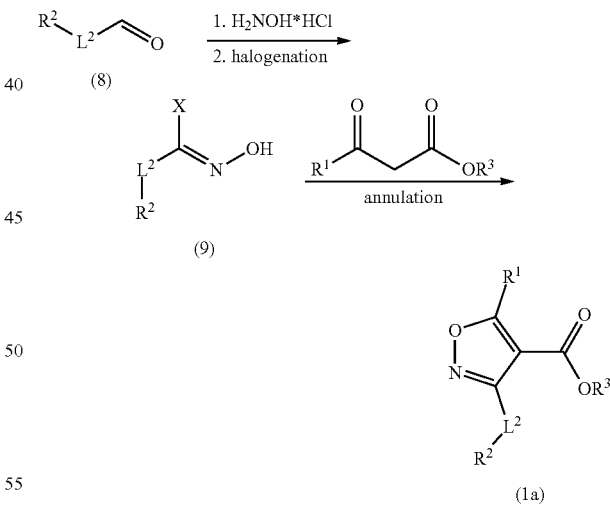

Scheme 2 describes a method for preparing intermediate 1a, a subset of intermediate 1. Aldehydes 8 (commercially available or readily prepared by methods known to one skilled in the art) can be condensed with hydroxylamine hydrochloride under a variety of conditions including, but not limited to, stirring both reactants in pyridine at room temperature, or gently heating the reactants in the presence of a base like sodium hydroxide or sodium acetate in a suitable solvent such as ethanol. The resultant oximes can be converted to the corresponding hydroximoyl halides 9 through halogenation by reagents such as but not limited to NCS or NBS in a suitable solvent such as DMF. Hydroximoyl halides 9 can be reacted with β-ketoesters (commercially available or readily prepared by methods known to one skilled in the art) in the presence of triethyl amine or another suitable base in a solvent such as, but not limited to, DCM to give 3,4,5-substituted isoxalole ester intermediate 1a.

SCHEME 3

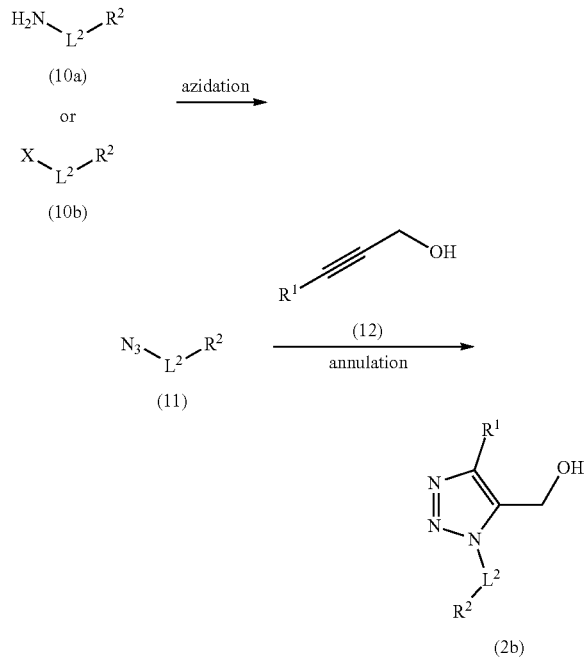

Scheme 3 describes a method for preparing intermediate 2b, a subset of intermediate 2. The synthesis can commence with azidation of amine 10a (commercially available or readily prepared by methods known to one skilled in the art) under conditions such as, but not limited to, treatment with sodium nitrite in acidic media (H₂O/TFA) followed by addition of sodium azide in an appropriate solvent, such as water at a suitable temperature to give azide 11. Alternatively, azide 11 can be obtained by the heating of halide 10b (commercially available or readily prepared by methods known to one skilled in the art) with an azide salt, such as sodium azide, in a mixture of DMSO/water at an appropriate temperature. The resultant azide 11 can undergo cyclization with an alkyne 12 by heating the reactants in a solvent such as toluene to give 2b. Alkynes 12 are commercially available, or can be obtained by a variety of methods including, but not limited to, the deprotonation of the corresponding terminal alkyne and trapping the resulting anion with formaldehyde or a formaldehyde equivalent.

SCHEME 4

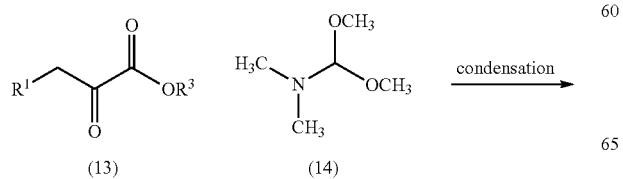

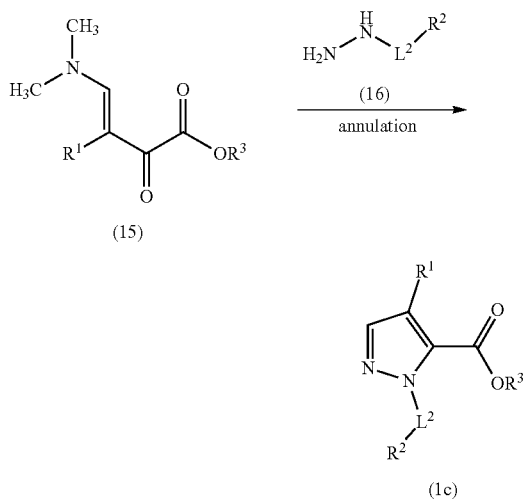

Scheme 4 describes a method for preparing intermediate 1c, a subset of intermediate 1. α-Ketoesters 13 (commercially available or readily prepared by methods known to one skilled in the art) can be condensed with N,N-dimethylformamide dimethyl acetal 14 by heating in a suitable solvent such as EtOH or MeOH to give intermediate 15. Hydrazines 16 can undergo annulation with intermediates 15 to give intermediates 1c by heating the two reactants in an appropriate solvent such as EtOH or MeOH. Hydrazines 16 are commercially available or can be prepared by the treatment of the corresponding amine with a reagent such as, but not limited to sodium nitrite in acidic media, or the coupling of the corresponding aryl halide with hydrazine.

SCHEME 5

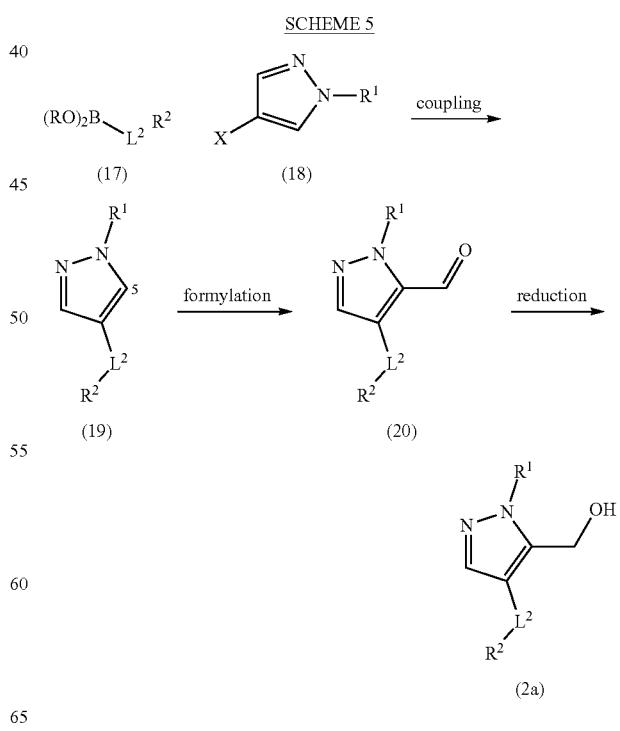

Scheme 5 describes a method for preparing intermediate 2a, a subset of intermediate 2. An appropriately substituted boronic acid or ester 17 (commercially available or readily prepared by methods known to one skilled in the art) and a pyrazole 18 bearing a suitably reactive halogen or equivalent X, (commercially available or readily prepared by methods known to one skilled in the art) can be coupled through the Pd-catalyzed Suzuki reaction to give intermediate 19. Typical conditions for the Suzuki coupling include, but are not limited to, heating the reactants 17 and 18 together with a palladium catalyst, ligand and base at a suitable temperature in a deoxygenated solvent or solvent mixture. Specific conditions include, but are not limited to $PdCl_2(dppf)_2$, $Na_2CO_3$ in THF/water at 120° C. In each case the specific conditions utilized to obtain 19, including stoichiometry, palladium source, ligand, base, solvent, temperature, and concentration may require independent optimization. Intermediate 19 can be deprotonated at the 5-position of the pyrazole by a sufficiently strong base such as, but not limited to, n-BuLi, or LDA in a suitable solvent such as THF or $Et_2O$. The resulting anion from deprotonation of 19 can be trapped in situ with a formyl equivalent such as DMF to yield aldehyde intermediate 20. Reduction of the aldehyde 20 can be accomplished by a number of reagents including, but not limited to $LiAlH_4$, DIBAL-H, or $LiBH_4$ in an appropriate solvent such as, but not limited to, THF or $Et_2O$ to give intermediate 2a.

EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

HPLC/MS and Preparatory/Analytical HPLC Methods Employed in Characterization or Purification of Examples NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. $^1$HNMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

The term HPLC refers to a Shimadzu high performance liquid chromatography instrument with one of following methods:

Examples 1 and 2

(E)-6-(6-(2-(5-Cyclopropyl-3-(3,5-dichloropyridin-4-yl)isoxazol-4-yl)vinyl)-2-azaspiro[3.3]heptan-2-yl)-4-methoxyquinoline-2-carboxylic acid (1) and (E)-6-(6-(2-(3-(3-chloropyridin-4-yl)-5-cyclopropylisoxazol-4-yl)vinyl)-2-azaspiro[3.3]heptan-2-yl)-4-methoxyquinoline-2-carboxylic acid (2)

(1)

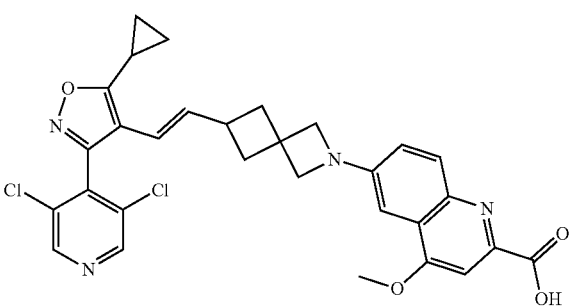

(2)

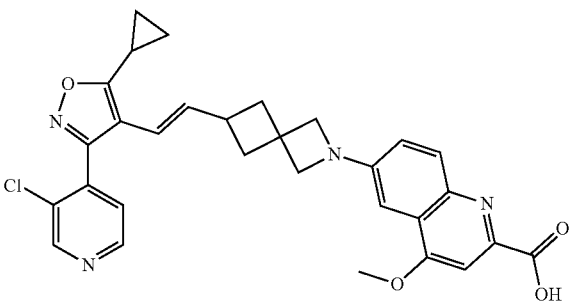

Step 1. 3,5-Dichloroisonicotinaldehyde oxime

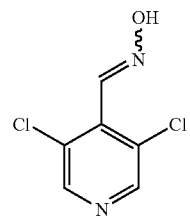

To a solution of 3,5-dichloroisonicotinaldehyde (8.0 g, 45.5 mmol) in pyridine (22.73 mL) at room temperature was added hydroxylamine hydrochloride (3.47 g, 50.0 mmol) portionwise over 3 min. The mixture was stirred at rt for 10 min, and then concentrated in vacuo to dryness to give crude 3,5-dichloroisonicotinaldehyde oxime (12.6 g) as a tan solid. MS (ESI) m/z: 190.9 (M+H)$^+$. The crude product was used in the next step without further purification.

Step 2. 3,5-Dichloro-N-hydroxyisonicotinimidoyl chloride

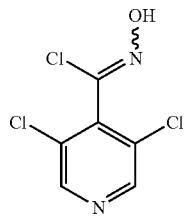

To a suspension of 3,5-dichloroisonicotinaldehyde oxime (12.6 g, <45.5 mmol) in DMF (91 mL) at rt was added NCS (6.38 g, 47.8 mmol) portionwise over 5 min. The mixture was stirred at rt for 80 min, poured onto ice, extracted with EtOAC (twice). The combined extracts were washed with brine, dried over MgSO4 and concentrated in vacuo. The oily residue was subjected to silica gel flash column, eluting with 0-40% EtOAc in hexane to afford 3,5-dichloro-N-hydroxyisonicotinimidoyl chloride (9.76 g, 43.3 mmol, 95% yield over two steps) as a white solid. MS (ESI) m/z: 226.8 (M+H)$^+$; $^1$H NMR (400 MHz, chloroform-d) (major isomer) δ 9.14 (s, 1H), 8.62 (s, 2H).

Step 3. Methyl 5-cyclopropyl-3-(3,5-dichloropyridin-4-yl)isoxazole-4-carboxylate

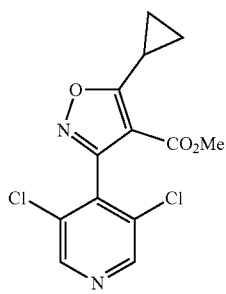 [SMILES: COC(=O)c1c(-c2c(Cl)cncc2Cl)noc1C1CC1]

To a 100 mL round bottom flask containing methyl 3-cyclopropyl-3-oxopropanoate (6.15 g, 43.3 mmol) was added Et$_3$N (12.07 mL, 87 mmol). The resulting clear solution was stirred at rt for 30 min, then cooled with ice water bath, followed by addition of a solution of 3,5-dichloro-N-hydroxyisonicotinimidoyl chloride (9.76 g, 43.3 mmol) in EtOH (19.68 mL) over 10 min. The resultant suspension was stirred at rt for 90 min and then diluted with EtOAc, washed with water, brine, dried over MgSO4, filtered, and concentrated in vacuo. The residue was loaded onto a silica gel flash column via a solid cartridge, eluting with EtOAc/hexane (0-30%) to give methyl 5-cyclopropyl-3-(3,5-dichloropyridin-4-yl)isoxazole-4-carboxylate (12.36 g, 39.6 mmol, 91% yield) as a white solid. MS (ESI) m/z: 312.9 (M+H)$^+$; $^1$H NMR (400 MHz, chloroform-d) δ 8.62 (s, 2H), 3.71 (s, 3H), 2.93 (tt, J=5.06, 8.36 Hz, 1H), 1.43 (dd, J=2.75, 4.95 Hz, 2H), 1.30-1.35 (m, 2H).

Step 4. 5-Cyclopropyl-3-(3,5-dichloropyridin-4-yl)isoxazole-4-carboxylicacid

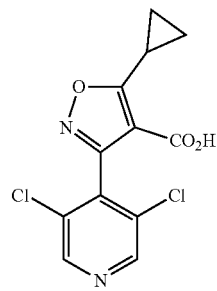 [SMILES: O=C(O)c1c(-c2c(Cl)cncc2Cl)noc1C1CC1]

A mixture of methyl 5-cyclopropyl-3-(3,5-dichloropyridin-4-yl)isoxazole-4-carboxylate (2.18 g, 6.96 mmol) and LiOH (monohydrate) (1.022 g, 24.37 mmol) in THF (7 mL), MeOH (3.5 mL) and water (3.5 mL) was stirred at rt overnight. Acetic acid (1.594 mL, 27.8 mmol) was added dropwise over 2 min and the mixture was stirred at rt for 30 min. The mixture was loaded onto a silica gel flash column via a solid cartridge, eluting with 0-20% MeOH in DCM to afford 5-cyclopropyl-3-(3,5-dichloropyridin-4-yl)isoxazole-4-carboxylic acid (2.01 g, 6.72 mmol, 97% yield) as an off-white solid. MS (ESI) m/z: 298.9 (M+H)$^+$; $^1$H NMR (400 MHz, DMSO-d6) δ 8.83 (s, 2H), 2.85-2.98 (m, 1H), 1.34 (td, J=2.89, 8.31 Hz, 2H), 1.29 (dd, J=2.64, 5.06 Hz, 2H).

Step 5. (5-Cyclopropyl-3-(3,5-dichloropyridin-4-yl)isoxazol-4-yl)methanol

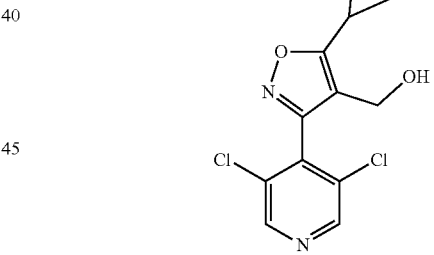

To a solution of 5-cyclopropyl-3-(3,5-dichloropyridin-4-yl)isoxazole-4-carboxylic acid (4.43 g, 14.81 mmol) in THF (10 mL) at rt was added borane tetrahydrofuran complex (1M in THF) (98 mL, 98 mmol) slowly over 30 min. The reaction was stirred at rt for 4 h. Additional borane tetrahydrofuran complex (20.74 mL, 20.74 mmol) was added and the mixture was stirred at rt for 3 days. The reaction was cooled with an ice-water bath and MeOH was added dropwise to quench the reaction until bubbling ceased. The ice-bath was removed and the mixture was stirred for 30 min. The reaction was diluted with EtOAc, washed with brine, dried over MgSO4, filtered, and concentrated under vacuum. The residue was purified by a silica gel flash column, eluted by 0-90% EtOAc/hexane to afford (5-cyclopropyl-3-(3,5-dichloropyridin-4-yl)isoxazol-4-yl) methanol (1.72 g, 6.03 mmol, 40.7% yield) as a tan solid. MS (ESI) m/z: 284.9 (M+H)$^+$; $^1$H NMR (400 MHz, chloroform-d) δ

8.60-8.65 (m, 2H), 4.46 (s, 2H), 2.18 (tt, J=5.14, 8.39 Hz, 1H), 1.29 (dd, J=1.76, 5.72 Hz, 2H), 1.18 (dd, J=2.42, 8.36 Hz, 2H).

Step 6. 4-(Bromomethyl)-5-cyclopropyl-3-(3,5-dichloropyridin-4-yl)isoxazole

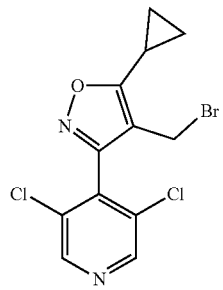 [SMILES: Clc1cncc(Cl)c1-c1noc(C2CC2)c1CBr]

To a solution of (5-cyclopropyl-3-(3,5-dichloropyridin-4-yl)isoxazol-4-yl) methanol (3.6 g, 12.63 mmol) in DCM (40 mL) was added triphenylphosphine (4.97 g, 18.94 mmol). The mixture was stirred at room temperature for 15 min, cooled to 0° C., followed by addition of a solution of CBr$_4$ (6.28 g, 18.94 mmol) in DCM (20 mL) over 10 min. The resulting mixture was stirred at rt for 2 h and then concentrated in vacuo. The residue was subjected to a silica gel flash column, eluting with 0-20% EtOAc in hexane to afford 4-(bromomethyl)-5-cyclopropyl-3-(3,5-dichloropyridin-4-yl)isoxazole (4.36 g, 12.53 mmol, 99% yield) as a white solid. MS (ESI) m/z: 348.9 (M+H)$^+$; $^1$H NMR (500 MHz, chloroform-d) δ 8.65 (s, 2H), 4.22 (s, 2H), 2.10-2.16 (m, 1H), 1.27-1.34 (m, 2H), 1.19-1.25 (m, 2H).

Step 7. Diethyl ((5-cyclopropyl-3-(3,5-dichloropyridin-4-yl)isoxazol-4-yl)methyl) phosphonate

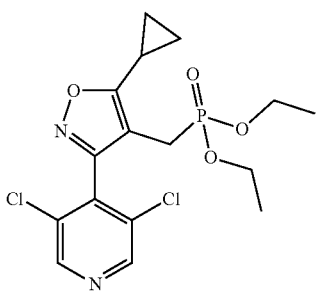 [SMILES: CCOP(=O)(Cc1c(-c2c(Cl)cncc2Cl)noc1C1CC1)OCC]

A mixture of 4-(bromomethyl)-5-cyclopropyl-3-(3,5-dichloropyridin-4-yl) isoxazole (198 mg, 0.569 mmol) and triethyl phosphite (195 µL, 1.138 mmol) was heated at 110° C. overnight. After cooling to rt, the mixture was loaded onto to a silica gel flash column and eluted with 0-100% EtOAc in hexane to afford diethyl ((5-cyclopropyl-3-(3,5-dichloropyridin-4-yl)isoxazol-4-yl)methyl)phosphonate (223 mg, 0.550 mmol, 97% yield) as an off-white solid. MS (ESI) m/z: 405.0 (M+H)$^+$; $^1$H NMR (400 MHz, chloroform-d) δ 8.65 (s, 2H), 3.91-4.07 (m, 4H), 2.80-2.97 (m, 2H), 2.16-2.24 (m, 1H), 1.23 (t, J=7.04 Hz, 10H).

Step 8. tert-Butyl (E)-6-(2-(5-cyclopropyl-3-(3,5-dichloropyridin-4-yl)isoxazol-4-yl) vinyl)-2-azaspiro[3.3]heptane-2-carboxylate

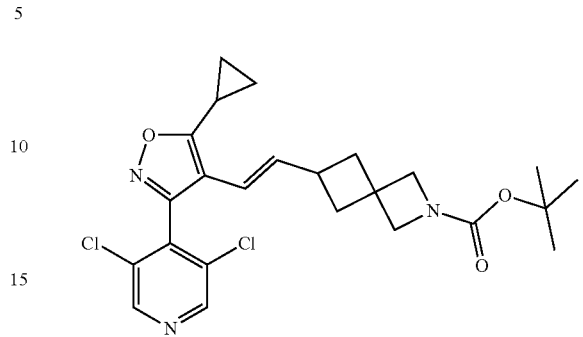

To a solution of diethyl ((5-cyclopropyl-3-(3,5-dichloropyridin-4-yl)isoxazol-4-yl)methyl)phosphonate (0.68 g, 1.678 mmol) and tert-butyl 6-formyl-2-azaspiro[3.3]heptane-2-carboxylate (0.416 g, 1.846 mmol) in THF (11.19 mL) at −78° C. was added lithium bis(trimethylsilyl)amide (1M in THF) (3.69 mL, 3.69 mmol) dropwise over 10 min. The reaction was allowed to warm up to room temperature and stirred for 3 h. The reaction mixture was filtered through a pad of silica gel and concentrated under vacuum to provide a crude oil. The crude oil was purified with a silica gel flash column, eluting with 0-40% EtOAc in hexane to afford a mixture of cis- and trans-isomers. The isomeric mixture was subjected to SFC chromatograph (Berger MG II, Column: Chiralpak IC, 21×250 mm, micron; Mobile Phase: 15% MeOH/85% CO$_2$, Flow Conditions: 45 mL/min, 120 Bar, 40° C.) to afford tert-butyl (E)-6-(2-(5-cyclopropyl-3-(3,5-dichloropyridin-4-yl)isoxazol-4-yl)vinyl)-2-azaspiro[3.3]heptane-2-carboxylate (315 mg, 0.661 mmol, 39.4% yield) as a waxy solid. MS (ESI) m/z: 476.1 (M+H)$^+$; $^1$H NMR (400 MHz, chloroform-d) δ 8.62 (s, 2H), 5.91 (dd, J=1.10, 16.07 Hz, 1H), 5.53 (dd, J=7.04, 16.07 Hz, 1H), 3.89 (s, 2H), 3.72 (s, 2H), 2.68-2.85 (m, 1H), 2.29 (ddd, J=2.53, 7.98, 10.18 Hz, 2H), 2.09 (ddd, J=3.30, 5.12, 8.31 Hz, 1H), 1.88 (br d, J=9.90 Hz, 2H), 1.41 (s, 9H), 1.19-1.27 (m, 2H), 1.08-1.18 (m, 2H).

Step 9. (E)-4-(2-(2-Azaspiro[3.3]heptan-6-yl)vinyl)-5-cyclopropyl-3-(3,5-dichloropyridin-4-yl)isoxazole

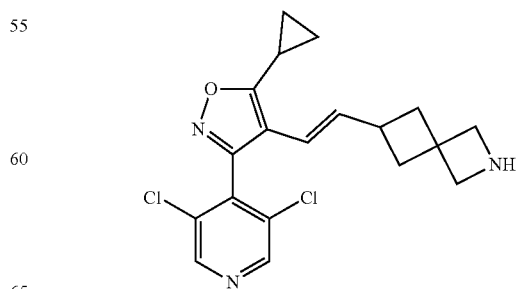

To tert-butyl(E)-6-(2-(5-cyclopropyl-3-(3,5-dichloropyridin-4-yl)isoxazol-4-yl) vinyl)-2-azaspiro[3.3]heptane-2-carboxylate (151 mg, 0.317 mmol) in DCM (0.30 mL) at 0° C. was added TFA (0.293 mL, 3.80 mmol). The reaction was stirred for 30 min and then concentrated in vacuo. The residue was dissolved EtOAc, neutralized with saturated Na$_2$CO$_3$ solution. The organic layer was separated, dried over MgSO$_4$, filtered, and concentrated in vacuo to afford (E)-4-(2-(2-azaspiro[3.3]heptan-6-yl)vinyl)-5-cyclopropyl-3-(3,5-dichloropyridin-4-yl)isoxazole (115 mg, 0.306 mmol, 96% yield) as a waxy solid. MS (ESI) m/z: 376.0 (M+H)$^+$; $^1$H NMR (400 MHz, chloroform-d) δ 8.62 (s, 2H), 5.93 (br d, J=16.07 Hz, 2H), 5.48 (dd, J=6.82, 16.07 Hz, 1H), 3.95 (s, 2H), 3.77 (s, 2H), 2.77 (br d, J=7.92 Hz, 1H), 2.34-2.44 (m, 2H), 2.05-2.13 (m, 1H), 1.84-1.99 (m, 2H), 1.21-1.27 (m, 2H), 1.12-1.19 (m, 2H).

Step 10. (E)-6-(6-(2-(5-Cyclopropyl-3-(3,5-dichloropyridin-4-yl)isoxazol-4-yl)vinyl)-2-azaspiro[3.3]heptan-2-yl)-4-methoxyquinoline-2-carboxylic acid and (E)-6-(6-(2-(3-(3-chloropyridin-4-yl)-5-cyclopropylisoxazol-4-yl)vinyl)-2-azaspiro[3.3]heptan-2-yl)-4-methoxyquinoline-2-carboxylic acid A mixture of (E)-4-(2-(2-azaspiro[3.3]heptan-6-yl)vinyl)-5-cyclopropyl-3-(3,5-dichloropyridin-4-yl)isoxazole (22 mg, 0.058 mmol), methyl 6-bromo-4-methoxyquinoline-2-carboxylate (20.78 mg, 0.070 mmol), chloro(2-dicyclohexylphosphino-2',6'-diisopropoxy-1,1'biphenyl)[2-(2'amino-1,1'-biphenyl)] palladium(II) (2.271 mg, 2.92 μmol) and Cs$_2$CO$_3$ (57.1 mg, 0.175 mmol) in dioxane (0.8 mL) was degassed and then heated at 100° C. for 4 h. Upon cooling to rt, sodium hydroxide solution (2M aq solution) (0.146 mL, 0.292 mmol) was added and the mixture was stirred at rt overnight. The mixture was filtered and subjected to prep. HPLC purification (Column: XBridge C18, 2.1×50 mm, 1.7 μm particles; Mobile Phase A: 5:95 acetonitrile: water with 0.1% trifluoroacetic acid; Mobile Phase B: 95:5 acetonitrile: water with 0.1% trifluoroacetic acid; Gradient: 0-100% B over 3 minutes, then a 0.75-minute hold at 100% B; Flow: 1 mL/min) to afford (E)-6-(6-(2-(5-cyclopropyl-3-(3,5-dichloropyridin-4-yl)isoxazol-4-yl)vinyl)-2-azaspiro[3.3]heptan-2-yl)-4-methoxyquinoline-2-carboxylic acid (6.1 mg, 7.49 μmol, 12.8% yield) and (E)-6-(6-(2-(3-(3-chloropyridin-4-yl)-5-cyclopropylisoxazol-4-yl)vinyl)-2-azaspiro[3.3]heptan-2-yl)-4-methoxyquinoline-2-carboxylic acid as their TFA salts. MS (ESI) m/z: 577.3 (M+H)$^+$; $^1$H NMR (500 MHz, DMSO-d6) δ 8.87 (s, 2H), 7.93 (br s, 1H), 7.45 (br s, 1H), 7.05 (br s, 1H), 6.73 (br s, 1H), 6.11 (br d, J=16.07 Hz, 1H), 5.60 (br dd, J=7.07, 16.07 Hz, 1H), 4.07 (s, 3H), 3.97 (br s, 2H), 3.69-3.88 (m, 2H), 2.82-2.93 (m, 1H), 2.32-2.43 (m, 3H), 1.93 (br d, J=9.26 Hz, 2H), 1.17-1.22 (m, 2H), 1.06-1.13 (m, 2H). MS (ESI) m/z: 543.3 [M+H]+; EC$_{50}$ values for Examples 1 and 2 are 155 nM and 501 nM, respectively; $^1$H NMR (500 MHz, DMSO-d6) distinguishable chemical shift δ 8.87 (s, 1H), 8.72 (br d, J=4.88 Hz, 1H), 7.87-7.99 (m, 1H), 7.59 (d, J=4.88 Hz, 1H), 7.47 (s, 1H), 6.98 (br d, J=8.24 Hz, 1H), 6.71 (br s, 1H), 6.03-6.19 (m, 1H), 5.66 (br d, J=7.63 Hz, 1H), 4.02 (s, 3H), 3.93 (s, 2H), 3.73 (s, 2H), 2.81-2.93 (m, 1H), 2.33-2.40 (m, 2H), 1.95 (br s, 1H), 1.13-1.20 (m, 2H), 1.08 (br d, J=2.75 Hz, 2H).

Example 3

(E)-4-Cyclobutoxy-6-(6-(2-(5-cyclopropyl-3-(2-(trifluoromethyl)pyridin-3-yl)isoxazol-4-yl)vinyl)-2-azaspiro[3.3]heptan-2-yl)quinoline-2-carboxylic acid

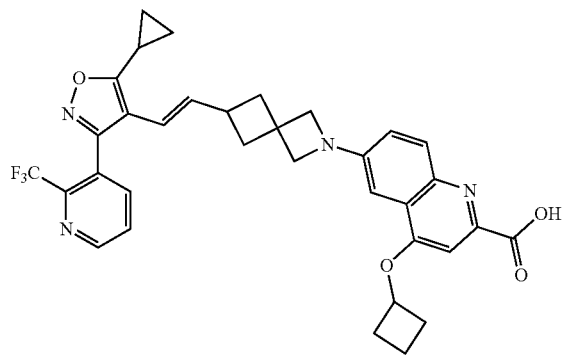

(3)

Step 1. 2-(Trifluoromethyl)nicotinaldehyde oxime

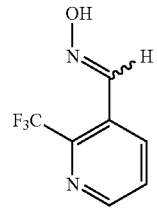

A solution of 2-(trifluoromethyl)nicotinaldehyde (1.96 g, 11.19 mmol) and hydroxylamine hydrochloride (0.856 g, 12.31 mmol) in pyridine (6 mL) was stirred at rt for 1 h. Pyridine was removed under vacuum to give the desired product (2.12 g, 100%) as a white solid: LCMS (ES): m/z 191.0 [M+H]$^+$.

Step 2. 2-Chloro-2-(2-(trifluoromethyl)pyridin-3-yl)ethen-1-ol

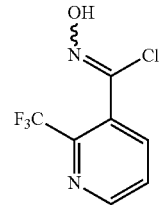

2-(Trifluoromethyl)nicotinaldehyde oxime (2.12 g, 11.15 mmol) was dissolved in DMF (20 mL) and 1-chloropyrrolidine-2,5-dione (2.0 g, 14.98 mmol) was added. The mixture was stirred at rt for 16 h. After evaporation of the solvent, the crude product was diluted with H$_2$O (50 mL) and extracted with dichloromethane (4×60 mL). The organic layers were combined, dried over MgSO4, filtered, and concentrated under vacuum to give a crude product, which was purified by flash chromatography (silica gel, hexanes:EtOAc, 100:0 to 15:85) to afford 2.21 g (88% yield) of the desired product as a white solid: ¹H NMR (400 MHz, DMSO-d6) (the major isomer) δ 12.82 (s, 1H), 8.88 (dd, J=4.6, 1.5 Hz, 1H), 8.26 (dd, J=8.0, 1.5 Hz, 1H), 7.88 (dd, J=8.0, 4.6 Hz, 1H). LCMS (ES): m/z 224.9 [M+H]⁺.

Step 3. Methyl 5-cyclopropyl-3-(2-(trifluoromethyl) pyridin-3-yl)isoxazole-4-carboxylate

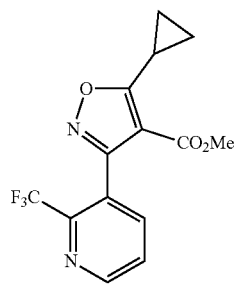 [SMILES: COC(=O)c1c(-c2cccnc2C(F)(F)F)noc1C1CC1]

A mixture of methyl 3-cyclopropyl-3-oxopropanoate (1.616 g, 11.37 mmol) and triethylamine (2.76 mL, 19.77 mmol) was stirred at rt for 25 min and then cooled to 0° C. A solution of 2-chloro-2-(2-(trifluoromethyl)pyridin-3-yl) ethen-1-ol (2.21 g, 9.88 mmol) in ethanol (25 mL) was added over 10 min. The mixture was stirred at room temperature for 16 h and then concentrated under vacuum. The residue was diluted with EtOAc (150 mL), washed saturated NaHCO₃ solution (20 mL) and brine, dried over anhydrous MgSO4, and concentrated under vacuum. The residue was purified by flash chromatography (silica gel, hexanes:EtOAc, 100:0 to 60:40) to afford 1.85 g (59.9% yield) of the desired product as a white solid: ¹H NMR (400 MHz, chloroform-d) δ 8.83 (dd, J=4.6, 1.8 Hz, 1H), 7.78 (dd, J=7.9, 1.5 Hz, 1H), 7.58 (dd, J=7.9, 4.6 Hz, 1H), 3.65 (s, 3H), 3.01-2.72 (m, 1H), 1.45-1.22 (m, 4H). LCMS (ES): m/z 313.0 [M+H]⁺.

Step 4. (5-Cyclopropyl-3-(2-(trifluoromethyl)pyridin-3-yl)isoxazol-4-yl)methanol

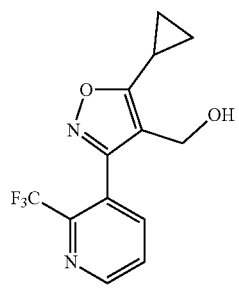 [SMILES: OCc1c(-c2cccnc2C(F)(F)F)noc1C1CC1]

DIBAL-H solution (23.7 mL, 23.70 mmol, 1M in toluene) was added dropwise to a stirring solution of methyl 5-cyclopropyl-3-(2-(trifluoromethyl)pyridin-3-yl)isoxazole-4-carboxylate (1.85 g, 5.92 mmol) in THF (20 mL) at 0° C. After addition, the reaction mixture was stirred at 0° C. for 15 min and then allowed to warm to room temperature over 45 min. Ethyl acetate (210 mL) was added. The reaction mixture was cooled to 0° C. and quenched with 6 mL aqueous saturated Rochelles' salt solution. The resulting mixture was stirred at rt for 0.5 h. The organic layer was separated and the aqueous residue was extracted with EtOAc (2×20 mL). The combined extracts were washed with brine, dried over anhydrous Na₂SO₄, filtered, and concentrated. The residue was purified by flash chromatography (silica gel, hexanes:EtOAc, 100:0 to 20:80) to afford 1.29 g (77% yield) of the desired product as a white solid: ¹H NMR (400 MHz, chloroform-d) δ 8.96-8.74 (m, 1H), 7.89 (ddd, J=7.9, 1.6, 0.7 Hz, 1H), 7.60 (dd, J=7.9, 4.7 Hz, 1H), 4.45 (d, J=4.9 Hz, 2H), 2.24-2.04 (m, 1H), 1.36-1.04 (m, 4H). LCMS (ES): m/z 285.0 [M+H]⁺.

Step 5. 4-(Bromomethyl)-5-cyclopropyl-3-(2-(trifluoromethyl)pyridin-3-yl)isoxazole

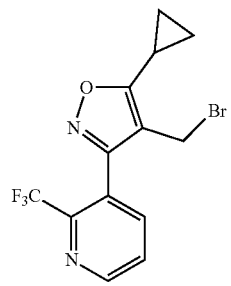 [SMILES: FC(F)(F)c1ncccc1-c1noc(C2CC2)c1CBr]

To a solution of (5-cyclopropyl-3-(2-(trifluoromethyl) pyridin-3-yl)isoxazol-4-yl) methanol (1.29 g, 4.54 mmol) in DCM (16.5 mL) was added triphenylphosphine (2.14 g, 8.17 mmol). The mixture was stirred at rt for 15 min and then cooled to 0° C. before a solution of CBr₄ (2.71 g, 8.17 mmol) in DCM (16.5 mL) was added over 5 min. The resulting mixture was allowed to warm to rt and stirred for 2 h. After evaporation of the solvent, the crude product was purified by flash chromatography (silica gel, hexanes:EtOAc, 100:0 to 60:40) to afford 1.4 g (89% yield) of the desired product as a white solid: LCMS (ES): m/z 348.9 [M+H]⁺.

Step 6. Diethyl((5-cyclopropyl-3-(2-(trifluoromethyl) pyridin-3-yl)isoxazol-4-yl)methyl) phosphonate

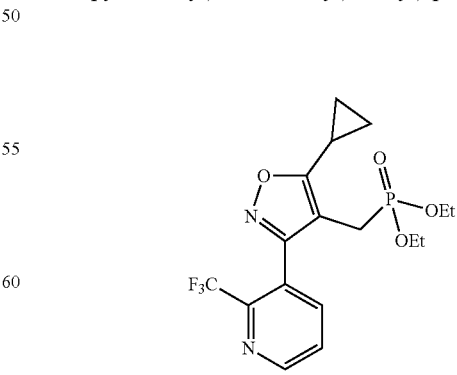

A solution of 4-(bromomethyl)-5-cyclopropyl-3-(2-(trifluoromethyl)pyridin-3-yl)isoxazole (Intermediate 6, 1.4 g, 4.03 mmol) and triethyl phosphite (1.383 mL, 8.07 mmol) in dioxane (2.9 mL) was heated at 120° C. in a sealed vial for 3 h. The volatiles were evaporated. The residue was purified by flash chromatography (silica gel, hexanes:EtOAc, 100:0 to 0:100) to afford 1.61 g (99% yield) of the desired product as a white solid: $^1$H NMR (400 MHz, chloroform-d) δ 8.82 (dd, J=4.7, 1.6 Hz, 1H), 8.04 (dd, J=7.9, 1.6 Hz, 1H), 7.61 (dd, J=7.9, 4.7 Hz, 1H), 4.10-3.90 (m, 4H), 2.80 (d, J=20.1 Hz, 2H), 2.27-2.09 (m, 1H), 1.30-1.20 (m, 8H), 1.17-1.09 (m, 2H). LCMS (ES): m/z 405.1 [M+H]$^+$.

Step 7. tert-Butyl (E)-6-(2-(5-cyclopropyl-3-(2-(trifluoromethyl)pyridin-3-yl)isoxazol-4-yl)vinyl)-2-azaspiro[3.3]heptane-2-carboxylate

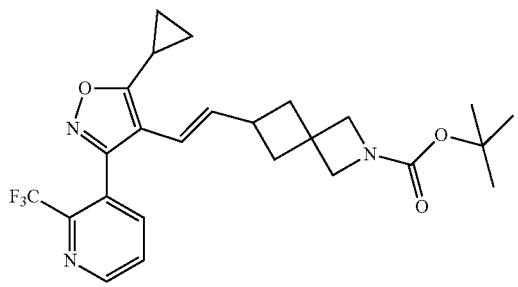 [SMILES: CC(C)(C)OC(=O)N1CC2(CC(/C=C/c3c(-c4cccnc4C(F)(F)F)noc3C3CC3)C2)C1]

To a solution of diethyl ((5-cyclopropyl-3-(2-(trifluoromethyl)pyridin-3-yl)isoxazol-4-yl)methyl)phosphonate (332 mg, 0.821 mmol) in THF (4.8 mL) at −78° C. was added lithium bis(trimethylsilyl)amide (1.806 mL, 1.806 mmol, 1M in THF) dropwise. The reaction was stirred at −78° C. for 30 min. Then a solution of tert-butyl 6-formyl-2-azaspiro[3.3]heptane-2-carboxylate (200 mg, 0.888 mmol) in THF (1.9 mL) was added. The reaction mixture was allowed to warm to room temperature and stirred for 6.5 h. The reaction was quenched with saturated NH$_4$Cl solution (1 mL). The mixture was concentrated under vacuum. The residue was diluted with EtOAc (30 mL), washed with H$_2$O (8 mL) and brine, dried over anhydrous MgSO4, filtered, and concentrated under vacuum. The residue was purified by flash chromatography (silica gel, hexanes:EtOAc, 100:0 to 20:80) to afford 260 mg (67% yield) of the mixture of E and Z isomers as a colorless oil: LCMS (ES): m/z 476.2 [M+H]$^+$.

The Z and E isomers were separated by SFC method (Instrument: Berger MG II (CTR-L409-PSFC1); Column: Chiralpak IC, 21×250 mm, 5 micron; Mobile Phase 30% MeOH/70% CO$_2$; Flow: 45 mL/min, 150 Bar, 40° C.) to afford tert-Butyl (E)-6-(2-(5-cyclopropyl-3-(2-(trifluoromethyl)pyridin-3-yl)isoxazol-4-yl)vinyl)-2-azaspiro[3.3]heptane-2-carboxylate (150 mg) as a yellow oil. $^1$H NMR (400 MHz, chloroform-d) δ 8.88 (dd, J=4.7, 1.6 Hz, 1H), 7.80 (dd, J=7.7, 1.6 Hz, 1H), 7.63 (dd, J=7.8, 4.7 Hz, 1H), 5.91 (dd, J=16.1, 1.3 Hz, 1H), 5.53 (dd, J=16.1, 7.1 Hz, 1H), 3.92 (s, 2H), 3.73 (s, 2H), 2.78 (h, J=7.8 Hz, 1H), 2.39-2.21 (m, 2H), 2.15-2.05 (m, 1H), 1.97-1.78 (m, 2H), 1.44 (s, 9H), 1.34-1.07 (m, 4H). LCMS (ES): m/z 476.2 [M+H]$^+$.

Step 8. (E)-4-(2-(2-Azaspiro[3.3]heptan-6-yl)vinyl)-5-cyclopropyl-3-(2-(trifluoromethyl)pyridin-3-yl)isoxazole

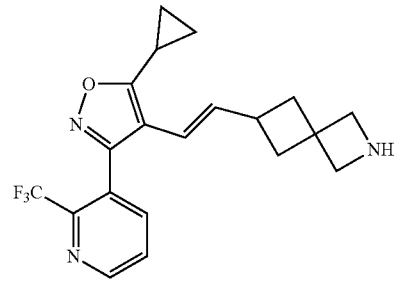 [SMILES: FC(F)(F)c1ncccc1-c1noc(C2CC2)c1/C=C/C1CC2(CNC2)C1]

To a mixture of tert-butyl (E)-6-(2-(5-cyclopropyl-3-(2-(trifluoromethyl)pyridin-3-yl)isoxazol-4-yl)vinyl)-2-azaspiro[3.3]heptane-2-carboxylate (150 mg, 0.315 mmol) in DCM (0.292 mL) was added TFA (0.292 mL, 3.79 mmol). The reaction mixture was stirred at rt for 1 h. The solvent was evaporated to give the crude product as viscous oil. The crude product was diluted with CHCl$_3$ (10 mL) and washed with sodium hydroxide solution (2 mL, 1N aqueous solution). The organic layer was separated, dried over anhydrous MgSO4, filtered, and concentrated under vacuum to afford 118 mg (100% yield) of the desired product as a light brown foam. LCMS (ES): m/z 376.1 [M+H]$^+$.

Step 9. Methyl (E)-4-cyclobutoxy-6-(6-(2-(5-cyclopropyl-3-(2-(trifluoromethyl)pyridin-3-yl)isoxazol-4-yl)vinyl)-2-azaspiro[3.3]heptan-2-yl)quinoline-2-carboxylate

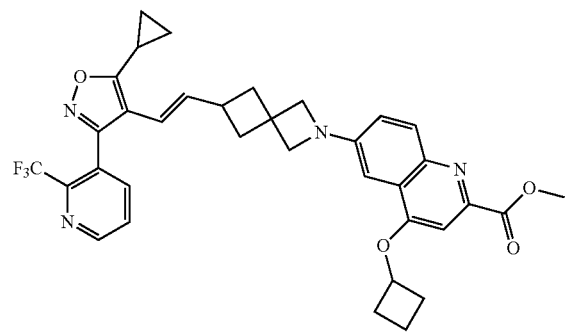 [SMILES: COC(=O)c1cc(OC2CCC2)c2cc(N3CC4(CC(/C=C/c5c(-c6cccnc6C(F)(F)F)noc5C5CC5)C4)C3)ccc2n1]

A mixture of (E)-4-(2-(2-azaspiro[3.3]heptan-6-yl)vinyl)-5-cyclopropyl-3-(2-(trifluoromethyl)pyridin-3-yl)isoxazole (29 mg, 0.070 mmol), methyl 6-bromo-4-cyclobutoxyquinoline-2-carboxylate (30 mg, 0.089 mmol), chloro(2-dicyclohexylphosphino-2',6'-diisopropoxy-1,1'biphenyl)[2-(2'amino-1,1'-biphenyl)]palladium(II) (8.20 mg, 10.56 µmol) and Cs$_2$CO$_3$ (87 mg, 0.268 mmol) in dioxane (1.1 mL) was degassed and then heated at 105° C. in a sealed vial for 1.5 h. The reaction was filtered through a pad of Celite and washed with DCM (3 mL). The filtrate was concentrated to give a crude product which was further purified by flash chromatography (silica gel, hexanes:EtOAc, 100:0 to 0:100) to afford 34 mg (75% yield) of the desired product as a yellow foam. $^1$H NMR (400 MHz, chloroform-d) δ 8.91 (dd, J=4.8, 1.6 Hz, 1H), 8.05 (d, J=9.1 Hz, 1H), 7.83 (dd, J=7.8, 1.6 Hz, 1H), 7.66 (dd, J=7.8, 4.7 Hz, 1H), 7.35 (s, 1H), 6.97 (dd, J=9.1, 2.7 Hz, 1H), 6.85 (d, J=2.6 Hz, 1H), 5.96 (dd, J=16.1, 1.3 Hz, 1H), 5.59 (dd, J=16.1, 7.1 Hz, 1H), 4.97 (p, J=7.1 Hz, 1H), 4.06 (s, 2H), 4.05 (s, 3H), 3.86 (s, 2H), 2.94-2.80 (m, 1H), 2.71-2.57 (m, 2H), 2.46-2.37 (m, 2H), 2.36-2.27 (m, 2H), 2.17-2.08 (m, 1H), 2.04-1.94 (m, 3H), 1.90-1.75 (m, 1H), 1.32-1.13 (m, 4H). LCMS (ES): m/z 631.4 [M+H]$^+$.

Step 10. (E)-4-Cyclobutoxy-6-(6-(2-(5-cyclopropyl-3-(2-(trifluoromethyl)pyridin-3-yl) isoxazol-4-yl) vinyl)-2-azaspiro[3.3]heptan-2-yl)quinoline-2-carboxylic acid A solution of (methyl (E)-4-cyclobutoxy-6-(6-(2-(5-cyclopropyl-3-(2-(trifluoromethyl)pyridin-3-yl)isoxazol-4-yl)vinyl)-2-azaspiro[3.3]heptan-2-yl)quinoline-2-carboxylate (34 mg, 0.054 mmol) and sodium hydroxide (0.15 mL, 0.150 mmol, 1M aqueous) in methanol (0.9 mL) and tetrahydrofuran (0.3 mL) was heated at 60° C. for 2 h. The volatiles were removed in vacuo and the residue was purified by preparative HPLC (Column: Sunfire C18 OBD, 30×100 mm, 5-µm particles; Mobile Phase A: 5:95 acetonitrile:water with 0.1% TFA; Mobile Phase B: 95:5 acetonitrile:water with 0.1% TFA; Gradient: 55-100% B over 10 minutes, then a 5-minute hold at 100% B; Flow: 40 mL/min) to afford 25.5 mg (62% yield) of the desired product (TFA salt) as orange solid: LCMS (ES): m/z 617.4 [M+H]$^+$; EC$_{50}$=86 nM; $^1$H NMR (400 MHz, DMSO-d6) δ 8.99 (dd, J=4.8, 1.5 Hz, 1H), 8.13 (dd, J=8.0, 1.5 Hz, 1H), 8.04-7.97 (m, 1H), 7.94 (dd, J=7.9, 4.7 Hz, 1H), 7.34-7.20 (m, 1H), 7.22-7.08 (m, 1H), 6.74 (d, J=2.6 Hz, 1H), 6.11 (dd, J=16.2, 1.3 Hz, 1H), 5.53 (dd, J=16.1, 7.5 Hz, 1H), 5.21-5.08 (m, 1H), 4.01 (s, 2H), 3.79 (s, 2H), 2.92-2.78 (m, 1H), 2.64-2.47 (m, 2H), 2.42-2.32 (m, 3H), 2.31-2.19 (m, 2H), 2.02-1.86 (m, 3H), 1.84-1.70 (m, 1H), 1.30-1.02 (m, 4H).

Intermediate 1

Methyl (R)-6-bromo-4-((tetrahydrofuran-3-yl)oxy)quinoline-2-carboxylate

Step 1. (S)-Tetrahydrofuran-3-yl 4-methylbenzenesulfonate

To a mixture of (S)-tetrahydrofuran-3-ol (1 g, 11.35 mmol) and pyridine (1.836 mL, 22.70 mmol) in CH$_2$Cl$_2$ (20 mL) at rt was added p-toluenesulfonyl chloride (3.3 g, 17.31 mmol). The reaction mixture was stirred at rt for 2 h. After evaporation of the solvent, the crude product was diluted with EtOAc (50 mL), washed with water, and then 1 N HCl. The organic layer was dried over anhydrous MgSO4, filtered, and concentrated under vacuum. The residue was purified by flash chromatography (silica gel, hexanes:EtOAc, 100:0 to 50:50) to afford (S)-tetrahydrofuran-3-yl 4-methylbenzenesulfonate (1.9 g, 69% yield) as colorless oil: $^1$H NMR (400 MHz, chloroform-d) δ 7.81 (d, J=8.1 Hz, 2H), 7.37 (d, J=8.1 Hz, 2H), 5.14 (tt, J=4.8, 2.5 Hz, 1H), 3.99-3.75 (m, 4H), 2.48 (s, 3H), 2.17-2.05 (m, 2H). MS (ESI): m/z 243.1 [M+H]$^+$.

Step 2. Methyl (R)-6-bromo-4-((tetrahydrofuran-3-yl)oxy)quinoline-2-carboxylate

A mixture of methyl 6-bromo-4-hydroxyquinoline-2-carboxylate (208 mg, 0.737 mmol), (S)-tetrahydrofuran-3-yl 4-methylbenzenesulfonate (357 mg, 1.475 mmol) and K$_2$CO$_3$ (306 mg, 2.212 mmol) in acetonitrile (3 mL) was heated at 110° C. in a sealed vial for 4 h. The reaction mixture was diluted with CH$_2$Cl$_2$ (10 mL) and filtered through Celite. The filtrate was concentrated to give a crude product which was purified by flash chromatography (silica gel, hexanes:EtOAc, 100:0 to 0:100) to afford methyl (R)-6-bromo-4-((tetrahydrofuran-3-yl)oxy)quinoline-2-carboxylate (190 mg, 73% yield) as white solid: $^1$H NMR (400 MHz, chloroform-d) δ 8.38 (d, J=2.3 Hz, 1H), 8.09 (d, J=9.0 Hz, 1H), 7.84 (dd, J=9.0, 2.2 Hz, 1H), 7.52 (s, 1H), 5.34-5.25 (m, 1H), 4.20-4.14 (m, 2H), 4.14-3.95 (m, 2H), 4.08 (s, 3H), 2.56-2.17 (m, 2H). MS (ESI): m/z 352.0 [M+H]$^+$.

Intermediate 2

Methyl (S)-6-bromo-4-((tetrahydrofuran-3-yl)oxy)quinoline-2-carboxylate

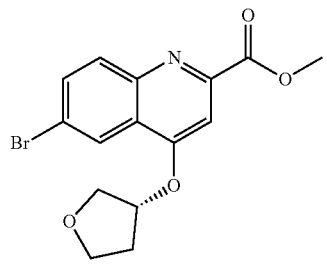 [SMILES: COC(=O)c1cc(O[C@@H]2CCOC2)c2cc(Br)ccc2n1]

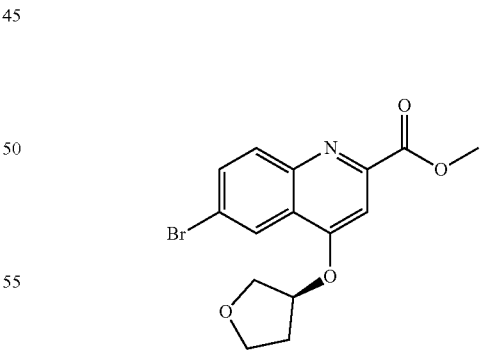

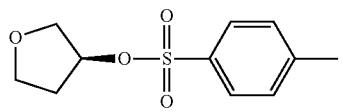

Methyl (S)-6-bromo-4-((tetrahydrofuran-3-yl)oxy)quinoline-2-carboxylate was obtained by following the same procedures for intermediate 1 using commercially available (R)-tetrahydrofuran-3-ol: $^1$H NMR (400 MHz, chloroform-d) δ 8.38 (d, J=2.2 Hz, 1H), 8.09 (d, J=9.0 Hz, 1H), 7.84 (dd, J=9.0, 2.2 Hz, 1H), 7.52 (s, 1H), 5.32-5.25 (m, 1H), 4.19-4.14 (m, 2H), 4.13-3.93 (m, 2H), 4.08 (s, 3H), 2.52-2.22 (m, 2H). MS (ESI): m/z 352.0 [M+H]$^+$.

Intermediate 3

Methyl 6-bromo-4-(oxetan-3-yloxy)quinoline-2-carboxylate

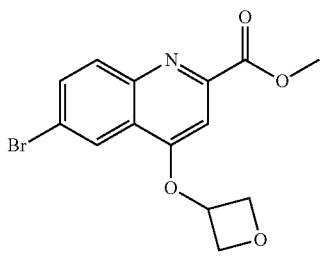 [SMILES: COC(=O)c1cc(OC2COC2)c2cc(Br)ccc2n1]

A mixture of methyl 6-bromo-4-hydroxyquinoline-2-carboxylate (439 mg, 1.56 mmol), 3-iodooxetane (526 mg, 2.86 mmol) and $K_2CO_3$ (645 mg, 4.67 mmol) in DMF (8 mL) was heated at 85° C. in a sealed vial for 6 h. Another portion of 3-iodooxetane (200 mg, 1.08 mmol) and $K_2CO_3$ (100 mg, 0.72 mmol) were added. The reaction mixture was heated at 85° C. in a sealed vial for another 16 h. The reaction mixture was diluted with $CH_2Cl_2$ (20 mL) and filtered through Celite. The filtrate was concentrated to give a crude product which was purified by flash chromatography (silica gel, hexanes:EtOAc, 100:0 to 20:80) to afford methyl 6-bromo-4-(oxetan-3-yloxy)quinoline-2-carboxylate (287 mg, 54% yield) as white solid: $^1$H NMR (400 MHz, chloroform-d) δ 8.45 (d, J=2.2 Hz, 1H), 8.11 (d, J=9.0 Hz, 1H), 7.87 (dd, J=9.0, 2.3 Hz, 1H), 7.16 (s, 1H), 5.54 (tt, J=6.0, 4.9 Hz, 1H), 5.15 (ddd, J=7.2, 6.0, 1.0 Hz, 2H), 4.90 (ddd, J=7.6, 5.0, 1.0 Hz, 2H), 4.07 (s, 3H). MS (ESI): m/z 340.0 [M+H]$^+$.

Intermediate 4

Methyl 7-chloro-1-methylisoquinoline-3-carboxylate

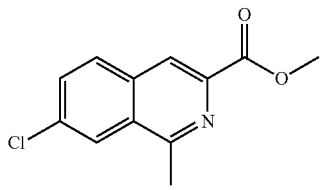 [SMILES: COC(=O)c1cc2ccc(Cl)cc2c(C)n1]

Step 1. Methyl (R)-7-chloro-1-methyl-3,4-dihydroisoquinoline-3-carboxylate

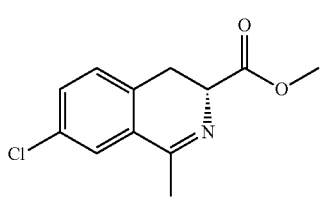 [SMILES: COC(=O)[C@H]1Cc2ccc(Cl)cc2C(C)=N1]

To a solution of methyl (R)-2-acetamido-3-(4-chlorophenyl)propanoate (0.606 g, 2.370 mmol) in DCM (15.80 mL) at 0° C. was added oxalyl dichloride (1.422 mL, 2.84 mmol) dropwise over 3 min. The mixture was stirred at 0° C. for one hour and then at rt for another hour. The reaction was cooled back to 0° C. and iron(III) chloride (0.461 g, 2.84 mmol) was added. The mixture was allowed to warm up to rt, stirred at rt for 1.5 h, filtered through a pad of $SiO_2$ gel, and concentrated under vacuum. The oily residue was purified by a silica gel flash column, eluting with 0-60% EtOAc in hexane to give methyl (R)-7-chloro-1-methyl-3,4-dihydroisoquinoline-3-carboxylate (0.616 g, 1.996 mmol, 84% yield) as an oil. MS (ESI) m/z: 238.0 (M+H)$^+$.

Step 2. Methyl 7-chloro-1-methylisoquinoline-3-carboxylate

A mixture of methyl (R)-7-chloro-1-methyl-3,4-dihydroisoquinoline-3-carboxylate (0.60 g, 1.944 mmol) and 10% Pd—C (0.621 g, 0.583 mmol) in DCE (4.86 mL) in a sealed tube was heated at 110° C. for 4 h. The reaction mixture was loaded onto a silica gel flash column via a solid cartridge and eluted with 0-50% EtOAc/hexane to give methyl 7-chloro-1-methylisoquinoline-3-carboxylate (110 mg, 0.467 mmol, 24.01% yield) as a tan solid. MS (ESI) m/z: 236.0 (M+H)$^+$; $^1$H NMR (400 MHz, chloroform-d) δ 8.44 (s, 1H), 8.16-8.19 (m, 1H), 7.92 (d, J=8.58 Hz, 1H), 7.72 (dd, J=1.98, 8.80 Hz, 1H), 4.06 (s, 3H), 3.03 (s, 3H).

Intermediate 5

Ethyl 7-bromo-1-methoxyisoquinoline-3-carboxylate

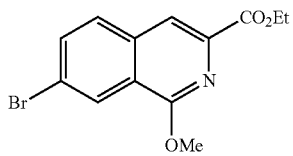 [SMILES: CCOC(=O)c1cc2ccc(Br)cc2c(OC)n1]

Step 1. 7-Bromo-3-(ethoxycarbonyl)isoquinoline 2-oxide

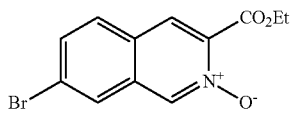 [SMILES: CCOC(=O)c1cc2ccc(Br)cc2c[n+]1[O-]]

To a solution of ethyl 7-bromoisoquinoline-3-carboxylate (456 mg, 1.628 mmol) in dichloromethane (10 mL) at 0° C. was added 3-chlorobenzoperoxoic acid (547 mg, 2.442 mmol) in one portion. The resulting solution was stirred at rt for 22 h, then quenched with saturated $NaHCO_3$ solution (20 mL), and extracted with dichloromethane (3×40 mL). The combined extracts were dried over anhydrous $Na_2SO_4$, filtered, and concentrated under vacuum. The residue was purified by flash chromatograph (24 g silica gel, solid loading, 60-95% ethyl acetate/hexane) to provide 7-bromo-3-(ethoxycarbonyl) isoquinoline 2-oxide (340 mg, 1.148 mmol, 70.5% yield) as a white solid.

Step 2. Ethyl 7-bromo-1-chloroisoquinoline-3-carboxylate

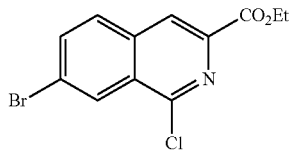 [SMILES: CCOC(=O)c1cc2ccc(Br)cc2c(Cl)n1]

A mixture of 7-bromo-3-(ethoxycarbonyl)isoquinoline 2-oxide (190 mg, 0.642 mmol) and phosphoryl trichloride (4 mL, 42.9 mmol) was heated at 100° C. for 3 h and then concentrated under vacuum to dryness. The residue was purified by prep. HPLC (Column: Phenomenex Luna AXIA 5u C18 21.2×100. Solvent A: 90% $H_2O$-10% ACN-0.1% TFA; Solvent B: 10% ACN-90% $H_2O$ 0.1% TFA. Start % B=32, Start % B=100). The correct fractions were combined, neutralized with saturated $NaHCO_3$ solution, concentrated under vacuum, and extracted with dichloromethane (3×30 mL). The combined extracts were dried over anhydrous $Na_2SO_4$ and filtered. Removal of the solvent provided ethyl 7-bromo-4-chloroisoquinoline-3-carboxylate (61 mg, 0.194 mmol, 30.2% yield) as a white solid. MS (ESI) m/z: 313.9 [M+H]$^+$; $^1$H NMR (500 MHz, DMSO-$d_6$) δ 8.75 (s, 1H), 8.52 (s, 1H), 8.33 (d, J=8.8 Hz, 1H), 8.19 (dd, J=8.8, 1.9 Hz, 1H), 4.42 (q, J=7.1 Hz, 2H), 1.39 (t, J=7.2 Hz, 3H).

Step 3. Ethyl 7-bromo-1-methoxyisoquinoline-3-carboxylate

To a suspension of ethyl 7-bromo-1-chloroisoquinoline-3-carboxylate (134 mg, 0.426 mmol) in MeOH (5 mL) at 0° C. was added sodium methanolate in MeOH (0.316 mL, 1.704 mmol) dropwise. The resulting mixture was stirred at rt for 3 h. Additional sodium methanolate in MeOH (0.316 mL, 1.704 mmol) was added, and the mixture was stirred rt for another 2 h. The reaction was quenched at 0° C. with saturated $NH_4Cl$ solution (10 mL) and the resulting mixture was extracted with dichloromethane (4×30 mL). The combined extracts were dried over anhydrous MgSO4, filtered, and concentrated under vacuum. The residue was purified by flash chromatograph (12 g silica gel, solid loading, 8-25% ethyl acetate/hexane) to provide methyl 7-bromo-1-methoxyisoquinoline-3-carboxylate (80 mg, 0.270 mmol, 63.4% yield) as a white solid. MS (ESI) m/z: 295.9 [M+H]$^+$.

Intermediate 6

Methyl 2-bromo-7-methylthiazolo[5,4-b]pyridine-5-carboxylate

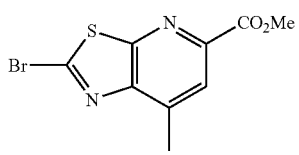

Step 1.5-Chloro-7-methylthiazolo[5,4-b]pyridin-2-amine

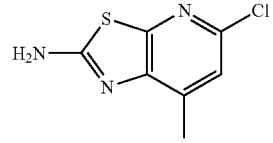

To a mixture of 2,6-dichloro-4-methylpyridin-3-amine (0.500 g, 2.82 mmol) and potassium thiocyanate (0.823 g, 8.47 mmol) in ethanol (7.5 mL) at rt was added concentrated hydrochloric acid (10.04 mL, 330 mmol) dropwise. The mixture was heated at 100° C. for 44 h. Additional potassium thiocyanate (0.823 g, 8.47 mmol) was added and the mixture was heated at 100° C. for additional 31 h. The reaction mixture was concentrated under vacuum to dryness. To the residue was added 1 N NaOH solution (10 mL), followed by solid $K_2CO_3$, until the mixture became basic (pH=9-10). The mixture was extracted with dichloromethane (4×40 mL). The combined extracts were dried over anhydrous $Na_2SO_4$, filtered, and concentrated under vacuum. The residue was purified by flash chromatograph (80 g silica gel, solid loading, 0-6% methanol/dichloromethane) to provide 5-chloro-7-methylthiazolo[5,4-b]pyridin-2-amine (0.331 g, 1.658 mmol, 58.7% yield) as a tan solid. MS (ESI) m/z: 199.9 [M+H]$^+$; $^1$H NMR (500 MHz, DMSO-$d_6$) δ 7.90 (s, 2H), 7.22 (s, 1H), 2.41 (s, 3H).

Step 2. tert-Butyl (5-chloro-7-methylthiazolo[5,4-b]pyridin-2-yl)carbamate

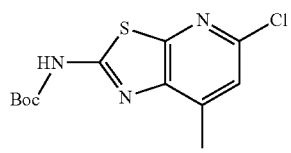 [SMILES: Cc1cc(Cl)nc2sc(NC(=O)OC(C)(C)C)nc12]

To a suspension of 5-chloro-7-methylthiazolo[5,4-b]pyridin-2-amine (0.329 g, 1.648 mmol) in dichloromethane (8 mL) at 0° C. was added di-tert-butyl dicarbonate (0.539 g, 2.472 mmol) in dichloromethane (2 mL), followed by DMAP (0.030 g, 0.247 mmol). The heterogeneous mixture was stirred at rt for 1 h. The solution was diluted with dichloromethane (120 mL), washed with water (2×25 mL) and brine (25 mL), dried over anhydrous MgSO4, filtered, and concentrated under vacuum. The residue was purified by flash chromatograph (40 g silica gel, solid loading, 5-35% ethyl acetate/hexane) to provide tert-butyl (5-chloro-7-methylthiazolo[5,4-b]pyridin-2-yl)carbamate (0.404 g, 1.348 mmol, 82% yield) as a beige solid.

Step 3. Methyl 2-((tert-butoxycarbonyl)amino)-7-methylthiazolo[5,4-b]pyridine-5-carboxylate

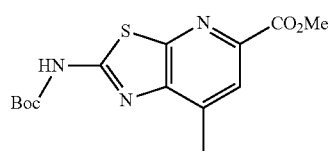 [SMILES: COC(=O)c1cc(C)c2nc(NC(=O)OC(C)(C)C)sc2n1]

A mixture of tert-butyl (5-chloro-7-methylthiazolo[5,4-b]pyridin-2-yl)carbamate (0.404 g, 1.348 mmol), methanol (15 mL, 1.348 mmol), 1,3-bis(diphenylphosphanyl) propane (0.067 g, 0.162 mmol), palladium(II) acetate (0.036 g, 0.162 mmol), and potassium carbonate (0.298 g, 2.156 mmol) was heated under CO (50 psi) in a pressure bottle at 90° C. for 16 h. The mixture was diluted with ethyl acetate (40 mL) and filtered through Celite. The filtrate was concentrated under vacuum to dryness. To the residue was added water (15 mL). The insoluble material was collected as beige solid by suction filtration. The filter cake was further by purified by flash chromatograph (40 g silica gel, solid loading, 10-50% ethyl acetate/hexane) to provide methyl 2-((tert-butoxycarbonyl) amino)-7-methylthiazolo[5,4-b]pyridine-5-carboxylate (0.278 g, 0.860 mmol, 63.8% yield) as a beige solid. MS (ESI) m/z: 324.0 [M+H]$^+$.

Step 4. Methyl 2-amino-7-methylthiazolo[5,4-b]pyridine-5-carboxylate

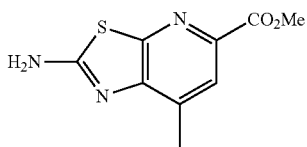

To a suspension of methyl 2-((tert-butoxycarbonyl) amino)-7-methylthiazolo[5,4-b]pyridine-5-carboxylate (0.278 g, 0.860 mmol) in dichloromethane (6 mL) at 0° C. was added 2,2,2-trifluoroacetaldehyde (6 mL, 0.860 mmol) over 2 min. The resulting solution was stirred at rt for 1.5 h and then concentrated under vacuum to dryness. To the residue was added saturated NaHCO$_3$ solution (10 mL) and the precipitating product, methyl 2-amino-7-methylthiazolo[5,4-b]pyridine-5-carboxylate (0.163 g, 0.730 mmol, 85% yield), was collected as a beige solid. MS (ESI) m/z: 223.9 [M+H]$^+$; $^1$H NMR (500 MHz, DMSO-d$_6$) δ 8.22 (s, 2H), 7.84 (s, 1H), 3.85 (s, 3H), 2.47 (s, 3H).

Step 5. Methyl 2-bromo-7-methylthiazolo[5,4-b]pyridine-5-carboxylate

To copper(II) bromide (0.200 g, 0.896 mmol) in acetonitrile (7 mL) at 0° C. was added tert-butyl nitrite (0.154 mL, 1.290 mmol), followed by methyl 2-amino-7-methylthiazolo[5,4-b]pyridine-5-carboxylate (160 mg, 0.717 mmol). The mixture was stirred at rt for 6 h. The mixture was diluted with ethyl acetate (15 mL) and filtered through Celite. The filtrate was concentrated under vacuum. The residue was purified by flash chromatograph (40 g silica gel, solid loading, 20-80% ethyl acetate/hexane) to provide methyl 2-bromo-7-methylthiazolo[5,4-b]pyridine-5-carboxylate (74 mg, 0.258 mmol, 36.0% yield), as a tan solid. (ESI) m/z: 286.8 [M+H]$^+$.

Intermediate 7

Methyl 6-bromo-4-(methoxymethyl)quinoline-2-carboxylate

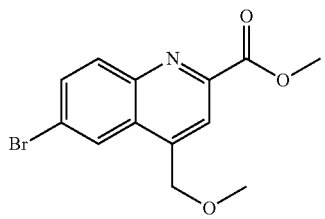 [SMILES: COCc1cc(C(=O)OC)nc2ccc(Br)cc12]

Step 1. Methyl 6-bromo-4-(hydroxymethyl)quinoline-2-carboxylate

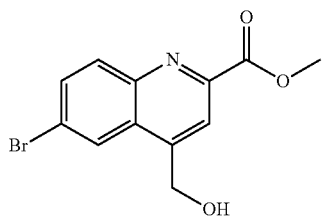 [SMILES: COC(=O)c1cc(CO)c2cc(Br)ccc2n1]

To a mixture of methyl 6-bromoquinoline-2-carboxylate (0.52 g, 1.954 mmol), iron (II) sulfate heptahydrate (0.163 g, 0.586 mmol) and iron (0.109 g, 1.954 mmol) in MeOH (3 mL) and H$_2$O (2 mL) at 0° C. was added concentrated H$_2$SO$_4$ (0.104 mL, 1.954 mmol), followed by 50% H$_2$O$_2$ solution (0.405 mL, 11.73 mmol). The mixture was stirred at rt for 4 h and then at 60° C. for 1 h. It was then diluted with water, basified with ammonium hydroxide, and extracted with EtOAc. The organic layer was washed with brine, dried over MgSO4, filtered, and concentrated under vacuum. The residue was purified by silica gel flash column, eluting with 0-100% EtOAc/hexane to afford methyl 6-bromo-4-(hydroxymethyl)quinoline-2-carboxylate (286 mg, 0.966 mmol, 49.4% yield) as a tan solid. MS (ESI) m/z: 298.0 (M+H)$^+$; $^1$H NMR (400 MHz, chloroform-d) δ 8.30-8.35 (m, 1H), 8.19 (dd, J=3.19, 5.39 Hz, 2H), 7.86 (dd, J=2.09, 9.13 Hz, 1H), 5.22 (s, 2H), 4.09 (s, 3H).

Step 2. Methyl 6-bromo-4-(methoxymethyl)quinoline-2-carboxylate

To methyl 6-bromo-4-(hydroxymethyl)quinoline-2-carboxylate (0.286 g, 0.966 mmol) in DMF (6.44 mL) at 0° C. was added NaH (60% in mineral oil, 0.077 g, 1.932 mmol). The mixture was stirred at rt for 30 min before iodomethane (0.180 mL, 2.90 mmol) was added. The mixture was stirred at rt for 5 h, diluted with EtOAc, washed with water and brine, dried over MgSO4, filtered, and concentrated under vacuum. The residue was purified by silica gel flash column, eluting with 0-30% EtOAc/hexane to give methyl 6-bromo-4-(methoxymethyl)quinoline-2-carboxylate (71 mg, 0.229 mmol, 23.70% yield) as a light yellow solid. MS (ESI) m/z: 312.0 (M+H)$^+$; $^1$H NMR (400 MHz, chloroform-d) δ 8.25-8.27 (m, 1H), 8.17-8.22 (m, 2H), 7.86 (dd, J=2.20, 9.02 Hz, 1H), 4.92 (d, J=0.88 Hz, 2H), 4.09 (s, 3H), 3.54 (s, 3H).

Intermediate 8

Ethyl 6-chloro-4-methoxy-1,5-naphthyridine-2-carboxylate

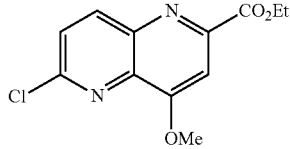 [SMILES: CCOC(=O)c1cc(OC)c2nc(Cl)ccc2n1]

Step 1. Diethyl 2-((6-chloropyridin-3-yl)amino)maleate

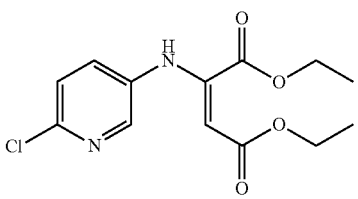 [SMILES: CCOC(=O)/C=C(/Nc1ccc(Cl)nc1)C(=O)OCC]

To 6-chloropyridin-3-amine (6.43 g, 50 mmol) in AcOH (18 mL) at rt was added sodium (Z)-1,4-diethoxy-1,4-dioxobut-2-en-2-olate (11.56 g, 55.0 mmol) portion wise over 10 min. The resulting mixture was stirred at rt for 2.5 days. AcOH was removed under vacuum. The residue was diluted with EtOAc, washed with water, saturated Na₂CO₃ solution (cautious!) and brine sequentially. The organic layer was dried over MgSO4, filtered, and concentrated under vacuum. The residue was purified by a silica gel flash column eluting with 0-20% EtOAc/hexane to afford diethyl 2-((6-chloropyridin-3-yl)amino)maleate (3.36 g, 11.25 mmol, 22.50% yield) as a white solid. MS (ESI) m/z: 299.1 (M+H)$^+$; $^1$H NMR (400 MHz, chloroform-d) δ 9.63 (s, 1H), 8.02 (d, J=2.86 Hz, 1H), 7.17-7.26 (m, 2H), 5.61 (s, 1H), 4.19-4.27 (m, 4H), 1.32 (t, J=7.15 Hz, 3H), 1.20 (t, J=7.04 Hz, 3H).

Step 2. Ethyl 6-chloro-4-hydroxy-1,5-naphthyridine-2-carboxylate

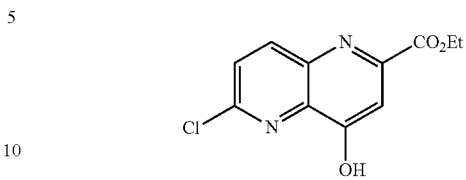

Diethyl 2-((6-chloropyridin-3-yl)amino)maleate (1.50 g, 5.02 mmol) was added portionwise to a vigorously stirred, boiling diphenyl ether (25 mL) over 15 min. The mixture was maintained at reflux for 20 min. The reaction mixture was allowed to cool to rt. Hexane (25 mL) was added. The insoluble crude product was collected via filtration. It was then purified by flash chromatography (silica gel, hexanes: EtOAc, 0-100% to 100% EtOAc) to afford 0.37 g (29% yield) of ethyl 6-chloro-4-hydroxy-1,5-naphthyridine-2-carboxylate as pink solid: $^1$H NMR (400 MHz, methanol-d4) δ 8.35 (d, J=8.9 Hz, 1H), 7.81 (d, J=8.9 Hz, 1H), 7.22 (bs, 1H), 4.53 (q, J=7.2 Hz, 2H), 1.47 (t, J=7.1 Hz, 3H). LCMS (ES): m/z 253.1 [M+H]$^+$.

Step 3. Ethyl 6-chloro-4-methoxy-1,5-naphthyridine-2-carboxylate

A mixture of ethyl 6-chloro-4-hydroxy-1,5-naphthyridine-2-carboxylate (225 mg, 0.892 mmol), iodomethane (320 mg, 2.25 mmol), and K₂CO₃ (327 mg, 2.36 mmol) in DMF (9 mL) was heated at 65° C. in a sealed vial for 45 min. The reaction mixture was diluted with CH₂Cl₂ (10 mL) and filtered through Celite. The filtrate was concentrated to give a crude product which was purified by flash chromatography (silica gel, hexanes:EtOAc, 100:0 to 0:100) to afford 167 mg (71% yield) of ethyl 6-chloro-4-methoxy-1,5-naphthyridine-2-carboxylate as white solid: $^1$H NMR (400 MHz, chloroform-d) δ 8.50 (d, J=8.8 Hz, 1H), 7.84 (s, 1H), 7.70 (d, J=8.9 Hz, 1H), 4.59 (q, J=7.1 Hz, 2H), 4.22 (s, 3H), 1.52 (t, J=7.1 Hz, 3H). LCMS (ES): m/z 267.0 [M+H]$^+$.

Examples 4 to 28 in Table 1 were synthesized according to the procedures described for Examples 1 to 3 above.

TABLE 1

| Ex. No. | Structure and Name |
|---|---|
| 4 | (E)-6-(6-(2-(5-cyclopropyl-3-(2,6-dichlorophenyl)isoxazol-4-yl)vinyl)-2-azaspiro[3.3]heptan-2-yl)-4-(trifluoromethyl)quinoline-2-carboxylic acid |

TABLE 1-continued

| Ex. No. | Structure and Name |
|---|---|
| 5 | 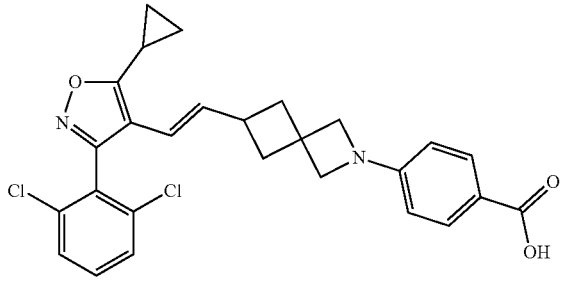<br>(E)-4-(6-(2-(5-cyclopropyl-3-(2,6-dichlorophenyl)isoxazol-4-yl)vinyl)-2-azaspiro[3.3]heptan-2-yl)benzoic acid |
| 6 | 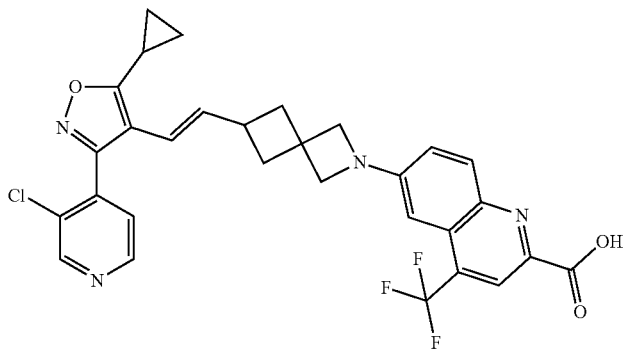<br>(E)-6-(6-(2-(3-(3-chloropyridin-4-yl)-5-cyclopropylisoxazol-4-yl)vinyl)-2-azaspiro[3.3]heptan-2-yl)-4-(trifluoromethyl)quinoline-2-carboxylic acid |
| 7 | 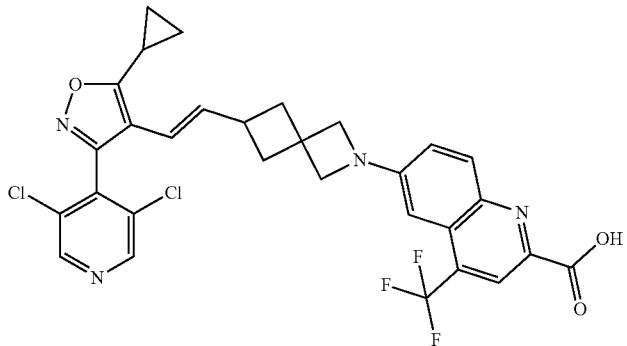<br>(E)-6-(6-(2-(5-cyclopropyl-3-(3,5-dichloropyridin-4-yl)isoxazol-4-yl)vinyl)-2-azaspiro[3.3]heptan-2-yl)-4-(trifluoromethyl)quinoline-2-carboxylic acid |
| 8 | 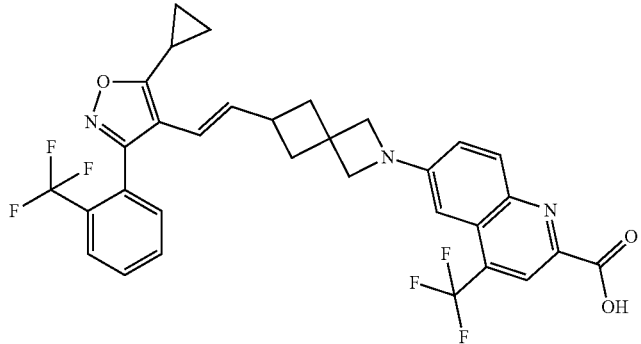<br>(E)-6-(6-(2-(5-cyclopropyl-3-(2-(trifluoromethyl)phenyl)isoxazol-4-yl)vinyl)-2-azaspiro[3.3]heptan-2-yl)-4-(trifluoromethyl)quinoline-2-carboxylic acid |

TABLE 1-continued

| Ex. No. | Structure and Name |
|---|---|
| 9 | 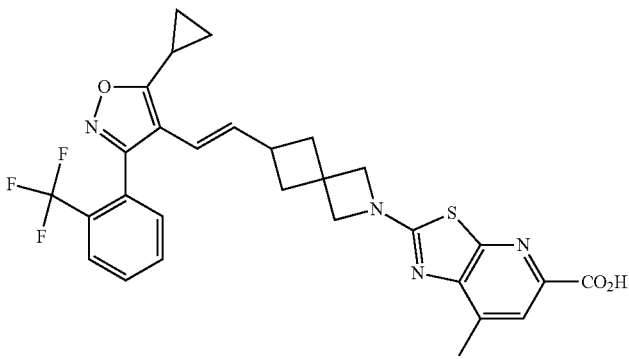
(E)-2-(6-(2-(5-cyclopropyl-3-(2-(trifluoromethyl)phenyl)isoxazol-4-yl)vinyl)-2-azaspiro[3.3]heptan-2-yl)-7-methylthiazolo[5,4-b]pyridine-5-carboxylic acid |
| 10 | 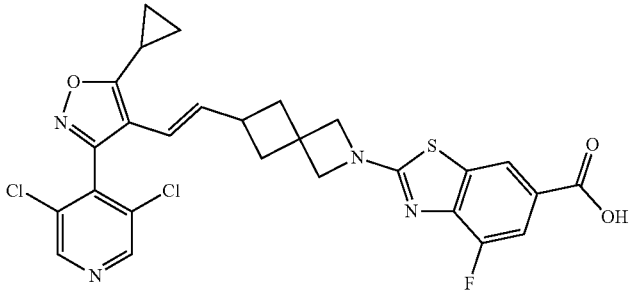
(E)-2-(6-(2-(5-cyclopropyl-3-(3,5-dichloropyridin-4-yl)isoxazol-4-yl)vinyl)-2-azaspiro[3.3]heptan-2-yl)-4-fluorobenzo[d]thiazole-6-carboxylic acid |
| 11 | 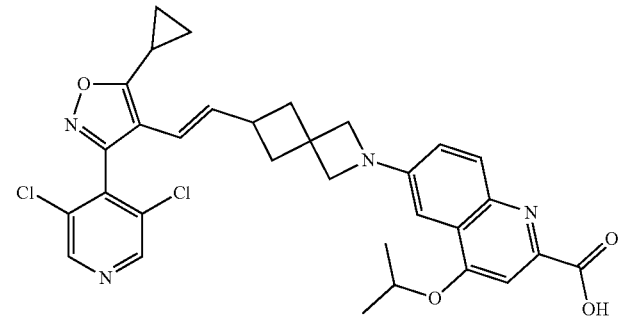
(E)-6-(6-(2-(5-cyclopropyl-3-(3,5-dichloropyridin-4-yl)isoxazol-4-yl)vinyl)-2-azaspiro[3.3]heptan-2-yl)-4-isopropoxyquinoline-2-carboxylic acid |
| 12 | 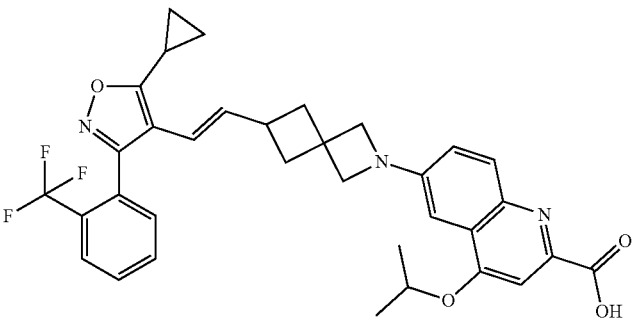
(E)-6-(6-(2-(5-cyclopropyl-3-(2-(trifluoromethyl)phenyl)isoxazol-4-yl)vinyl)-2-azaspiro[3.3]heptan-2-yl)-4-isopropoxyquinoline-2-carboxylic acid |

TABLE 1-continued

| Ex. No. | Structure and Name |
|---|---|
| 13 | 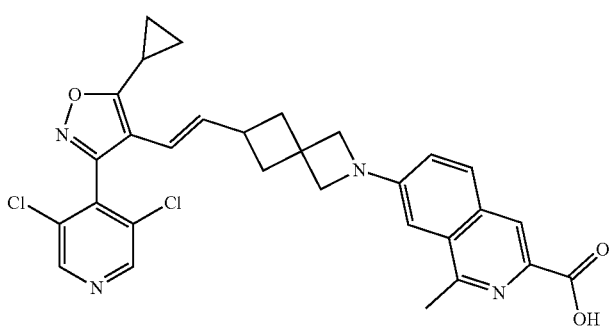<br>(E)-7-(6-(2-(5-cyclopropyl-3-(3,5-dichloropyridin-4-yl)isoxazol-4-yl)vinyl)-2-azaspiro[3.3]heptan-2-yl)-1-methylisoquinoline-3-carboxylic acid |
| 14 | 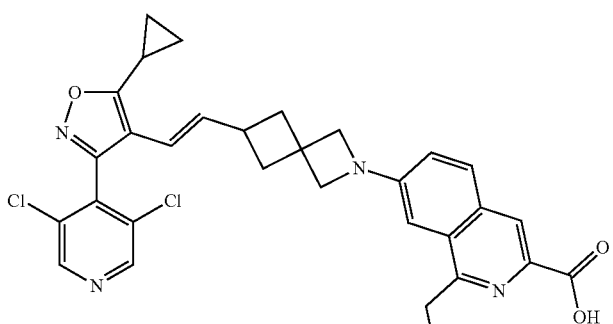<br>(E)-7-(6-(2-(5-cyclopropyl-3-(3,5-dichloropyridin-4-yl)isoxazol-4-yl)vinyl)-2-azaspiro[3.3]heptan-2-yl)-1-ethylisoquinoline-3-carboxylic acid |
| 15 | 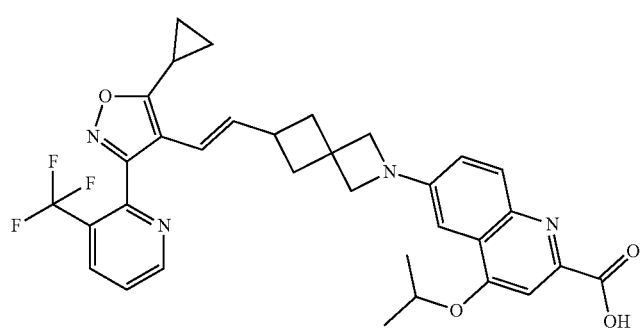<br>(E)-6-(6-(2-(5-cyclopropyl-3-(3-(trifluoromethyl)pyridin-2-yl)isoxazol-4-yl)vinyl)-2-azaspiro[3.3]heptan-2-yl)-4-isopropoxyquinoline-2-carboxylic acid |
| 16 | 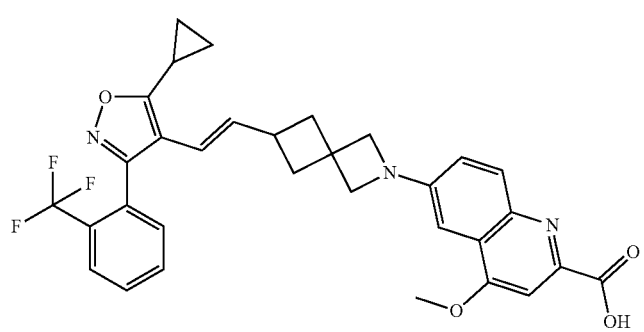<br>(E)-6-(6-(2-(5-cyclopropyl-3-(2-(trifluoromethyl)phenyl)isoxazol-4-yl)vinyl)-2-azaspiro[3.3]heptan-2-yl)-4-methoxyquinoline-2-carboxylic acid |

TABLE 1-continued

| Ex. No. | Structure and Name |
|---|---|
| 17 | 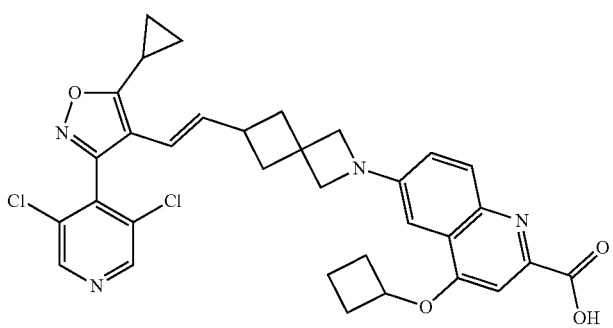<br>(E)-4-cyclobutoxy-6-(6-(2-(5-cyclopropyl-3-(3,5-dichloropyridin-4-yl)isoxazol-4-yl)vinyl)-2-azaspiro[3.3]heptan-2-yl)quinoline-2-carboxylic acid |
| 18 | 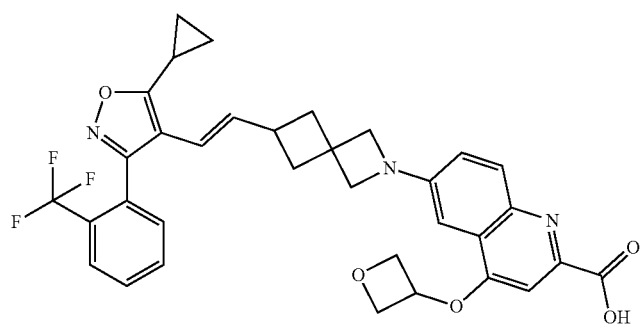<br>(E)-6-(6-(2-(5-cyclopropyl-3-(2-(trifluoromethyl)phenyl)isoxazol-4-yl)vinyl)-2-azaspiro[3.3]heptan-2-yl)-4-(oxetan-3-yloxy)quinoline-2-carboxylic acid |
| 19 | 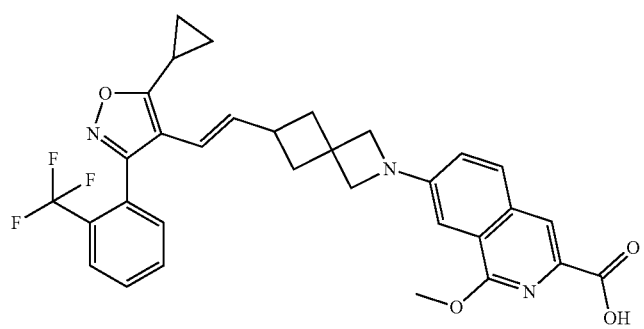<br>(E)-7-(6-(2-(5-cyclopropyl-3-(2-(trifluoromethyl)phenyl)isoxazol-4-yl)vinyl)-2-azaspiro[3.3]heptan-2-yl)-1-methoxyisoquinoline-3-carboxylic acid |
| 20 | 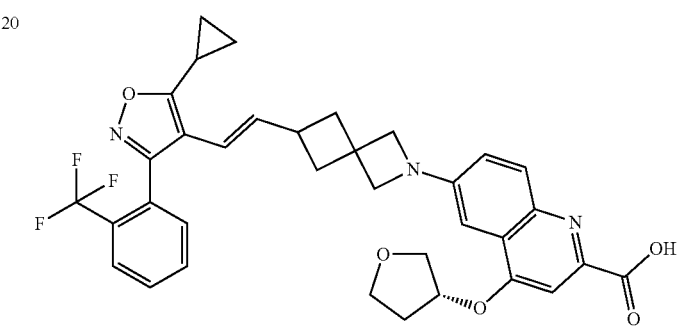<br>(R,E)-6-(6-(2-(5-cyclopropyl-3-(2-(trifluoromethyl)phenyl)isoxazol-4-yl)vinyl)-2-azaspiro[3.3]heptan-2-yl)-4-((tetrahydrofuran-3-yl)oxy)quinoline-2-carboxylic acid |

TABLE 1-continued

| Ex. No. | Structure and Name |
|---|---|
| 21 | 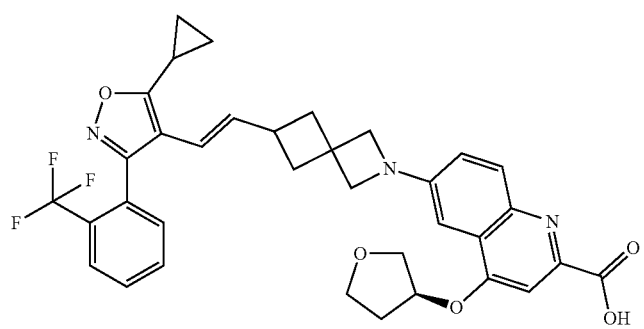<br>(S,E)-6-(6-(2-(5-cyclopropyl-3-(2-(trifluoromethyl)phenyl)isoxazol-4-yl)vinyl)-2-azaspiro[3.3]heptan-2-yl)-4-((tetrahydrofuran-3-yl)oxy)quinoline-2-carboxylic acid |
| 22 | 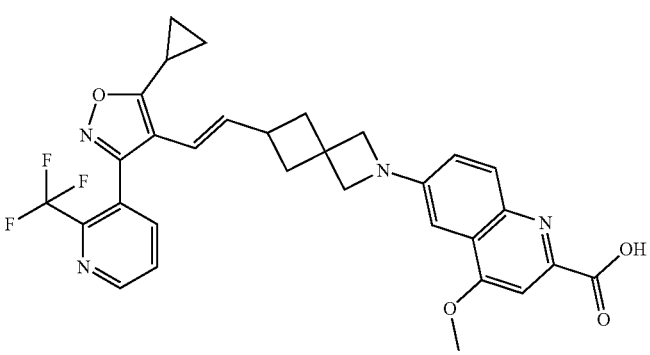<br>(E)-6-(6-(2-(5-cyclopropyl-3-(2-(trifluoromethyl)pyridin-3-yl)isoxazol-4-yl)vinyl)-2-azaspiro[3.3]heptan-2-yl)-4-methoxyquinoline-2-carboxylic acid |
| 23 | 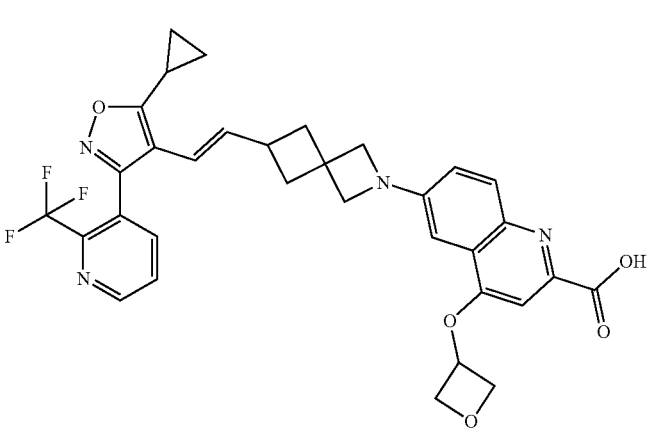<br>(E)-6-(6-(2-(5-cyclopropyl-3-(2-(trifluoromethyl)pyridin-3-yl)isoxazol-4-yl)vinyl)-2-azaspiro[3.3]heptan-2-yl)-4-(oxetan-3-yloxy)quinoline-2-carboxylic acid |

TABLE 1-continued

| Ex. No. | Structure and Name |
|---|---|
| 24 | 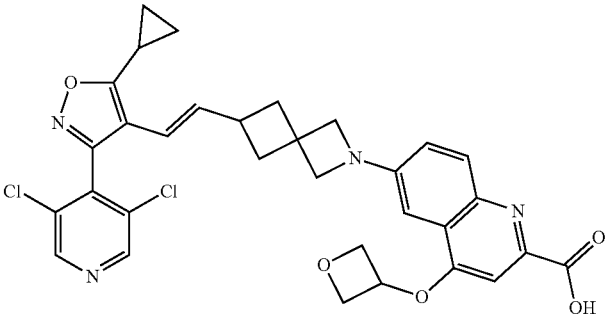<br>(E)-6-(6-(2-(5-cyclopropyl-3-(3,5-dichloropyridin-4-yl)isoxazol-4-yl)vinyl)-2-azaspiro[3.3]heptan-2-yl)-4-(oxetan-3-yloxy)quinoline-2-carboxylic acid |
| 25 | 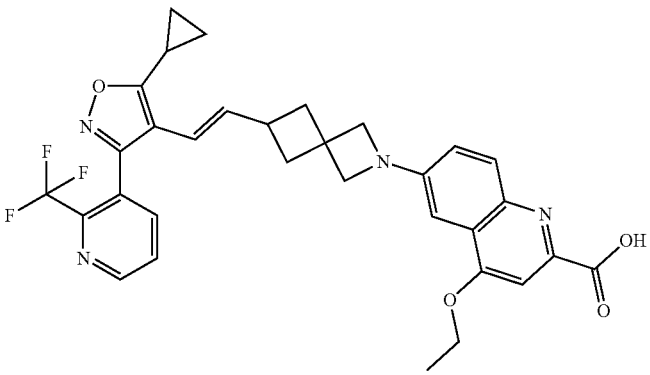<br>(E)-6-(6-(2-(5-cyclopropyl-3-(2-(trifluoromethyl)pyridin-3-yl)isoxazol-4-yl)vinyl)-2-azaspiro[3.3]heptan-2-yl)-4-ethoxyquinoline-2-carboxylic acid |
| 26 | 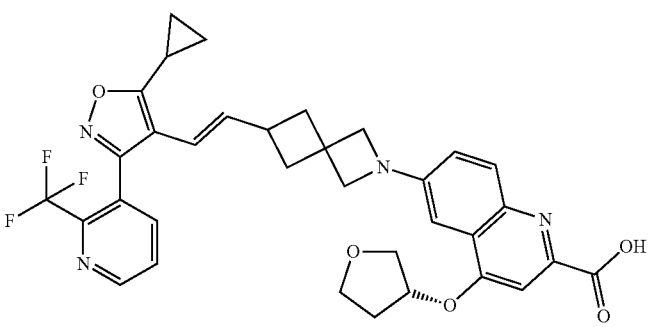<br>(R,E)-6-(6-(2-(5-cyclopropyl-3-(2-(trifluoromethyl)pyridin-3-yl)isoxazol-4-yl)vinyl)-2-azaspiro[3.3]heptan-2-yl)-4-((tetrahydrofuran-3-yl)oxy)quinoline-2-carboxylic acid |
| 27 | 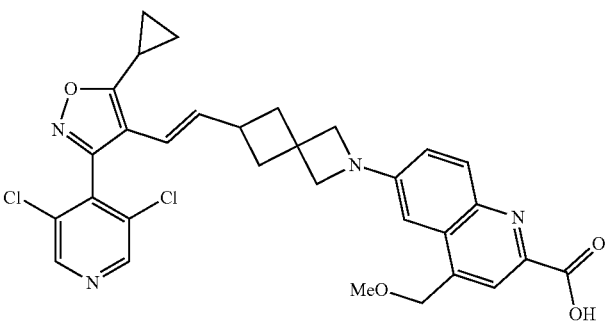<br>(E)-6-(6-(2-(5-cyclopropyl-3-(3,5-dichloropyridin-4-yl)isoxazol-4-yl)vinyl)-2-azaspiro[3.3]heptan-2-yl)-4-(methoxymethyl)quinoline-2-carboxylic acid |

TABLE 1-continued

| Ex. No. | Structure and Name |
|---|---|
| 28 | 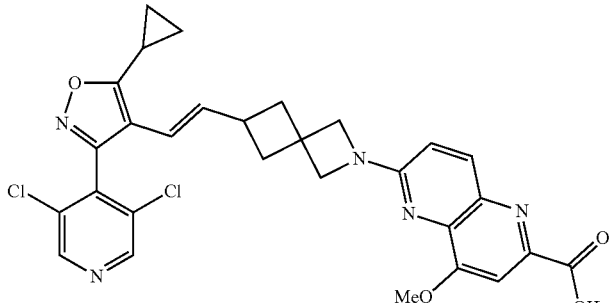<br>(E)-6-(6-(2-(5-cyclopropyl-3-(3,5-dichloropyridin-4-yl)isoxazol-4-yl)vinyl)-2-azaspiro[3.3]heptan-2-yl)-4-(methoxymethyl)quinoline-2-carboxylic acid |
| 4 | MS (ESI) m/z: 613.9 [M + H]$^+$; EC$_{50}$ = 60; $^1$H NMR (500 MHz, METHANOL-d$_4$) δ 8.28 (s, 1H), 8.09 (br d, J = 9.08 Hz, 1H), 7.57-7.61 (m, 2H), 7.51-7.57 (m, 1H), 7.17 (br d, J = 8.53 Hz, 1H), 6.62 (br s, 1H), 6.12 (d, J = 15.96 Hz, 1H), 5.53-5.64 (m, 1H), 4.08 (s, 2H), 3.87 (s, 2H), 2.88 (s, 1H), 2.45 (br dd, J = 8.25, 12.10 Hz, 2H), 2.20-2.29 (m, 1H), 1.91-2.00 (m, 2H), 1.17-1.20 (m, 2H), 1.16 (br d, J = 2.20 Hz, 2H). |
| 5 | MS (ESI) m/z: 494.9 [M + H]$^+$; EC$_{50}$ = 130; $^1$H NMR (400 MHz, METHANOL-d$_4$) δ 7.83 (d, J = 8.80 Hz, 2H), 7.52-7.63 (m, 3H), 6.38 (d, J = 8.80 Hz, 2H), 6.10 (dd, J = 1.32, 16.07 Hz, 1H), 5.58 (dd, J = 7.37, 15.96 Hz, 1H), 3.92 (s, 2H), 3.72 (s, 2H), 2.40 (br s, 2H), 2.22-2.29 (m, 1H), 1.87-1.96 (m, 2H), 1.14-1.21 (m, 4H). |
| 6 | MS (ESI) m/z: 581.1 [M + H]$^+$; EC$_{50}$ = 140; $^1$H NMR (400 MHz, METHANOL-d$_4$) δ 8.80 (s, 1H), 8.67 (d, J = 5.06 Hz, 1H), 8.30 (s, 1H), 8.11 (d, J = 9.24 Hz, 1H), 7.54 (d, J = 4.84 Hz, 1H), 7.21 (dd, J = 2.42, 9.24 Hz, 1H), 6.66 (br s, 1H), 6.13 (dd, J = 1.10, 16.07 Hz, 1H), 5.65-5.80 (m, 1H), 4.13 (s, 2H), 3.93 (s, 2H), 2.90-3.02 (m, 1H), 2.47 (ddd, J = 2.31, 8.03, 10.12 Hz, 2H), 2.27 (br d, J = 1.54 Hz, 1H), 2.02-2.12 (m, 1H), 1.20 (td, J = 2.61, 8.20 Hz, 2H), 1.14-1.18 (m, 2H). |
| 7 | MS (ESI) m/z: 615.0 [M + H]$^+$; EC$_{50}$ = 530; $^1$H NMR (400 MHz, METHANOL-d$_4$) δ 8.75 (s, 2H), 8.28 (s, 1H), 8.09 (br d, J = 9.24 Hz, 1H), 7.18 (dd, J = 2.09, 9.13 Hz, 1H), 6.63 (br s, 1H), 6.12 (d, J = 16.07 Hz, 1H), 5.53-5.68 (m, 1H), 4.09 (s, 2H), 3.89 (s, 2H), 2.92 (br d, J = 7.70 Hz, 1H), 2.38-2.51 (m, 2H), 2.16-2.37 (m, 1H), 1.93-2.10 (m, 2H), 1.14-1.25 (m, 4H). |
| 8 | MS (ESI) m/z: 614.1 [M + H]$^+$; EC$_{50}$ = 137; $^1$H NMR (400 MHz, METHANOL-d$_4$) δ 8.29 (s, 1H), 8.10 (d, J = 9.24 Hz, 1H), 7.89-7.96 (m, 1H), 7.73-7.84 (m, 2H), 7.48 (d, J = 6.82 Hz, 1H), 7.17 (dd, J = 2.42, 9.24 Hz, 1H), 6.62 (br s, 1H), 6.06 (dd, J = 1.10, 16.07 Hz, 1H), 5.58 (dd, J = 7.70, 16.07 Hz, 1H), 4.08 (s, 2H), 3.84 (s, 2H), 2.82-2.92 (m, 1H), 2.38-2.47 (m, 2H), 2.19-2.29 (m, 1H), 1.91-2.01 (m, 2H), 1.11-1.30 (m, 4H). |
| 9 | MS (ESI) m/z: 567.1 [M + H]$^+$; EC$_{50}$ = 268; $^1$H NMR (500 MHz, METHANOL-d$_4$) δ 7.98-7.89 (m, 2H), 7.86-7.75 (m, 2H), 7.48 (d, J = 7.2 Hz, 2H), 6.06 (d, J = 16.0 Hz, 1H), 5.59 (dd, J = 16.0, 7.4 Hz, 1H), 4.27 (s, 2H), 4.04 (s, 2H), 2.93-2.83 (m, 1H), 2.58 (s, 3H), 2.51-2.40 (m, 2H), 2.32-2.20 (m, 1H), 2.07-1.93 (m, 2H), 1.26-1.11 (m, 4H). |
| 10 | MS (ESI) m/z: 571.2 [M + H]$^+$; EC$_{50}$ = 667; $^1$H NMR (500 MHz, DMSO-d$_6$) δ 8.89 (s, 2H), 8.21 (s, 1H), 7.60 (br d, J = 11.60 Hz, 1H), 6.12 (d, J = 16.17 Hz, 1H), 5.55 (dd, J = 7.02, 16.17 Hz, 1H), 4.20 (s, 2H), 4.01 (s, 2H), 2.79-2.93 (m, 1H), 2.33-2.44 (m, 3H), 1.98 (br t, J = 10.07 Hz, 2H), 1.19 (br d, J = 8.24 Hz, 2H), 1.08-1.13 (m, 2H). |
| 11 | MS (ESI) m/z: 605.1 [M + H]$^+$; EC$_{50}$ = 79; $^1$H NMR (500 MHz, METHANOL-d$_4$) δ 8.77 (s, 2H), 8.11 (d, J = 9.35 Hz, 1H), 7.70 (s, 1H), 7.28 (dd, J = 2.34, 9.22 Hz, 1H), 6.87 (d, J = 2.48 Hz, 1H), 6.13 (d, J = 15.41 Hz, 1H), 5.62 (dd, J = 7.43, 15.96 Hz, 1H), 5.26 (s, 1H), 4.05-4.12 (m, 2H), 3.87 (s, 2H), 2.92 (br d, J = 7.70 Hz, 1H), 2.41-2.49 (m, 2H), 2.28 (s, 1H), 1.95-2.06 (m, 2H), 1.59 (d, J = 6.05 Hz, 6H), 1.21 (td, J = 2.68, 8.39 Hz, 2H), 1.15-1.19 (m, 2H). |
| 12 | MS (ESI) m/z: 604.2 [M + H]$^+$; EC$_{50}$ = 29; $^1$H NMR (500 MHz, METHANOL-d$_4$) δ 8.09-8.16 (m, 1H), 7.93 (d, J = 7.43 Hz, 1H), 7.74-7.84 (m, 2H), 7.71 (s, 1H), 7.48 (d, J = 7.15 Hz, 1H), 7.29 (dd, J = 2.48, 9.08 Hz, 1H), 6.87 (d, J = 2.48 Hz, 1H), 6.05 (dd, J = 0.83, 15.96 Hz, 1H), 5.59 (dd, J = 7.43, 15.96 Hz, 1H), 5.22-5.32 (m, 1H), 4.08 (s, 2H), 3.85 (s, 2H), 2.82-2.93 (m, 1H), 2.37-2.46 (m, 2H), 2.20-2.28 (m, 1H), 1.91-2.00 (m, 2H), 1.59 (d, J = 6.05 Hz, 6H), 1.17-1.22 (m, 2H), 1.12-1.17 (m, 2H). |
| 13 | MS (ESI) m/z: 561.1 [M + H]$^+$; EC$_{50}$ = 429; $^1$H NM$^1$HR (400 MHz, METHANOL-d$_4$) δ 8.79 (s, 2H), 8.61 (s, 1H), 8.11 (br d, J = 9.02 Hz, 1H), 7.36 (br d, J = 8.36 Hz, 1H), 6.98 (s, 1H), 6.09-6.20 (m, 1H), 5.62 (dd, J = 7.48, 16.07 Hz, 1H), 4.17 (s, 2H), 3.95 (s, 2H), 3.11-3.19 (m, 3H), 2.88-3.01 (m, 1H), 2.44-2.54 (m, 2H), 2.23-2.36 (m, 1H), 1.98-2.08 (m, 2H), 1.16-1.27 (m, 4H). |

TABLE 1-continued

| Ex. No. | Structure and Name |
|---|---|
| 14 | MS (ESI) m/z: 575.2 [M + H]$^+$; EC$_{50}$ = 302; $^1$H NMR (500 MHz, METHANOL-d$_4$) δ 8.77 (s, 2H), 8.59 (s, 1H), 8.11 (d, J = 9.08 Hz, 1H), 7.36 (dd, J = 1.79, 8.94 Hz, 1H), 7.02 (s, 1H), 6.08-6.19 (m, 1H), 5.61 (dd, J = 7.43, 15.96 Hz, 1H), 4.16 (s, 2H), 3.93 (s, 2H), 3.56 (br d, J = 7.43 Hz, 2H), 2.93 (br d, J = 7.43 Hz, 1H), 2.43-2.53 (m, 2H), 2.23-2.32 (m, 1H), 1.96-2.07 (m, 2H), 1.49 (t, J = 7.57 Hz, 3H), 1.14-1.25 (m, 4H). |
| 15 | MS (ESI) m/z: 605.2 [M + H]$^+$: EC$_{50}$ = 85; $^1$H NMR (500 MHz METHANOL-d$_4$) δ 8.96 (br d, J = 4.68 Hz, 1H), 8.38 (br d, J = 8.25 Hz, 1H), 8.12 (br d, J = 6.60 Hz, 1H), 7.80 (br dd, J = 4.95, 7.70 Hz, 1H), 7.72 (br s, 1H), 7.31 (br d, J = 7.43 Hz, 1H), 6.87 (br s, 1H), 6.04-6.17 (m, 1H), 5.57 (dd, J = 7.02, 16.09 Hz, 1H), 5.27 (br d, J = 1.65 Hz, 1H), 4.07-4.14 (m, 2H), 3.90 (br s, 2H), 2.84-2.93 (m, 1H), 2.41 (br t, J = 9.77 Hz, 2H), 2.21-2.30 (m, 1H), 1.97-2.05 (m, 2H), 1.58 (br d, J = 5.50 Hz, 6H), 1.18-1.22 (m, 2H), 1.13-1.17 (m, 2H). |
| 16 | MS (ESI) m/z: 576.2 [M + H]$^+$; EC$_{50}$ = 104; $^1$H NMR (400 MHz, METHANOL-d$_4$) δ 8.08-8.34 (m, 1H), 7.92 (br d, J = 7.04 Hz, 1H), 7.68-7.85 (m, 3H), 7.47 (br d, J = 6.82 Hz, 1H), 7.14-7.32 (m, 1H), 6.76-6.93 (m, 1H), 5.98-6.10 (m, 1H), 5.60 (br d, J = 7.48 Hz, 1H), 4.30 (br s, 3H), 4.05 (br s, 2H), 3.81 (br d, J = 4.18 Hz, 2H), 2.77-2.92 (m, 1H), 2.40 (br t, J = 8.58 Hz, 2H), 2.20-2.27 (m, 1H), 1.95 (br d, J = 6.16 Hz, 2H), 1.09-1.35 (m, 4H). |
| 17 | MS (ESI) m/z: 617.2 [M + H]+; EC$_{50}$ = 85; $^1$H NMR (400 MHz, METHANOL-d$_4$) δ 8.75-8.80 (m, 2H), 8.14 (br d, J = 9.46 Hz, 1H), 7.54 (s, 1H), 7.31 (br d, J = 9.68 Hz, 1H), 6.89 (d, J = 2.42 Hz, 1H), 6.14 (dd, J = 1.32, 16.07 Hz, 1H), 5.62 (dd, J = 7.37, 15.96 Hz, 1H), 5.24-5.35 (m, 1H), 4.11 (s, 2H), 3.89 (s, 2H), 2.93 (br d, J = 7.48 Hz, 1H), 2.68-2.76 (m, 2H), 2.39-2.52 (m, 4H), 2.24-2.33 (m, 1H), 1.97-2.09 (m, 4H), 1.86-1.96 (m, 1H), 1.18-1.24 (m, 4H). |
| 18 | MS (ESI) m/z: 618.2 [M + H]$^+$, EC$_{50}$ = 52; $^1$H NMR (400 MHz, DMSO-d$_6$) δ 7.98 (d, J = 7.26 Hz, 1H), 7.93 (d, J = 9.24 Hz, 1H), 7.80-7.89 (m, 2H), 7.55 (d, J = 7.26 Hz, 1H), 7.08 (dd, J = 2.64, 9.02 Hz, 1H), 7.03 (s, 1H), 6.81 (d, J = 2.64 Hz, 1H), 6.05 (dd, J = 1.10, 16.07 Hz, 1H), 5.65 (t, J = 4.84 Hz, 1H), 5.49 (dd, J = 7.48, 16.07 Hz, 1H), 5.06 (t, J = 6.71 Hz, 2H), 4.71 (dd, J = 4.62, 7.70 Hz, 2H), 4.00 (s, 2H), 3.77 (s, 2H), 2.82 (br d, J = 7.92 Hz, 1H), 2.31-2.40 (m, 3H), 1.88 (br dd, J = 7.48, 12.10 Hz, 2H), 1.16 (br d, J = 8.36 Hz, 2H), 1.08 (dd, J = 2.20, 5.06 Hz, 2H). |
| 19 | MS (ESI) m/z: 576.2 [M + H]$^+$; EC$_{50}$ = 169; $^1$H NMR (400 MHz, METHANOL-d$_4$) δ 8.05 (s, 1H), 7.86-7.96 (m, 1H), 7.71-7.82 (m, 3H), 7.42-7.50 (m, 1H), 6.89-6.99 (m, 2H), 6.04 (dd, J = 1.10, 16.07 Hz, 1H), 5.58 (dd, J = 7.48, 16.07 Hz, 1H), 4.17 (s, 3H), 3.97 (s, 2H), 3.72 (s, 2H), 2.85 (d, J = 7.48 Hz, 1H), 2.33-2.45 (m, 2H), 2.20-2.27 (m, 1H), 1.87-1.97 (m, 2H), 1.11-1.21 (m, 4H). |
| 20 | MS (ESI) m/z: 632.3 [M+H]$^+$; EC$_{50}$ = 33; $^1$H NMR (400 MHz, METHANOL-d$_4$) δ 8.12 (d, J = 9.24 Hz, 1H), 7.90-7.96 (m, 1H), 7.74-7.84 (m, 2H), 7.67 (s, 1H), 7.44-7.50 (m, 1H), 7.27 (dd, J = 2.42, 9.24 Hz, 1H), 6.84 (d, J = 2.20 Hz, 1H), 5.98-6.14 (m, 1H), 5.53-5.64 (m, 2H), 4.18-4.26 (m, 1H), 4.04-4.15 (m, 4H), 3.91-4.04 (m, 1H), 3.84 (s, 2H), 2.87 (br d, J = 7.70 Hz, 1H), 2.50-2.61 (m, 1H), 2.36-2.46 (m, 2H), 2.18-2.36 (m, 2H), 1.91-2.02 (m, 2H), 1.10-1.23 (m, 4H). |
| 21 | MS (ESI) m/z: 632.3 [M + H]$^+$; EC$_{50}$ = 18; $^1$H NMR (400 MHz, METHANOL-d$_4$) δ 8.09-8.17 (m, 1H), 7.90-7.98 (m, 1H), 7.74-7.84 (m, 2H), 7.69 (s, 1H), 7.47 (br d, J = 6.38 Hz, 1H), 7.28 (dd, J = 2.42, 9.24 Hz, 1H), 6.86 (d, J = 2.20 Hz, 1H), 6.05 (d, J = 16.07 Hz, 1H), 5.54-5.66 (m, 2H), 4.18-4.27 (m, 1H), 4.03-4.16 (m, 4H), 3.92-4.03 (m, 1H), 3.85 (s, 2H), 2.87 (br d, J = 7.70 Hz, 1H), 2.55 (s, 1H), 2.38-2.47 (m, 2H), 2.20-2.37 (m, 2H), 1.89-2.04 (m, 2H), 1.12-1.23 (m, 4H). |
| 22 | MS (ESI) m/z: 577.2 [M + H]$^+$; EC$_{50}$ = 111; $^1$H NMR (400 MHz, DMSO-d$_6$) δ 8.90 (dd, J = 4.7, 1.5 Hz, 1H), 8.05 (dd, J = 7.9, 1.5 Hz, 1H), 7.95 (d, J = 9.2 Hz, 1H), 7.86 (dd, J = 7.9, 4.7 Hz, 1H), 7.44 (s, 1H), 7.07 (dd, J = 9.1, 2.6 Hz, 1H), 6.65 (d, J = 2.6 Hz, 1H), 6.02 (dd, J = 16.1, 1.2 Hz, 1H), 5.46 (dd, J = 16.1, 7.4 Hz, 1H), 4.07 (s, 3H), 3.93 (s, 2H), 3.71 (s, 2H), 2.78 (q, J = 7.7 Hz, 1H), 2.36-2.18 (m, 3H), 1.95-1.77 (m, 2H), 1.18-0.90 (m, 4H). |
| 23 | MS (ESI) m/z: 619.3 [M + H]$^+$; EC$_{50}$ = 165; $^1$H NMR (400 MHz, DMSO-d$_6$) δ 8.98 (dd, J = 4.8, 1.5 Hz, 1H), 8.13 (dd, J = 7.9, 1.5 Hz, 1H), 8.02-7.87 (m, 2H), 7.12 (dd, J = 9.2, 2.6 Hz, 1H), 7.06 (s, 1H), 6.83 (d, J = 2.6 Hz, 1H), 6.11 (dd, J = 16.2, 1.2 Hz, 1H), 5.68 (p, J = 5.2 Hz, 1H), 5.53 (dd, J = 16.1, 7.5 Hz, 1H), 5.14-4.97 (m, 2H), 4.73 (dd, J = 7.6, 4.5 Hz, 2H), 4.03 (s, 2H), 3.80 (s, 2H), 2.85 (hept, J = 7.2, 6.7 Hz, 1H), 2.44-2.30 (m, 3H), 1.98-1.84 (m, 2H), 1.24-0.98 (m, 4H). |
| 24 | MS (ESI) m/z: 619.3 [M + H]$^+$; EC$_{50}$ = 114; $^1$H NMR (400 MHz, METHANOL-d$_4$) δ 8.77 (s, 2H), 8.11-8.18 (m, 1H), 7.30 (s, 2H), 6.96 (d, J = 2.64 Hz, 1H), 6.13 (dd, J = 1.10, 16.07 Hz, 1H), 5.83 (br s, 1H), 5.57-5.66 (m, 1H), 5.17-5.24 (m, 2H), 4.91 (dd, J = 4.62, 7.70 Hz, 2H), 4.12 (s, 2H), 3.90 (s, 2H), 2.87-2.98 (m, 1H), 2.42-2.52 (m, 2H), 2.28 (s, 1H), 2.02 (br s, 2H), 1.14-1.22 (m, 4H). |
| 25 | MS (ESI): m/z 591.4 [M + H]$^+$; EC$_{50}$ = 153; $^1$H NMR (400 MHz, DMSO-d$_6$) δ 8.91 (d, J = 4.8, 1.5 Hz, 1H), 8.05 (dd, J = 7.9, 1.6 Hz, 1H), 7.93 (d, J = 9.1 Hz, 1H), 7.87 (dd, J = 7.9, 4.7 Hz, 1H), 7.40 (s, 1H), 7.06 (dd, J = 9.1, 2.5 Hz, 1H), 6.67 (d, J = 2.6 Hz, 1H), 6.03 (dd, J = 16.1, 1.2 Hz, 1H), 5.45 (dd, J = 16.1, 7.5 Hz, 1H), 4.35 (q, J = 6.9 Hz, 2H), 3.93 (s, 2H), 3.70 (s, 2H), 2.77 (p, J = 7.8 Hz, 1H), 2.35-2.23 (m, 3H), 1.91-1.70 (m, 2H), 1.43 (t, J = 6.9 Hz, 3H), 1.17-0.96 (m, 4H). |

TABLE 1-continued

| Ex. No. | Structure and Name |
|---|---|
| 26 | MS (ESI): m/z 633.4 [M + H]$^+$; EC$_{50}$ = 231; $^1$H NMR (400 MHz, DMSO-d6) δ 8.91 (dd, J = 4.8, 1.5 Hz, 1H), 8.05 (dd, J = 7.9, 1.5 Hz, 1H), 7.93-7.83 (m, 2H), 7.36 (d, J = 1.8 Hz, 1H), 7.03 (dd, J = 9.2, 2.7 Hz, 1H), 6.65 (d, J = 2.6 Hz, 1H), 6.03 (dd, J = 16.1, 1.2 Hz, 1H), 5.44 (dd, J = 16.1, 7.5 Hz, 1H), 5.40-5.34 (m, 1H), 3.94 (d, J = 3.5 Hz, 2H), 3.92 (s, 2H), 3.88 (q, J = 7.9 Hz, 1H), 3.75 (td, J = 8.3, 4.7 Hz, 1H), 3.69 (s, 2H), 2.83-2.71 (m, 1H), 2.38-2.18 (m, 4H), 2.13-2.01 (m, 1H), 1.90-1.78 (m, 2H), 1.15-0.94 (m, 4H). |
| 27 | MS (ESI) m/z: 519.2 (M + H)$^+$; EC$_{50}$ = 158; $^1$H NMR (400 MHz, METHANOL-d4) δ 8.79 (s, 2H), 8.23 (s, 1H), 8.12 (br d, J = 9.02 Hz, 1H), 7.20 (dd, J = 2.20, 9.24 Hz, 1H), 6.57 (d, J = 2.42 Hz, 1H), 6.08-6.23 (m, 1H), 5.62 (dd, J = 7.48, 16.07 Hz, 1H), 4.97 (s, 2H), 4.09 (s, 2H), 3.86 (s, 2H), 3.57-3.61 (m, 3H), 2.93 (br d, J = 7.70 Hz, 1H), 2.42-2.53 (m, 2H), 2.26-2.33 (m, 1H), 1.95-2.05 (m, 2H), 1.20 (ddd, J = 2.64, 5.67, 13.26 Hz, 4H). |
| 28 | MS (ESI) m/z: 578.2 (M + H)$^+$; EC$_{50}$ = 1634; $^1$H NMR (500 MHz, METHANOL-d$_4$) δ 8.76 (s, 2H), 8.29 (br d, J = 8.80 Hz, 1H), 7.94 (s, 1H), 7.15 (d, J = 9.63 Hz, 1H), 6.13 (d, J = 15.41 Hz, 1H), 5.62 (dd, J = 7.15, 15.96 Hz, 1H), 4.46 (s, 2H), 4.26 (br s, 2H), 4.23-4.25 (m, 3H), 2.93 (br d, J = 7.98 Hz, 1H), 2.45-2.52 (m, 2H), 2.25-2.34 (m, 1H), 2.02-2.11 (m, 2H), 1.20-1.24 (m, 2H), 1.17 (br dd, J = 1.93, 4.95 Hz, 2H). |

Example 29

(E)-5-((6-(2-(5-Cyclopropyl-3-(3,5-dichloropyridin-4-yl)isoxazol-4-yl)vinyl) spiro[3,3] heptan-2-yl)methoxy)-3-methylpicolinic acid (29)

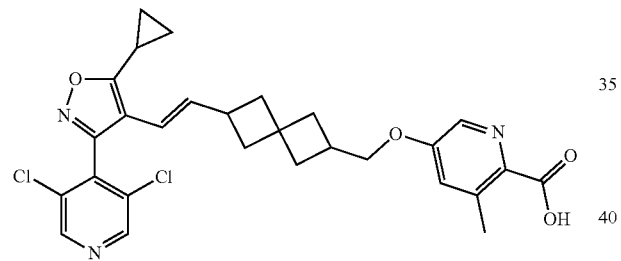

Step 29A. Spiro[3,3] heptane-2,6-dimethanol

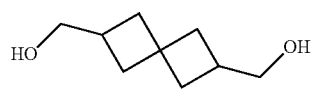 [SMILES: OCC1CC2(C1)CC(CO)C2]

To a cooled solution of diethyl spiro[3.3]heptane-2,6-dicarboxylate (5 g, 20.81 mmol) in THF (60 mL) at −78° C. was added 1M LAH in THF (41.6 mL, 41.6 mmol) dropwise over 10 min period. After addition, the cold bath was removed and the resulting solution was allowed to warm to RT and kept at RT for 30 min. The reaction was cooled to 0° C. and quenched by addition of EtOAc (100 mL), followed by 1N HCl (50 mL). The layers were separated and the aqueous layer was extracted with EtOAc (4×100 mL). The combined organic layers were washed with brine, dried over Na$_2$SO$_4$, filtered, and concentrated. The resulting residue was purified by flash chromatography (40 g silica gel cartridge, eluting with 0-100% EtOAc/Hex) to give spiro [3.3]heptane-2,6-diyldimethanol (2870 mg, 18.37 mmol, 88% yield) as a colorless oil. MS (ESI) m/z: 313.2 (2M+H)$^+$; $^1$H NMR (500 MHz, chloroform-d) δ 3.56 (d, J=6.9 Hz, 4H), 2.37 (td, J=7.5, 14.9 Hz, 2H), 2.15 (ddd, J=3.3, 8.0, 11.3 Hz, 2H), 2.01 (ddd, J=3.3, 8.0, 11.5 Hz, 2H), 1.78 (dd, J=7.4, 11.3 Hz, 2H), 1.70 (dd, J=7.6, 11.4 Hz, 2H), 1.23 (br s, 2H).

Step 29B. (6-(((tert-butyldiphenylsilyl)oxy)methyl) spiro[3.3]heptan-2-yl)methanol

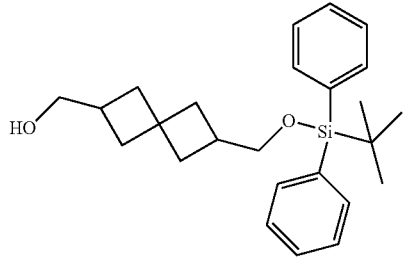 [SMILES: CC(C)(C)[Si](OCC1CC2(CC(CO)C2)C1)(c1ccccc1)c1ccccc1]

To a stirred suspension of spiro[3.3]heptane-2,6-diyldimethanol (3090 mg, 19.78 mmol) and imidazole (1616 mg, 23.73 mmol) in THF (50 mL) at RT was added a solution of tert-butylchloro diphenylsilane (5165 mg, 18.79 mmol) in THF (50 mL). The reaction mixture was stirred at RT for 4 hrs. The reaction mixture was concentrated. The residue was diluted with H$_2$O, extracted with EtOAc (2×). The combined organic layers were washed with brine, dried (Na$_2$SO$_4$), and concentrated under reduced pressure. The residue was purified by flash chromatography (120 g silica gel cartridge, eluting with 0-100% EtOAc/Hexanes) to afford (6-(((tert-butyldiphenylsilyl)oxy)methyl)spiro[3.3]heptan-2-yl) methanol (3700 mg, 9.38 mmol, 47.4% yield) as a white solid. MS (ESI) m/z: 417.2 (M+Na)+; $^1$H NMR (500 MHz, chloroform-d) δ 7.72-7.59 (m, 4H), 7.47-7.34 (m, 6H), 3.66-3.49 (m, 4H), 2.48-2.28 (m, 2H), 2.21-2.04 (m, 2H), 1.94 (ddd, J=3.3, 8.2, 11.3 Hz, 2H), 1.88-1.70 (m, 3H), 1.68-1.51 (m, 1H), 1.18 (br s, 1H), 1.05 (s, 9H).

Step 29C. 6-(((tert-butyldiphenylsilyl)oxy)methyl) spiro[3.3]heptane-2-carbaldehyde

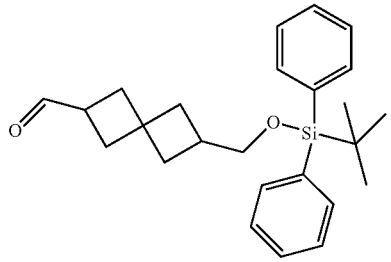 [SMILES: CC(C)(C)[Si](OCC1CC2(CC(C=O)C2)C1)(c1ccccc1)c1ccccc1]

To a solution of (6-(((tert-butyldiphenylsilyl)oxy)methyl) spiro[3.3]heptan-2-yl)methanol (1500 mg, 3.80 mmol) in CH$_2$Cl$_2$ (15 mL) at RT was added Dess-Martin periodinane (1612 mg, 3.80 mmol) in CH$_2$Cl$_2$ (10 mL) dropwise. The mixture was stirred at RT for 20 min. The mixture was concentrated and purified by flash chromatography (40 g silica gel cartridge, eluting with 0-70% EtOAc/Hexanes) to give 6-(((tert-butyldiphenylsilyl)oxy)methyl)spiro[3.3]heptane-2-carbaldehyde (1178 mg, 79% yield) as a white foam. MS (ESI) m/z: 393.1 (M+H)$^+$; $^1$H NMR (400 MHz, chloroform-d) δ 9.69 (d, J=2.2 Hz, 1H), 7.71-7.59 (m, 4H), 7.50-7.33 (m, 6H), 3.57 (br d, J=6.2 Hz, 2H), 3.14-2.85 (m, 1H), 2.46-2.17 (m, 3H), 2.16-2.00 (m, 3H), 1.98-1.71 (m, 3H), 1.11-1.02 (m, 9H).

Step 29D. (E)-4-(2-(6-(((tert-butyldiphenylsilyl)oxy) methyl)spiro[3.3]heptan-2-yl)vinyl)-5-cyclopropyl-3-(3,5-dichloropyridin-4-yl)isoxazole

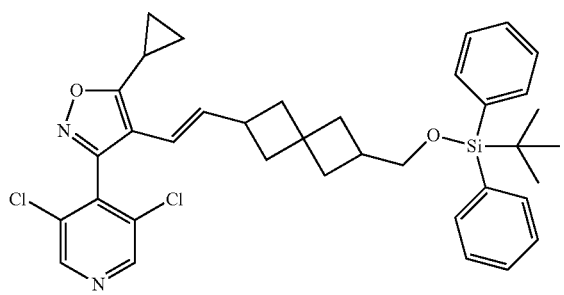 [SMILES: CC(C)(C)[Si](OCC1CC2(CC(/C=C/c3c(-c4c(Cl)cncc4Cl)noc3C3CC3)C2)C1)(c1ccccc1)c1ccccc1]

To a vigorously stirred solution of diethyl ((5-cyclopropyl-3-(3,5-dichloropyridin-4-yl)isoxazol-4-yl)methyl)phosphonate (225 mg, 0.555 mmol) and 6-(((tert-butyldiphenylsilyl) oxy)methyl)spiro[3.3]heptane-2-carbaldehyde (218 mg, 0.555 mmol) in THF (3.7 mL) at −78° C. was added lithium bis(trimethylsilyl)amide (1M in THF) (1222 µl, 1.222 mmol) dropwise over 10 min. The reaction was then allowed to warm up to RT, stirred for 1 hr. 2 mL of MeOH was added, stirred for 10 min, the reaction was concentrated and purified by flash chromatography (24 g silica gel cartridge, eluting with 0-100% EtOAc/hexanes) to afford (E)-4-(2-(6-(((tert-butyldiphenylsilyl)oxy)methyl) spiro[3.3] heptan-2-yl)vinyl)-5-cyclopropyl-3-(3,5-dichloropyridin-4-yl)isoxazole (175 mg, 0.272 mmol, 49.0% yield) as a white foam. MS (ESI) m/z: 643.2 (M+H)$^+$; $^1$H NMR (500 MHz, chloroform-d) δ 8.65 (d, J=0.8 Hz, 2H), 7.68 (br d, J=6.3 Hz, 6H), 7.49-7.35 (m, 4H), 5.90 (dd, J=1.1, 16.2 Hz, 1H), 5.62 (dd, J=7.2, 16.0 Hz, 1H), 3.58 (d, J=6.3 Hz, 2H), 2.87-2.71 (m, 1H), 2.47-2.33 (m, 1H), 2.26-1.97 (m, 4H), 1.92-1.81 (m, 2H), 1.78-1.58 (m, 3H), 1.32-1.22 (m, 2H), 1.20-1.13 (m, 2H), 1.11-1.05 (m, 9H).

Step 29E. (E)-(6-(2-(5-cyclopropyl-3-(3,5-dichloropyridin-4-yl)isoxazol-4-yl)vinyl) spiro[3.3] heptan-2-yl)methanol

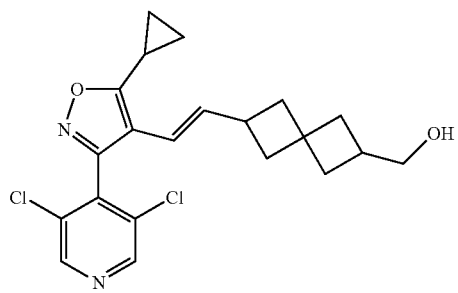 [SMILES: OCC1CC2(CC(/C=C/c3c(-c4c(Cl)cncc4Cl)noc3C3CC3)C2)C1]

To a solution of (E)-4-(2-(6-(((tert-butyldiphenylsilyl) oxy)methyl) spiro[3.3]heptan-2-yl)vinyl)-5-cyclopropyl-3-(3,5-dichloropyridin-4-yl)isoxazole (170 mg, 0.264 mmol) in THF (1.3 mL) was added n-Bu$_4$NF (1.0 M solution in THF, 4.2 mL, 4.2 mmol). The reaction was stirred at RT for 2 hrs and concentrated in vacuo. The residue was purified by column chromatography on silica gel (0-100% EtOAc in hexane) to provide (E)-(6-(2-(5-cyclopropyl-3-(3,5-dichloropyridin-4-yl)isoxazol-4-yl)vinyl)spiro[3.3]heptan-2-yl) methanol (96 mg, 0.237 mmol, 90% yield) as a colorless oil. MS (ESI) m/z: 405.1 (M+H)$^+$; $^1$H NMR (500 MHz, chloroform-d) δ 8.63 (s, 2H), 5.89 (dd, J=1.0, 16.1 Hz, 1H), 5.59 (dd, J=7.2, 16.0 Hz, 1H), 3.54 (d, J=6.6 Hz, 2H), 2.83-2.71 (m, 1H), 2.40-2.29 (m, 1H), 2.24-2.01 (m, 4H), 1.91 (ddd, J=3.3, 8.1, 11.4 Hz, 1H), 1.80-1.57 (m, 4H), 1.28-1.22 (m, 3H), 1.18-1.09 (m, 2H).

Step 29F. Methyl (E)-5-((6-(2-(5-cyclopropyl-3-(3, 5-dichloropyridin-4-yl)isoxazol-4-yl)vinyl)spiro[3.3] heptan-2-yl)methoxy)-3-methylpicolinate

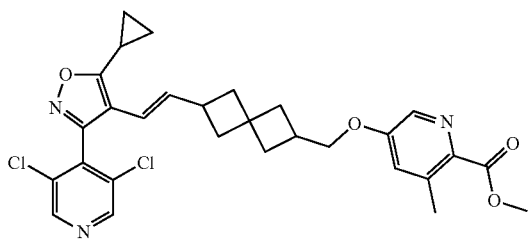 [SMILES: COC(=O)c1ncc(OCC2CC3(CC(/C=C/c4c(-c5c(Cl)cncc5Cl)noc4C4CC4)C3)C2)cc1C]

(E)-(6-(2-(5-cyclopropyl-3-(3,5-dichloropyridin-4-yl) isoxazol-4-yl)vinyl) spiro[3.3]heptan-2-yl)methanol (24 mg, 0.059 mmol), methyl 5-hydroxy-3-methylpicolinate (9.90 mg, 0.059 mmol), Ph$_3$P (20.19 mg, 0.077 mmol) and diisopropyl (E)-diazene-1,2-dicarboxylate (15.16 µl, 0.077 mmol) were dissolved in dry THF (296 µL) and heated at 90° C. in a sealed vial for 2 hrs. After cooling to RT, the reaction mixture was directly purified by column chromatography on silica gel (0-60% EtOAc in hexane) to provide methyl (E)-5-((6-(2-(5-cyclopropyl-3-(3,5-dichloropyridin-4-yl)isoxazol-4-yl)vinyl)spiro[3.3]heptan-2-yl)methoxy)-3-methylpicolinate (32 mg, 0.035 mmol, 58.5% yield) as a white foam. MS (ESI) m/z: 554.1 (M+H)⁺.

Step 29G. Example 29. (E)-5-((6-(2-(5-Cyclopropyl-3-(3,5-dichloropyridin-4-yl)isoxazol-4-yl)vinyl)spiro[3,3] heptan-2-yl)methoxy)-3-methylpicolinic acid To methyl (E)-5-((6-(2-(5-cyclopropyl-3-(3,5-dichloropyridin-4-yl)isoxazol-4-yl)vinyl)spiro[3.3]heptan-2-yl)methoxy)-3-methylpicolinate (32 mg, 0.058 mmol) was added THF (0.5 mL), MeOH (0.1 mL) and water (0.4 mL). The reaction was added lithium hydroxide hydrate (9.69 mg, 0.231 mmol). The reaction mixture was stirred at room temperature for 2 hrs, and then concentrated to remove THF and MeOH. The residue was added water (2 mL), acidified with acetic acid (0.033 mL, 0.577 mmol) to about pH 4. The resulting suspension was extracted with EtOAc (3×). The combined organic extracts were concentrated. The residue was purified by preparative HPLC (Column: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 29% B, 29-69% B over 20 minutes, then a 4-minute hold at 100% B; Flow Rate: 20 mL/min) to afford 12.9 mg (41% yield) of the title compound as a white solid: MS (ESI) m/z: 540.1 (M+H)⁺. ¹H NMR (500 MHz, DMSO-d6) δ 8.86 (d, J=2.4 Hz, 2H), 8.12 (brs, 1H), 7.31 (brs, 1H), 6.06 (brd, J=15.9 Hz, 1H), 5.50 (dd, J=7.5, 16.0 Hz, 1H), 4.00 (brd, J=6.7 Hz, 2H), 2.82-2.72 (m, 1H), 2.58-2.42 (m, 4H), 2.40-2.30 (m, 1H), 2.25-2.03 (m, 3H), 1.96-1.79 (m, 2H), 1.76-1.55 (m, 3H), 1.23-1.14 (m, 2H), 1.11-1.03 (m, 2H).

Examples 30 and 31

(E)-5-((6-(2-(5-Cyclopropyl-3-(2-(trifluoromethyl)phenyl)isoxazol-4-yl)vinyl)spiro [3.3]heptan-2-yl)methoxy)-3-methylpicolinic acid (Enantiomer 1) and (E)-5-((6-(2-(5-Cyclopropyl-3-(2-(trifluoromethyl)phenyl)isoxazol-4-yl)vinyl)spiro [3.3]heptan-2-yl)methoxy)-3-methylpicolinic acid (Enantiomer 2)

(30-31)

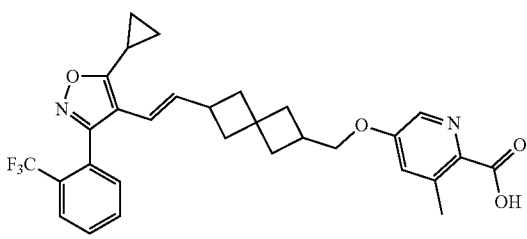

Step 30A. Methyl (E)-5-((6-(2-(5-Cyclopropyl-3-(2-(trifluoromethyl)phenyl)isoxazol-4-yl)vinyl)spiro[3.3]heptan-2-yl)methoxy)-3-methylpicolinate

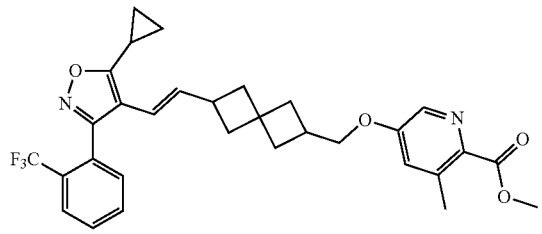 [SMILES: COC(=O)c1ncc(OCC2CC3(CC(/C=C/c4c(-c5ccccc5C(F)(F)F)noc4C4CC4)C3)C2)cc1C]

The title compound was prepared according to the methods described for the synthesis of example I (step 1F), starting from (E)-5-((6-(2-(5-Cyclopropyl-3-(2-(trifluoromethyl) phenyl)isoxazol-4-yl)vinyl)spiro[3,3] heptan-2-yl) methanol and methyl 5-hydroxy-3-methylpicolinate, to give a racemic mixture. MS (ESI) m/z: 553.3 (M+H)⁺.

Step 30B. Methyl (E)-5-((6-(2-(5-Cyclopropyl-3-(2-(trifluoromethyl)phenyl)isoxazol-4-yl)vinyl)spiro [3.3]heptan-2-yl)methoxy)-3-methylpicolinate (Enantiomer 1 & Enantiomer 2)

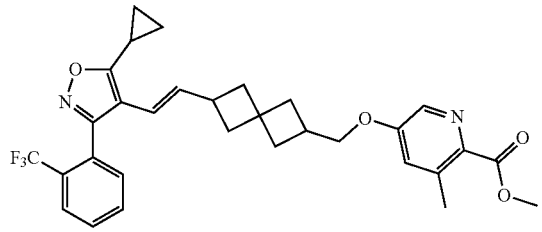 [SMILES: COC(=O)c1ncc(OCC2CC3(CC(/C=C/c4c(-c5ccccc5C(F)(F)F)noc4C4CC4)C3)C2)cc1C]

Methyl (E)-5-((6-(2-(5-Cyclopropyl-3-(2-(trifluoromethyl)phenyl) isoxazol-4-yl)vinyl)spiro[3.3]heptan-2-yl) methoxy)-3-methylpicolinate (100 mg) was separated by SFC (Instrument: PIC Solution SFC prep-200; Column: Chiralpak IC, 30×250 mm, 5 micron; Mobile Phase 20% ACN (0.1% TFA)/80% CO₂; Flow: 85 mL/min, 150 Bar, 40° C.) to afford the first eluent (36 mg) as Enantiomer 1 and the second eluent (35 mg) as Enantiomer 2. Enantiomer 1: MS (ESI) m/z: 553.3 (M+H)⁺; ¹H NMR (500 MHz, CHLOROFORM-d) δ 8.20 (d, J=2.8 Hz, 1H), 7.81 (br d, J=7.7 Hz, 1H), 7.68-7.55 (m, 2H), 7.39 (br d, J=7.2 Hz, 1H), 7.02 (br s, 1H), 5.85 (br d, J=16.2 Hz, 1H), 5.56 (br dd, J=7.2, 16.0 Hz, 1H), 4.09-3.88 (m, 5H), 2.86-2.72 (m, 1H), 2.65-2.55 (m, 4H), 2.26-2.15 (m, 2H), 2.13-2.04 (m, 2H), 2.02-1.84 (m, 2H), 1.81-1.62 (m, 3H), 1.31-1.20 (m, 2H), 1.15-1.05 (m, 2H). Enantiomer 2: MS (ESI) m/z: 553.3 (M+H)⁺; ¹H NMR (500 MHz, CHLOROFORM-d) δ 8.20 (d, J=2.8 Hz, 1H), 7.81 (d, J=7.7 Hz, 1H), 7.68-7.55 (m, 2H), 7.39 (d, J=7.4 Hz, 1H), 7.02 (d, J=2.8 Hz, 1H), 5.85 (d, J=16.2 Hz, 1H), 5.56 (dd, J=7.2, 16.0 Hz, 1H), 4.00-3.91 (m, 5H), 2.82-2.71 (m, 1H), 2.66-2.56 (m, 4H), 2.26-2.16 (m, 2H), 2.13-2.04 (m, 2H), 2.02-1.83 (m, 2H), 1.79-1.65 (m, 3H), 1.24-1.19 (m, 2H), 1.15-1.08 (m, 2H).

Step 30C. Example 30. (E)-5-((6-(2-(5-Cyclopropyl-3-(2-(trifluoromethyl)phenyl) isoxazol-4-yl)vinyl)spiro [3.3]heptan-2-yl)methoxy)-3-methylpicolinic acid (Enantiomer 1)

The title compound was prepared according to methods described for the synthesis of example I (step 1G), starting from Methyl (E)-5-((6-(2-(5-Cyclopropyl-3-(2-(trifluoromethyl) phenyl)isoxazol-4-yl) vinyl)spiro [3.3]heptan-2-yl) methoxy)-3-methylpicolinate (Enantiomer 1). MS (ESI) m/z: 539.5 [M+H]$^+$; $^1$H NMR (500 MHz, CHLOROFORM-d) δ 8.06 (d, J=2.5 Hz, 1H), 7.81 (d, J=7.7 Hz, 1H), 7.68-7.57 (m, 2H), 7.39 (d, J=7.4 Hz, 1H), 7.09 (d, J=2.2 Hz, 1H), 5.86 (d, J=16.2 Hz, 1H), 5.57 (dd, J=7.3, 16.1 Hz, 1H), 3.97 (d, J=6.6 Hz, 2H), 2.84-2.70 (m, 4H), 2.67-2.58 (m, 1H), 2.30-2.16 (m, 2H), 2.12-1.96 (m, 3H), 1.90 (dd, J=7.7, 11.3 Hz, 1H), 1.80-1.66 (m, 3H), 1.25-1.19 (m, 2H), 1.16-1.08 (m, 2H).

Step 30D. Example 31. (E)-5-((6-(2-(5-Cyclopropyl-3-(2-(trifluoromethyl)phenyl) isoxazol-4-yl)vinyl)spiro [3.3]heptan-2-yl)methoxy)-3-methylpicolinic acid (Enantiomer 2)

The title compound was prepared according to methods described for the synthesis of example I (step 1G), starting from Methyl (E)-5-((6-(2-(5-Cyclopropyl-3-(2-(trifluoromethyl) phenyl)isoxazol-4-yl) vinyl)spiro [3.3]heptan-2-yl) methoxy)-3-methylpicolinate (Enantiomer 2). MS (ESI) m/z: 539.5 [M+H]$^+$; EC50=139; 1H NMR (500 MHz, CHLOROFORM-d) δ=8.06 (d, J=2.2 Hz, 1H), 7.81 (d, J=7.7 Hz, 1H), 7.66-7.56 (m, 2H), 7.39 (d, J=7.4 Hz, 1H), 7.08 (d, J=1.9 Hz, 1H), 5.86 (d, J=16.0 Hz, 1H), 5.57 (dd, J=7.3, 16.1 Hz, 1H), 3.97 (d, J=6.3 Hz, 2H), 2.83-2.71 (m, 4H), 2.67-2.58 (m, 1H), 2.28-2.17 (m, 2H), 2.13-1.97 (m, 3H), 1.90 (br dd, J=7.7, 11.3 Hz, 1H), 1.80-1.65 (m, 3H), 1.25-1.19 (m, 2H), 1.15-1.08 (m, 2H).

Example 32

(E)-5-((6-(2-(5-Cyclopropyl-3-(2-(trifluoromethyl)phenyl)isoxazol-4-yl)vinyl)spiro[3,3]heptan-2-yl)methoxy)-3-isopropoxypicolinic acid Step 32A. (E)-5-((6-(2-(5-Cyclopropyl-3-(2-(trifluoromethyl)phenyl)isoxazol-4-yl)vinyl) spiro[3,3] heptan-2-yl)methoxy)-3-isopropoxypicolinonitrile

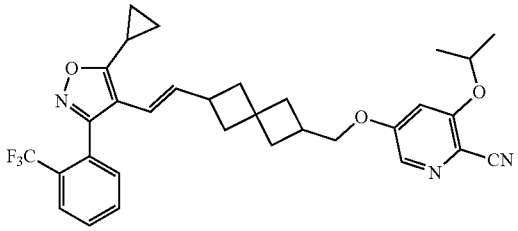 [SMILES: CC(C)Oc1cc(OCC2CC3(CC(/C=C/c4c(-c5ccccc5C(F)(F)F)noc4C4CC4)C3)C2)cnc1C#N]

The title compound was prepared according to methods described for the synthesis of example I (step 1F), starting from (E)-5-((6-(2-(5-Cyclopropyl-3-(2-(trifluoromethyl) phenyl)isoxazol-4-yl)vinyl)spiro[3,3] heptan-2-yl)methanol and 5-hydroxy-3-isopropoxypicolinonitrile. MS (ESI) m/z: 564.2 (M+H)$^+$.

Step 32B. Example 32. (E)-5-((6-(2-(5-Cyclopropyl-3-(2-(trifluoromethyl)phenyl) isoxazol-4-yl)vinyl)spiro[3,3] heptan-2-yl)methoxy)-3-isopropoxypicolinic acid To a stirred solution of (E)-5-((6-(2-(5-cyclopropyl-3-(2-(trifluoromethyl)phenyl) isoxazol-4-yl)vinyl)spiro[3.3]heptan-2-yl)methoxy)-3-isopropoxypicolinonitrile (26 mg, 0.032 mmol) in ethanol (2 mL) was added NaOH (0.065 mL, 0.323 mmol) and the reaction was heated to 100° C. for 1 hr. The reaction was concentrated, 2 mL of H$_2$O was added, then acidified with acetic acid to about pH 4. The resulting suspension was extracted with EtOAc (3×). The combined organic extracts were conc, the residue was purified by preparative HPLC (Column: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 29% B, 29-69% B over 20 minutes, then a 4-minute hold at 100% B; Flow Rate: 20 mL/min) to afford the title compound (7.1 mg, 37% yield). MS (ESI) m/z: 583.1 (M+H)$^+$. $^1$H NMR (500 MHz, DMSO-d6) δ 7.94-7.88 (m, 1H), 7.85-7.71 (m, 3H), 7.48 (br d, J=7.3 Hz, 1H), 7.06 (s, 1H), 5.93 (d, J=16.1 Hz, 1H), 5.50 (dd, J=7.4, 16.1 Hz, 1H), 4.69 (td, J=6.0, 11.9 Hz, 1H), 4.00 (br d, J=6.5 Hz, 2H), 2.80-2.69 (m, 1H), 2.57-2.43 (m, 1H), 2.31-2.23 (m, 1H), 2.21-2.02 (m, 3H), 1.95-1.79 (m, 2H), 1.75-1.55 (m, 3H), 1.26 (d, J=6.0 Hz, 6H), 1.19-1.09 (m, 2H), 1.07-1.00 (m, 2H).

Example 33

(E)-5-((6-(2-(5-Cyclopropyl-3-(2-(trifluoromethyl)phenyl)isoxazol-4-yl)vinyl)spiro[3,3]heptan-2-yl)methoxy)-3-isopropoxypicolinamide (32)

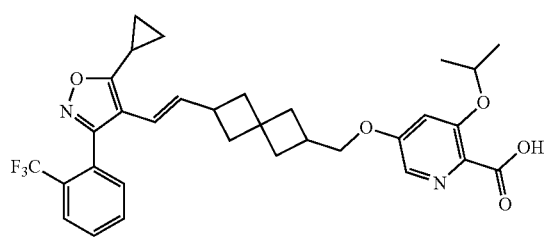

(33)

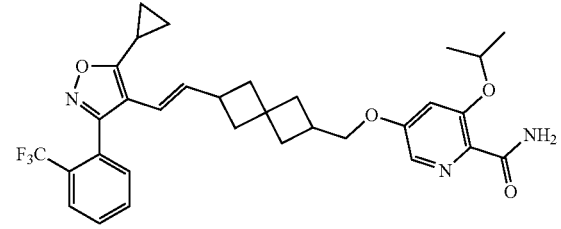

The title compound (1.1 mg, 6% yield) was obtained as a side product during the synthesis of Example 32 (step 32B). MS (ESI) m/z: 582.1 (M+H)+. 1H NMR (500 MHz, DMSO-d6) δ 7.97-7.89 (m, 1H), 7.86-7.72 (m, 3H), 7.55-7.41 (m, 2H), 7.21 (br s, 1H), 7.07 (s, 1H), 5.96 (br d, J=15.9 Hz, 1H), 5.45 (br dd, J=7.5, 16.0 Hz, 1H), 4.78-4.63 (m, 1H), 3.99 (br d, J=6.7 Hz, 2H), 2.78-2.68 (m, 1H), 2.60-2.48 (m, 1H), 2.35-2.22 (m, 1H), 2.19-1.97 (m, 3H), 1.93-1.73 (m, 2H), 1.69-1.52 (m, 3H), 1.26 (br d, J=5.8 Hz, 6H), 1.17-1.10 (m, 2H), 1.07-1.00 (m, 2H).

Intermediates

Preparation of Intermediate for Example 54. Ethyl 7-hydroxycinnoline-3-carboxylate

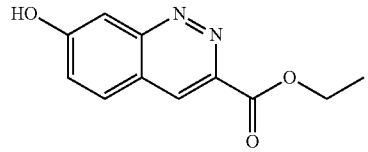 [SMILES: CCOC(=O)c1cc2ccc(O)cc2nn1]

Step 54A. Ethyl 7-(4,4,5,5-tetramethyl-1,3,2-dioxaborolan-2-yl)cinnoline-3-carboxylate

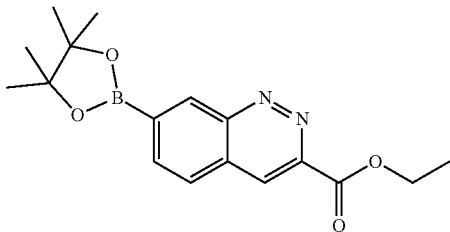 [SMILES: CCOC(=O)c1cc2ccc(B3OC(C)(C)C(C)(C)O3)cc2nn1]

A mixture of ethyl 7-chlorocinnoline-3-carboxylate (616 mg, 2.60 mmol), 4,4,4',4',5,5,5',5'-octamethyl-2,2'-bi(1,3,2-dioxaborolane) (859 mg, 3.38 mmol) and potassium acetate (766 mg, 7.81 mmol) in dioxane (13 mL) was sparged with nitrogen while stirring for 2 min. PdCl2(dppf) (381 mg, 0.521 mmol) was then added and the reaction stirred at 100° C. for 1 hr. After cooling to room temperature, diluted with H2O, extracted with EtOAc (3×), the combined organic extracts were washed with brine, dried (Na2SO4), filtered and concentrated. The resulting residue was purified by column chromatography (40 g silica gel cartridge, eluting with 0-100% EtOAc/hexanes, then 0-10% MeOH/EtOAc to afford ethyl 7-(4,4,5,5-tetramethyl-1,3,2-dioxaborolan-2-yl)cinnoline-3-carboxylate (260 mg, 0.792 mmol, 30.4% yield) as a brownish oil. MS (ESI) m/z: 329.0 (M+H)+.

Step 54B. Ethyl 7-hydroxycinnoline-3-carboxylate

NaOH (1.585 mL, 1.585 mmol), followed by H2O2 (0.243 mL, 2.377 mmol) were added to a 0° C. solution of ethyl 7-(4,4,5,5-tetramethyl-1,3,2-dioxaborolan-2-yl)cinnoline-3-carboxylate (260 mg, 0.792 mmol) in THF (4 mL). The reaction was maintained at 0° C. After 15 minutes, the reaction was diluted with EtOAc and quenched with aqueous Na2SO3, and washed with water and brine. The combined aqueous layers were back extracted with EtOAc and the combined organics were dried over Na2SO4, filtered and concentrated to dryness. The residue was purified by column chromatography (24 g silica gel cartridge, eluting with 0-100% EtOAc/Hex) to afford title compound (45 mg, 0.206 mmol, 26.0% yield) as a light yellow solid. MS (ESI) m/z: 219.0 (M+H)+. 1H NMR (500 MHz, METHANOL-d4) 6.73 (s, 1H), 8.06 (d, J=9.1 Hz, 1H), 7.72 (d, J=1.9 Hz, 1H), 7.59-7.45 (m, 1H), 4.55 (q, J=7.2 Hz, 2H), 1.49 (t, J=7.2 Hz, 3H).

Preparation of Intermediate for Example 32. 5-hydroxy-3-isopropoxypicolinonitrile

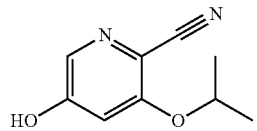

Step A. Intermediate 32A. 5-fluoro-3-isopropoxypicolinonitrile

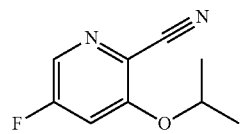

To a stirred solution of sodium isopropoxide (82 mg, 1.0 mmol) in 2-propanol (2 mL) was added 3,5-difluoropicolinonitrile (140 mg, 1.0 mmol) in 2-propanol (2 mL). The reaction was stirred at rt for 1 hr. An additional amount of sodium isopropoxide (30 mg) was added and reaction was completed after 20 min. The reaction mixture was concentrated and diluted with EtOAc. The organic layer was washed with H2O, dried over MgSO4, filtered and concentrated. The crude product was purified by flash column chromatography (40 g silica gel cartridge; A=Hex, B=EtOAc; 20 min grad.; 0% B to 100% B; flow rate=40 mL/min). Fractions containing the desired product were combined, concentrated and dried in vacuo to afford the title compound (60 mg, 0.33 mmol, 33% yield) as a clear liquid. MS (ESI) 180.3 (M+H)+. 1H NMR (500 MHz, CHLOROFORM-d) δ 8.15 (d, J=2.2 Hz, 1H), 7.09 (dd, J9.6, 2.2 Hz, 1H), 4.65 (dt, J12.1, 6.1 Hz, 1H), 1.47 (d, J6.1 Hz, 6H).

Step B. Intermediate 32B. 5-(tert-butoxy)-3-isopropoxypicolinonitrile

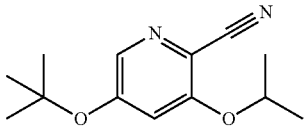 [SMILES: CC(C)Oc1cc(OC(C)(C)C)cnc1C#N]

To a stirred solution of Intermediate 2A (62 mg, 0.34 mmol) in THF (1 mL) at 0° C. was added sodium tert-butoxide (0.38 mL, 0.38 mmol) (1 M in THF). The mixture was warmed to rt and stirred for 2 h. The reaction mixture was concentrated and diluted with EtOAc. The organic layer was washed with H₂O, dried over MgSO4, filtered and concentrated. The crude product was purified by flash column chromatography (12 g silica gel cartridge; A=Hex, B=EtOAc; 15 min grad.; 0% B to 100% B; flow rate=12 mL/min). Fractions containing the desired product were combined, concentrated and dried in vacuo to afford the title compound (70 mg, 0.30 mmol, 87% yield) as a clear liquid. MS (ESI) 235.2 (M+H)⁺. ¹H NMR (400 MHz, CHLOROFORM-d) δ 7.98 (d, J=2.2 Hz, 1H), 6.87 (d, J=1.8 Hz, 1H), 4.65-4.52 (m, 1H), 1.45 (s, 9H), 1.42 (d, J=6.2 Hz, 6H).

Step C. Intermediate 32C.
5-hydroxy-3-isopropoxypicolinonitrile

To a stirred solution of Intermediate 2B (70 mg, 0.30 mmol) in DCM (6 mL) was added TFA (0.23 mL, 3.0 mmol). The reaction was stirred for 2 h. The reaction mixture was concentrated and diluted with EtOAc. The organic layer was washed with H₂O, dried over MgSO₄, filtered and concentrated. The crude product was purified by flash column chromatography (12 g silica gel cartridge; A=Hex, B=EtOAc; 15 min grad.; 0% B to 100% B; flow rate=12 mL/min). Fractions containing the desired product were combined, concentrated and dried in vacuo to afford the title compound (40 mg, 0.22 mmol, 75% yield) as a clear liquid. MS (ESI) 179.2 (M+H)⁺. ¹H NMR (500 MHz, CHLOROFORM-d) δ 7.93 (d, J=1.7 Hz, 1H), 6.96 (d, J=1.9 Hz, 1H), 4.68 (spt, J=6.1 Hz, 1H), 1.44 (d, J6.1 Hz, 6H).

Preparation of Intermediate for Example 62.
3-Cyclobutoxy-5-hydroxypicolinonitrile

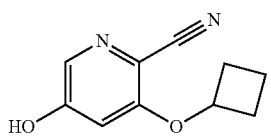

Step A. Intermediate 62A.
5-Bromo-3-cyclobutoxypicolinonitrile

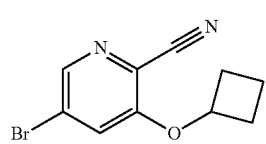

To a stirred solution of 5-bromo-3-nitropicolinonitrile (150 mg, 0.658 mmol) in cyclobutanol (474 mg, 6.58 mmol) was added NaOH (395 µL, 1.974 mmol). The reaction mixture was warmed to 60° C. for 20 min. After cooling to RT, the reaction mixture was concentrated in vacuo and diluted with EtOAc. The organic layer was washed with 1M HCl. The organic layer was dried over MgSO4, filtered and concentrated in vacuo. The crude product was added to a silica gel (24 g) column and was eluted with 0-70% EtOAc in hexanes to give the title compound (85 mg, 0.336 mmol, 51.0% yield) as a light yellow solid. MS (ESI) 253.1 (M+H)⁺. ¹H NMR (400 MHz, CHLOROFORM-d) δ 8.32 (d, J=1.8 Hz, 1H), 7.34 (d, J=1.8 Hz, 1H), 4.79-4.69 (m, 1H), 2.59-2.46 (m, 2H), 2.39-2.24 (m, 2H), 2.04-1.91 (m, 1H), 1.84-1.69 (m, 1H).

Step B. Intermediate 62B.
3-Cyclobutoxy-5-hydroxypicolinonitrile

To a stirred solution of Intermediate 3A (85 mg, 0.336 mmol) in DMSO (672 µL) was added acetohydroxamic acid (76 mg, 1.008 mmol) and K₂CO₃ (232 mg, 1.679 mmol). The reaction mixture was heated to 80° C. for 2 hrs. The reaction mixture was cooled, concentrated and diluted with EtOAc. The organic layer was washed with H₂O, dried over MgSO4, filtered and concentrated. The crude product was purified by flash column chromatography (12 g silica gel cartridge; A=Hex, B=EtOAc; 15 min grad.; 0% B to 70% B; flow rate=24 mL/min). Fractions containing the desired product were combined, concentrated and dried in vacuo to afford the title compound (63 mg, 0.331 mmol, 98% yield) as a white solid. MS (ESI) 191.2 (M+H)⁺. ¹H NMR (400 MHz, CHLOROFORM-d) δ=7.90 (d, J=2.4 Hz, 1H), 6.76 (d, J=2.2 Hz, 1H), 4.78-4.67 (m, 1H), 2.59-2.41 (m, 2H), 2.35-2.19 (m, 2H), 2.00-1.87 (m, 1H), 1.82-1.65 (m, 1H).

Preparation of Intermediate for Example 59. Ethyl 3-hydroxy-1-isopropyl-4-methyl-1H-pyrazole-5-carboxylate

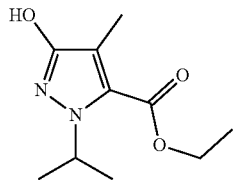

Step A. Intermediate 59A. Ethyl 4-methyl-5-oxo-2,5-dihydro-1H-pyrazole-3-carboxylate

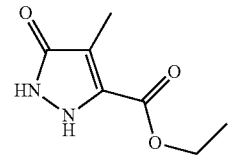

The title compound was prepared according to methods described in Organic Letters, 16(23), 6120-6123; 2014.

Step B. Intermediate 59B. Ethyl 3-((tert-butyldimethylsilyl)oxy)-4-methyl-1H-pyrazole-5-carboxylate

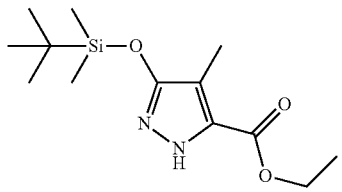 [SMILES: CCOC(=O)c1[nH]nc(O[Si](C)(C)C(C)(C)C)c1C]

TBDMS-Cl (1329 mg, 8.81 mmol) and imidazole (640 mg, 9.40 mmol) were added to a stirred suspension of 5A (1000 mg, 5.88 mmol) in acetonitrile (14 mL). The reaction was stirred at rt for 1 hr. The reaction mixture was concentrated. The residue was diluted with $H_2O$, extracted with EtOAc (2×). The combined organic layers were washed with brine, dried ($Na_2SO_4$), and concentrated under reduced pressure. The residue was purified by flash column chromatography (40 g silica gel cartridge, eluting with 0-30% EtOAc/hexanes). The fractions of desired product were collected to afford ethyl 3-((tert-butyldimethylsilyl)oxy)-4-methyl-1H-pyrazole-5-carboxylate (1.34 g, 4.71 mmol, 80% yield) as a white solid. MS (ESI) 285.2 (M+H)$^+$. $^1$H NMR (500 MHz, DMSO-d6) δ 4.37 (q, J=7.2 Hz, 2H), 2.13 (s, 3H), 1.39 (t, J=7.2 Hz, 3H), 1.00 (s, 9H), 0.27 (s, 6H).

Step C. Intermediate 59C. Ethyl 3-((tert-butyldimethylsilyl)oxy)-1-isopropyl-4-methyl-1H-pyrazole-5-carboxylate

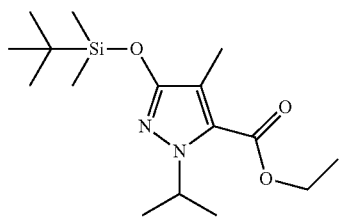 [SMILES: CCOC(=O)c1c(C)c(O[Si](C)(C)C(C)(C)C)nn1C(C)C]

Methyl 3-((tert-butyldimethylsilyl)oxy)-4-methyl-1H-pyrazole-5-carboxylate (120 mg, 0.444 mmol), propan-2-ol (53.3 mg, 0.888 mmol), $Ph_3P$ (210 mg, 0.799 mmol) and diisopropyl (E)-diazene-1,2-dicarboxylate (157 µL, 0.799 mmol) were dissolved in dry THF (2219 µL) and heated at 100° C. in a sealed vial for 16 hrs. After cooling to Rt, the reaction mixture was directly purified by flash column chromatography (12 g, eluting with 0-60% EtOAc/Hex) to give ethyl 3-((tert-butyldimethylsilyl)oxy)-1-isopropyl-4-methyl-1H-pyrazole-5-carboxylate (145 mg, 0.444 mmol, 100% yield) as a colorless oil. MS (ESI) 327.2 (M+H)$^+$. $^1$H NMR (500 MHz, CHLOROFORM-d) δ 5.42-5.20 (m, 1H), 4.33 (d, J=7.2 Hz, 2H), 2.07 (s, 3H), 1.38 (d, J=6.6 Hz, 6H), 1.30-1.24 (m, 3H), 0.99 (s, 9H), 0.25 (s, 6H).

Step D. Intermediate 59. Ethyl 3-hydroxy-1-isopropyl-4-methyl-1H-pyrazole-5-carboxylate To a solution of ethyl 3-((tert-butyldimethylsilyl)oxy)-1-isopropyl-4-methyl-1H-pyrazole-5-carboxylate (145 mg, 0.444 mmol) in THF (2 mL) was added TBAF (0.666 mL, 0.666 mmol). The reaction was stirred at Rt for 16 hrs. The reaction was diluted with $H_2O$, extracted with EtOAc (3×). Combined organic extracts were washed with brine, dried ($Na_2SO_4$), filtered and concentrated. The resulting residue was purified by flash column chromatography (12 g silica gel cartridge, eluting with 0-60% EtOAc/Hexanes) to give the title compound (73 mg, 0.344 mmol, 77% yield) as a white solid. MS (ESI) 213.1 (M+H)$^+$. $^1$H NMR (500 MHz, DMSO-d6) δ 9.88 (br s, 1H), 5.36-5.10 (m, 1H), 4.27 (br d, J=6.3 Hz, 2H), 1.99 (br s, 3H), 1.40-1.10 (m, 9H).

Preparation of Intermediate for Example 60. Ethyl 1-cyclopropyl-5-hydroxy-1H-pyrazole-3-carboxylate

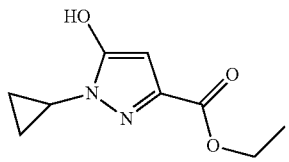

To a suspension of cyclopropylhydrazine dihydrochloride (0.515 g, 3.55 mmol) in THF (3.55 mL) was added $Et_3N$ (1.089 mL, 7.81 mmol) and the mixture stirred at room temperature for 30 min. Then diethyl but-2-ynedioate (0.570 mL, 3.55 mmol) was added and the reaction stirred at 80° C. for 16 hrs. After cooling to RT, salts were filtered off and filtrate was concentrated. The crude product was purified by column chromatography (eluting with 0-100% EtOAc/Hexanes) to give the title compound (150 mg, 0.765 mmol, 21.53% yield). MS (ESI) 197.0 (M+H)$^+$; $^1$H NMR $^1$H NMR (500 MHz, CHLOROFORM-d) δ 11.01 (s, 1H),), 6.16 (s, 1H), 4.35 (d, J=7.2 Hz, 2H), 3.90-3.80 (m, 1H), 1.37 (d, J=7.2 Hz, 3H), 1.13-0.97 (m, 4H).

Preparation of Intermediate for Example 66. methyl 6-hydroxy-4-(4-methylpiperazin-1-yl) quinoline-2-carboxylate

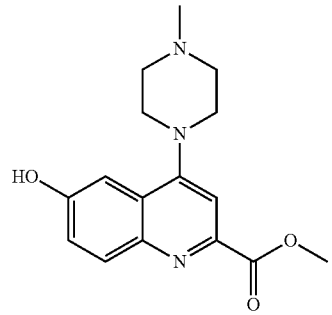 [SMILES: COC(=O)c1cc(N2CCN(C)CC2)c2cc(O)ccc2n1]

Step A. Intermediate 66A. Methyl 6-(benzyloxy)-4-chloroquinoline-2-carboxylate

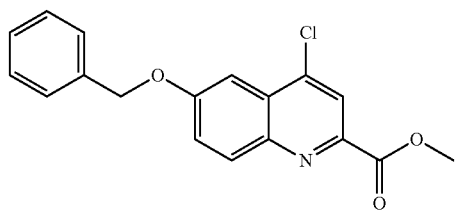 [SMILES: COC(=O)c1cc(Cl)c2cc(OCc3ccccc3)ccc2n1]

Methyl 6-(benzyloxy)-4-hydroxyquinoline-2-carboxylate (400 mg, 1.293 mmol) and phosphoryl trichloride (1216 µL, 12.93 mmol) were heated to 100° C. After 1 hr, the reaction mixture was concentrated, diluted with aqueous potassium phosphate/water, extracted with DCM, and dried over $Na_2SO_4$, filtered and concentrated. The resulting residue was purified by flash column chromatography (24 g silica gel cartridge, eluting with 0-100% EtOAc/Hexanes) to afford methyl 6-(benzyloxy)-4-chloroquinoline-2-carboxylate (370 mg, 1.129 mmol, 87% yield) as a yellow foam. MS (ESI) 328.2 (M+H)+.

Step B. Intermediate 66B. Methyl 6-(benzyloxy)-4-(4-methylpiperazin-1-yl)quinoline-2-carboxylate

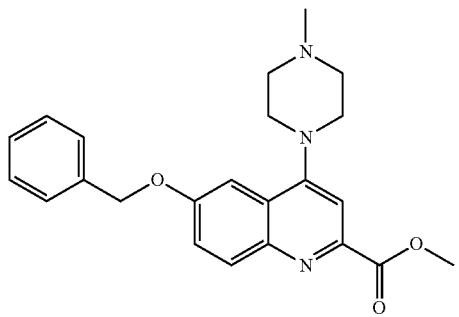 [SMILES: COC(=O)c1cc(N2CCN(C)CC2)c2cc(OCc3ccccc3)ccc2n1]

To a solution of methyl 6-(benzyloxy)-4-chloroquinoline-2-carboxylate (226 mg, 0.690 mmol) in DMF (3 mL) was added 1-methylpiperazine (0.230 mL, 2.069 mmol), followed by Hunig's Base (0.361 mL, 2.069 mmol). The reaction was microwaved at 120 deg. C. for 2 hrs. The reaction mixture was diluted with EtOAc and washed with water (5×) and brine, dried (MgSO4), and concentrated. The crude product was purified by flash column chromatography (12 g silica gel cartridge, eluting with 20-100% EtOAc/Hex, then 0-10% MeOH/EtOAc) to give methyl 6-(benzyloxy)-4-(4-methylpiperazin-1-yl)quinoline-2-carboxylate (45 mg, 0.115 mmol, 16.67% yield) as a pale beige solid. MS (ESI) 392.0 (M+H)+.

Step C. Intermediate 66. Methyl 6-hydroxy-4-(4-methylpiperazin-1-yl)quinoline-2-carboxylate To a solution of methyl 6-(benzyloxy)-4-(4-methylpiperazin-1-yl)quinoline-2-carboxylate (65 mg, 0.166 mmol) in MeOH (4 mL) was added 10% Pd/C (40 mg, 0.038 mmol). The reaction mixture was stirred under H2 balloon at RT for 1 hr. The reaction mixture was filtered through celite, the filtrate was concentrated to give methyl 6-hydroxy-4-(4-methylpiperazin-1-yl)quinoline-2-carboxylate (41 mg, 0.136 mmol, 82% yield) as a light yellow solid. MS (ESI) 302.0 (M+H)+. 1H NMR (500 MHz, METHANOL-d4) δ 8.03-7.99 (m, 1H), 7.61 (s, 1H), 7.34 (dd, J=2.3, 4.8 Hz, 2H), 4.01 (s, 3H), 3.58-3.51 (m, 2H), 3.49-3.43 (m, 2H), 2.50-2.38 (m, 4H), 2.32 (s, 3H).

The following Examples were prepared according to methods described elsewhere herein using appropriate starting materials, reagents and conditions.

| Ex. No. | Structure | Method |
|---|---|---|
| 34 | 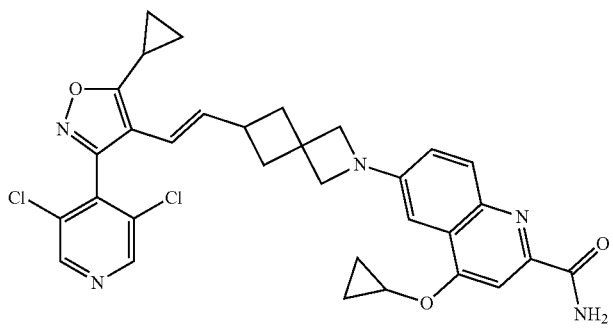<br>(E)-4-cyclopropoxy-6-(6-(2-(5-cyclopropyl-3-(3,5-dichloropyridin-4-yl)isoxazol-4-yl)vinyl)-2-azaspiro[3.3]heptan-2-yl)quinoline-2-carboxamide | Ex. 1 |
| 35 | 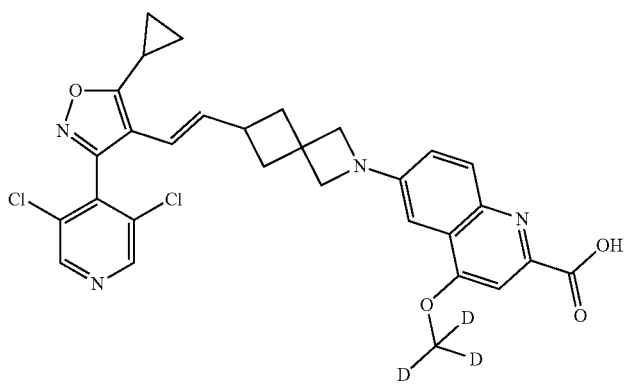<br>(E)-6-(6-(2-(5-cyclopropyl-3-(3,5-dichloropyridin-4-yl)isoxazol-4-yl)vinyl)-2-azaspiro[3.3]heptan-2-yl)-4-(methoxy-d3)quinoline-2-carboxylic acid | Ex. 1 |

| Ex. No. | Structure | Method |
|---|---|---|
| 36 | 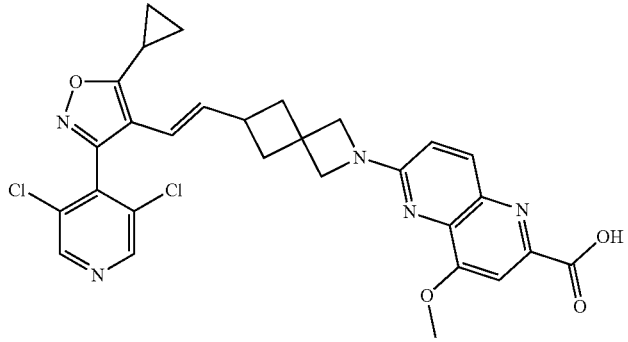<br>(E)-6-(6-(2-(5-cyclopropyl-3-(3,5-dichloropyridin-4-yl)isoxazol-4-yl)vinyl)-2-azaspiro[3.3]heptan-2-yl)-4-methoxy-1,5-naphthyridine-2-carboxylic acid | Ex. 1 |
| 37 | 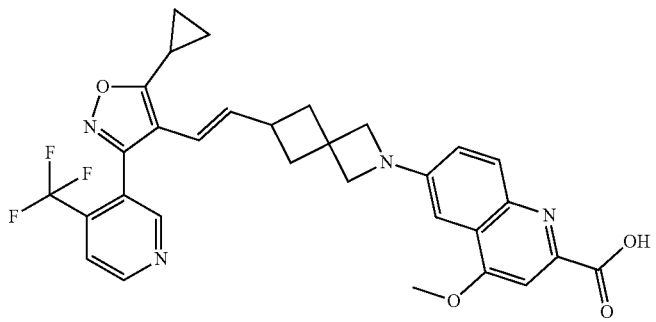<br>(E)-6-(6-(2-(5-cyclopropyl-3-(4-(trifluoromethyl)pyridin-3-yl)isoxazol-4-yl)vinyl)-2-azaspiro[3.3]heptan-2-yl)-4-methoxyquinoline-2-carboxylic acid | Ex. 3 |
| 38 | 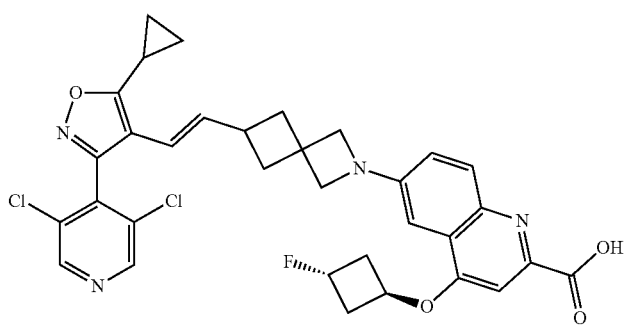<br>6-(6-((E)-2-(5-cyclopropyl-3-(3,5-dichloropyridin-4-yl)isoxazol-4-yl)vinyl)-2-azaspiro[3.3]heptan-2-yl)-4-((1r,3r)-3-fluorocyclobutoxy)quinoline-2-carboxylic acid | Ex. 1 |

| Ex. No. | Structure | Method |
|---|---|---|
| 39 | 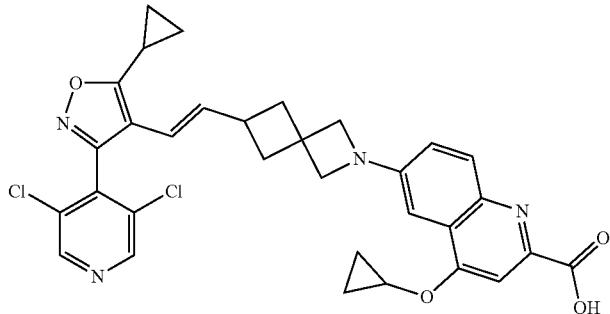<br>(E)-4-cyclopropoxy-6-(6-(2-(5-cyclopropyl-3-(3,5-dichloropyridin-4-yl)isoxazol-4-yl)vinyl)-2-azaspiro[3.3]heptan-2-yl)quinoline-2-carboxylic acid | Ex. 1 |
| 40 | 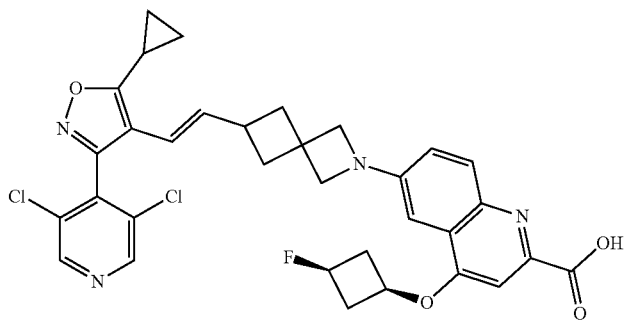<br>6-(6-((E)-2-(5-cyclopropyl-3-(3,5-dichloropyridin-4-yl)isoxazol-4-yl)vinyl)-2-azaspiro[3.3]heptan-2-yl)-4-((1s,3s)-3-fluorocyclobutoxy)quinoline-2-carboxylic acid | Ex. 1 |
| 41 | 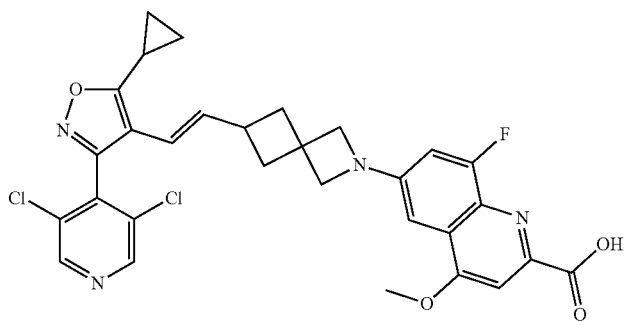<br>(E)-6-(6-(2-(5-cyclopropyl-3-(3,5-dichloropyridin-4-yl)isoxazol-4-yl)vinyl)-2-azaspiro[3.3]heptan-2-yl)-8-fluoro-4-methoxyquinoline-2-carboxylic acid | Ex. 1 |
| 42 | 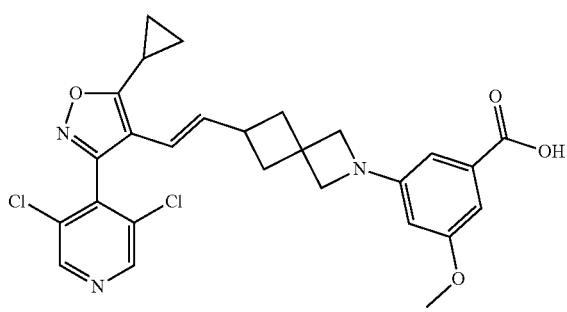<br>(E)-3-(6-(2-(5-cyclopropyl-3-(3,5-dichloropyridin-4-yl)isoxazol-4-yl)vinyl)-2-azaspiro[3.3]heptan-2-yl)-5-methoxybenzoic acid | Ex. 1 |

| Ex. No. | Structure | Method |
|---|---|---|
| 43 | 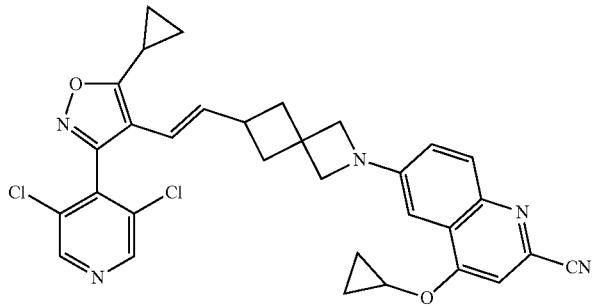<br>(E)-4-cyclopropoxy-6-(6-(2-(5-cyclopropyl-3-(3,5-dichloropyridin-4-yl)isoxazol-4-yl)vinyl)-2-azaspiro[3.3]heptan-2-yl)quinoline-2-carbonitrile | Ex. 1 |
| 44 | 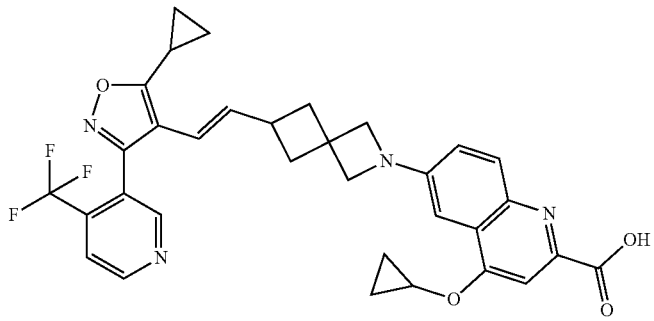<br>(E)-4-cyclopropoxy-6-(6-(2-(5-cyclopropyl-3-(4-(trifluoromethyl)pyridin-3-yl)isoxazol-4-yl)vinyl)-2-azaspiro[3.3]heptan-2-yl)quinoline-2-carboxylic acid | Ex. 3 |
| 45 | 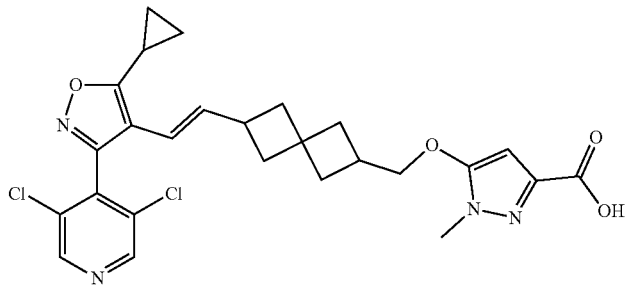<br>(E)-5-((6-(2-(5-cyclopropyl-3-(3,5-dichloropyridin-4-yl)isoxazol-4-yl)vinyl)spiro[3.3]heptan-2-yl)methoxy)-1-methyl-1H-pyrazole-3-carboxylic acid | Ex. 29 |
| 46 | 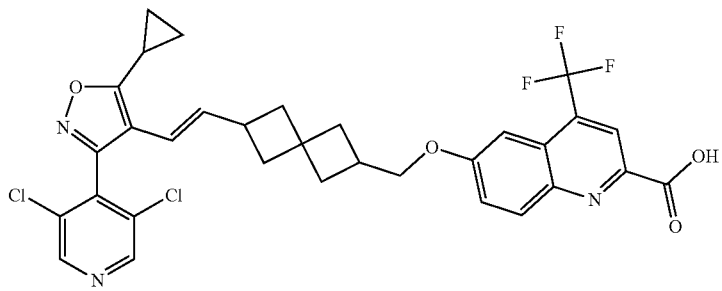<br>(E)-6-((6-(2-(5-cyclopropyl-3-(3,5-dichloropyridin-4-yl)isoxazol-4-yl)vinyl)spiro[3.3]heptan-2-yl)methoxy)-4-(trifluoromethyl)quinoline-2-carboxylic acid | Ex. 29 |

| Ex. No. | Structure | Method |
|---|---|---|
| 47 | 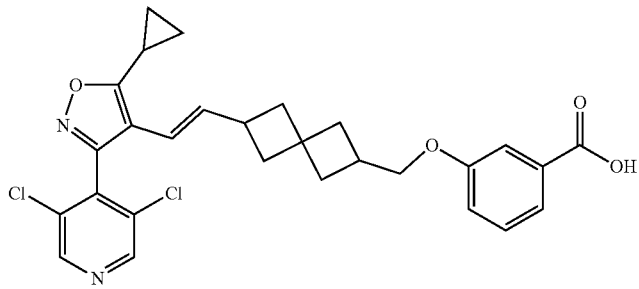<br>(E)-3-((6-(2-(5-cyclopropyl-3-(3,5-dichloropyridin-4-yl)isoxazol-4-yl)vinyl)spiro[3.3]heptan-2-yl)methoxy)benzoic acid | Ex. 29 |
| 48 | 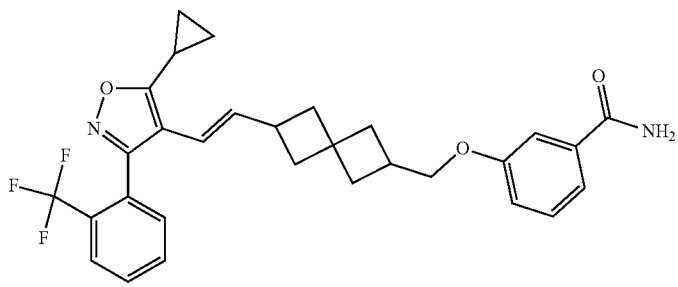<br>(E)-3-((6-(2-(5-cyclopropyl-3-(2-(trifluoromethyl)phenyl)isoxazol-4-yl)vinyl)spiro[3.3]heptan-2-yl)methoxy)benzamide | Ex. 29 |
| 49 | 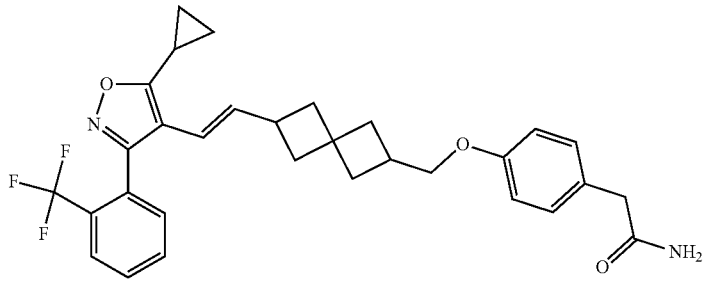<br>(E)-2-(4-((6-(2-(5-cyclopropyl-3-(2-(trifluoromethyl)phenyl) isoxazol-4-yl)vinyl)spiro[3.3]heptan-2-yl)methoxy)phenyl)acetamide | Ex. 29 |
| 50 | 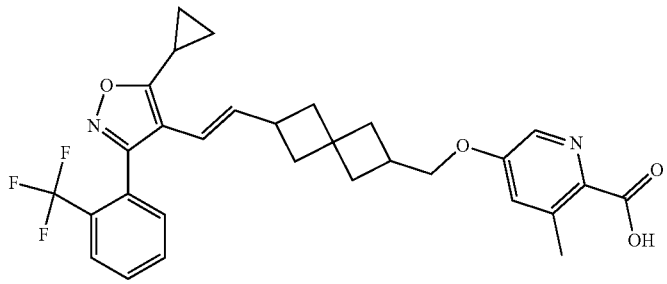<br>(E)-5-((6-(2-(5-cyclopropyl-3-(2-(trifluoromethyl)phenyl)isoxazol-4-yl)vinyl)spiro[3.3]heptan-2-yl)methoxy)-3-methylpicolinic acid | Ex. 29 |

| Ex. No. | Structure | Method |
|---|---|---|
| 51 | 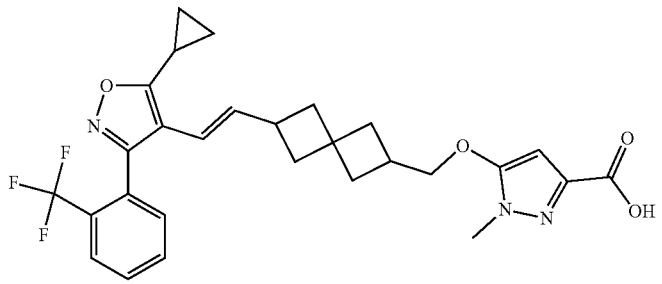<br>(E)-5-((6-(2-(5-cyclopropyl-3-(2-(trifluoromethyl)phenyl)isoxazol-4-yl)vinyl)spiro[3.3]heptan-2-yl)methoxy)-1-methyl-1H-pyrazole-3-carboxylic acid | Ex. 29 |
| 52 | 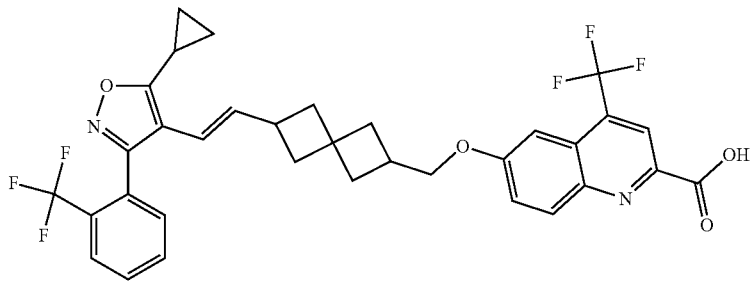<br>(E)-6-((6-(2-(5-cyclopropyl-3-(2-(trifluoromethyl)phenyl)isoxazol-4-yl)vinyl)spiro[3.3]heptan-2-yl)methoxy)-4-(trifluoromethyl)quinoline-2-carboxylic acid | Ex. 29 |
| 53 | 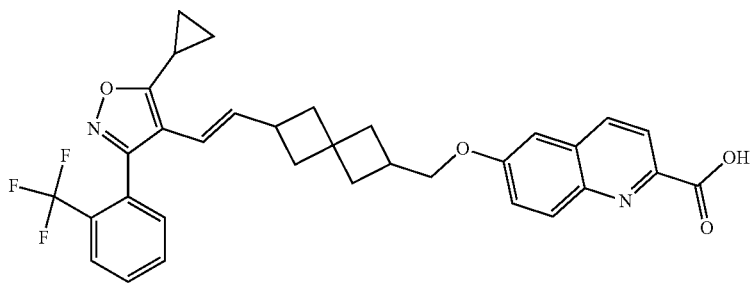<br>(E)-6-((6-(2-(5-cyclopropyl-3-(2-(trifluoromethyl)phenyl)isoxazol-4-yl)vinyl)spiro[3.3]heptan-2-yl)methoxy)quinoline-2-carboxylic acid | Ex. 29 |
| 54 | 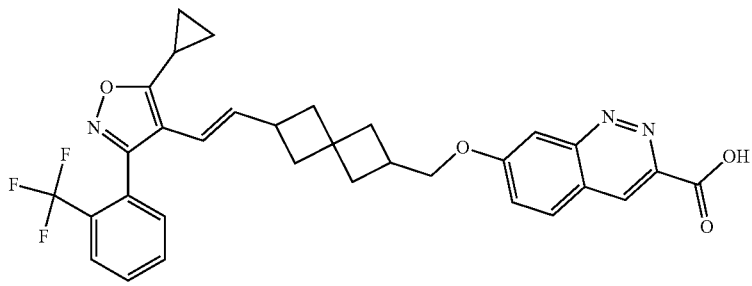<br>(E)-7-((6-(2-(5-cyclopropyl-3-(2-(trifluoromethyl)phenyl)isoxazol-4-yl)vinyl)spiro[3.3]heptan-2-yl)methoxy)cinnoline-3-carboxylic acid | Ex. 29 |

| Ex. No. | Structure | Method |
|---|---|---|
| 55 | 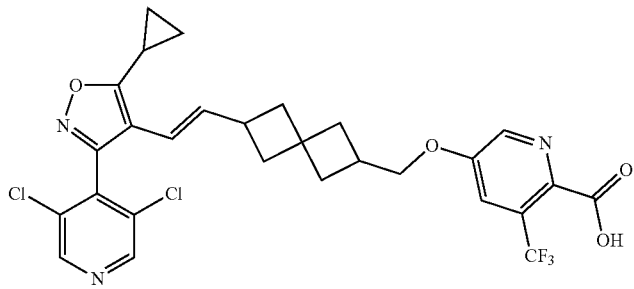<br>(E)-5-((6-(2-(5-cyclopropyl-3-(3,5-dichloropyridin-4-yl)isoxazol-4-yl)vinyl)spiro[3.3]heptan-2-yl)methoxy)-3-(trifluoromethyl)picolinic acid | Ex. 29 |
| 56 | 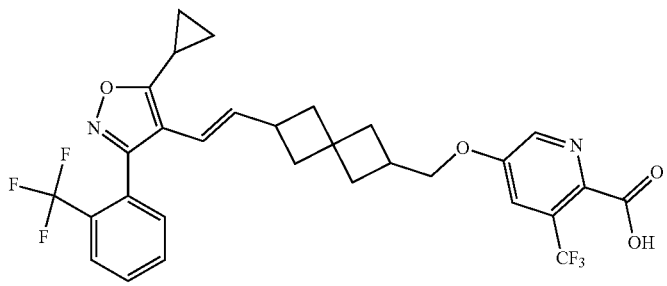<br>(E)-5-((6-(2-(5-cyclopropyl-3-(2-(trifluoromethyl)phenyl)isoxazol-4-yl)vinyl)spiro[3.3]heptan-2-yl)methoxy)-3-(trifluoromethyl)picolinic acid | Ex. 29 |
| 57 | 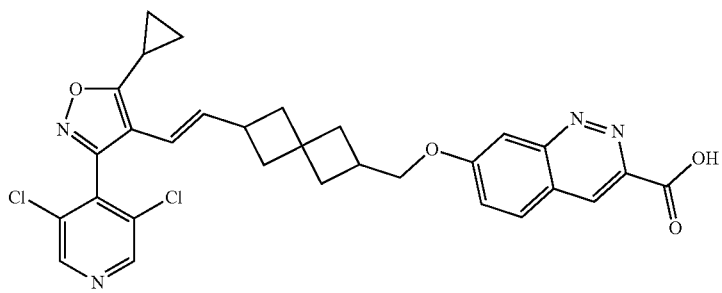<br>(E)-7-((6-(2-(5-cyclopropyl-3-(3,5-dichloropyridin-4-yl)isoxazol-4-yl)vinyl)spiro[3.3]heptan-2-yl)methoxy)cinnoline-3-carboxylic acid | Ex. 29 |
| 58 | 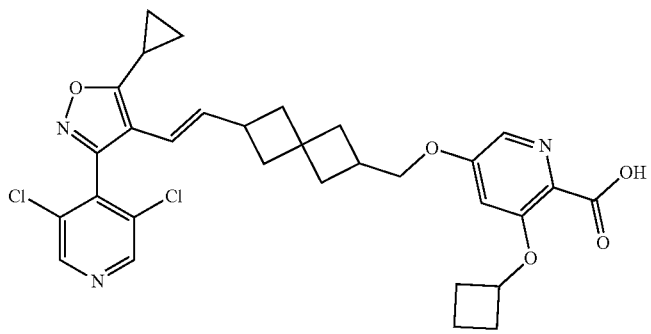<br>(E)-3-cyclobutoxy-5-((6-(2-(5-cyclopropyl-3-(3,5-dichloropyridin-4-yl)isoxazol-4-yl)vinyl)spiro[3.3]heptan-2-yl)methoxy)picolinic acid | Ex. 32 |

| Ex. No. | Structure | Method |
|---|---|---|
| 59 | 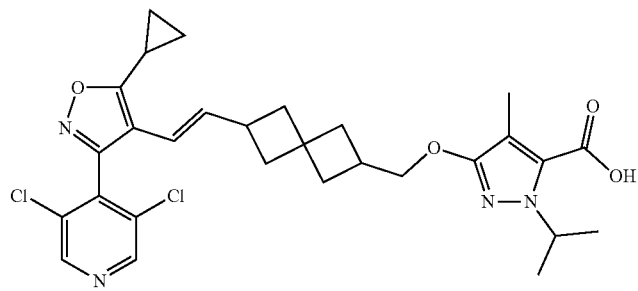<br>(E)-3-((6-(2-(5-cyclopropyl-3-(3,5-dichloropyridin-4-yl)isoxazol-4-yl)vinyl)spiro[3.3]heptan-2-yl)methoxy)-1-isopropyl-4-methyl-1H-pyrazole-5-carboxylic acid | Ex. 29 |
| 60 | 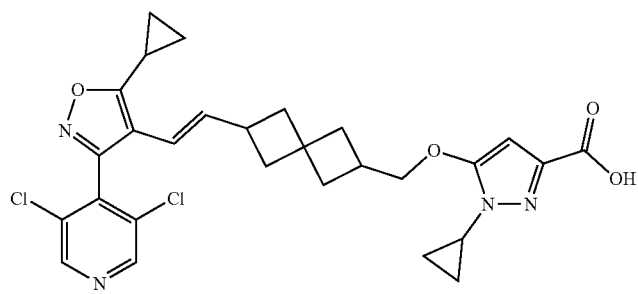<br>(E)-1-cyclopropyl-5-((6-(2-(5-cyclopropyl-3-(3,5-dichloropyridin-4-yl)isoxazol-4-yl)vinyl)spiro[3.3]heptan-2-yl)methoxy)-1H-pyrazole-3-carboxylic acid | Ex. 29 |
| 61 | 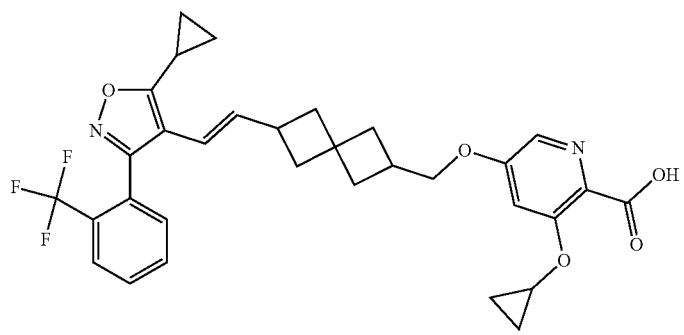<br>(E)-3-cyclopropoxy-5-((6-(2-(5-cyclopropyl-3-(2-(trifluoromethyl)phenyl)isoxazol-4-yl)vinyl)spiro[3.3]heptan-2-yl)methoxy)picolinic acid | Ex. 32 |
| 62 | 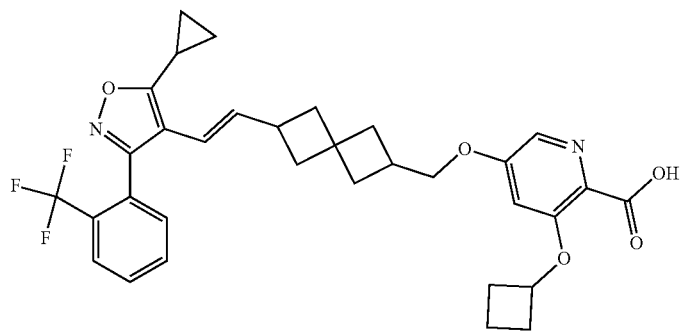<br>(E)-3-cyclobutoxy-5-((6-(2-(5-cyclopropyl-3-(2-(trifluoromethyl)phenyl)isoxazol-4-yl)vinyl)spiro[3.3]heptan-2-yl)methoxy)picolinic acid | Ex. 32 |

-continued

| Ex. No. | Structure | Method |
|---|---|---|
| 63 | 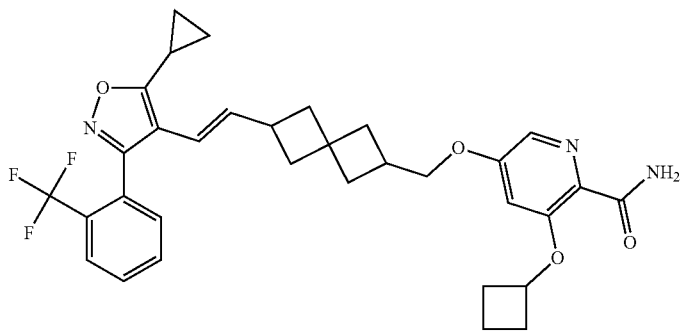<br>(E)-3-cyclobutoxy-5-((6-(2-(5-cyclopropyl-3-(2-(trifluoromethyl)phenyl)isoxazol-4-yl)vinyl)spiro[3.3]heptan-2-yl)methoxy)picolinamide | Ex. 33 |
| 64 | 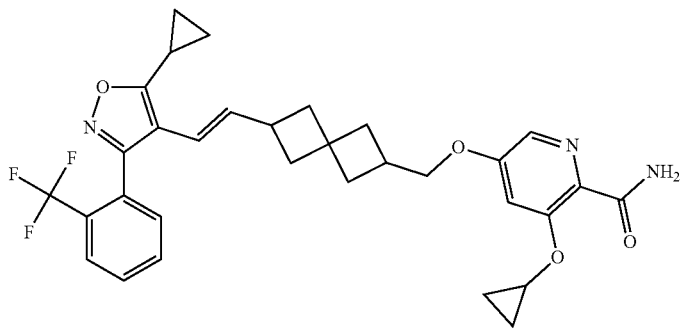<br>(E)-3-cyclopropoxy-5-((6-(2-(5-cyclopropyl-3-(2-(trifluoromethyl)phenyl)isoxazol-4-yl)vinyl)spiro[3.3]heptan-2-yl)methoxy)picolinamide | Ex. 33 |
| 65 | 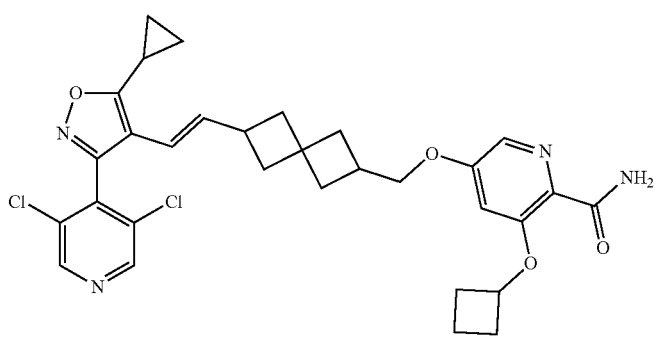<br>(E)-3-cyclobutoxy-5-((6-(2-(5-cyclopropyl-3-(3,5-dichloropyridin-4-yl)isoxazol-4-yl)vinyl)spiro[3.3]heptan-2-yl)methoxy)picolinamide | Ex. 33 |

| Ex. No. | Structure | Method |
|---|---|---|
| 66 | 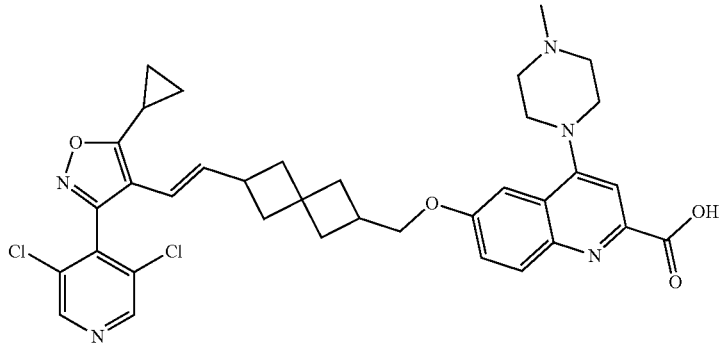<br>(E)-6-((6-(2-(5-cyclopropyl-3-(3,5-dichloropyridin-4-yl)isoxazol-4-yl)vinyl)spiro[3.3]heptan-2-yl)methoxy)-4-(4-methylpiperazin-1-yl)quinoline-2-carboxylic acid | Ex. 29 |
| 67 | 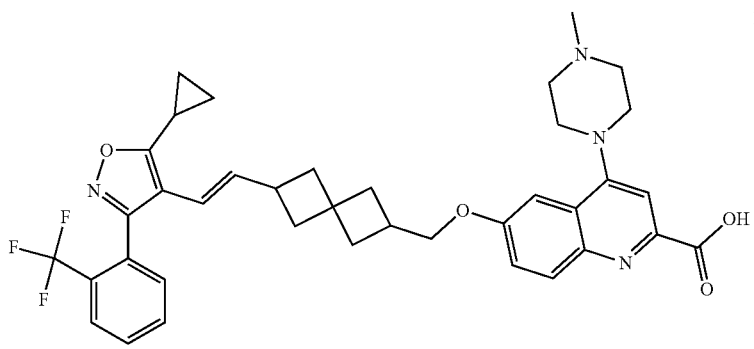<br>(E)-6-((6-(2-(5-cyclopropyl-3-(2-(trifluoromethyl)phenyl)isoxazol-4-yl)vinyl)spiro[3.3]heptan-2-yl)methoxy)-4-(4-methylpiperazin-1-yl)quinoline-2-carboxylic acid | Ex. 29 |

34  MS (ESI) m/z: 602.2 (M + H)⁺; ¹H NMR (400 MHz, CD$_3$OD) δ 8.77 (s, 2H), 8.01 (d, J = 9.24 Hz, 1H), 7.97-7.99 (m, 1H), 7.17 (dd, J = 2.42, 9.24 Hz, 1H), 6.76 (d, J = 2.42 Hz, 1H), 6.13 (dd, J = 1.32, 16.07 Hz, 1H), 5.62 (dd, J = 7.37, 15.96 Hz, 1H), 4.26 (br s, 1H), 4.03 (s, 2H), 3.82 (s, 2H), 2.91 (s, 1H), 2.40-2.49 (m, 2H), 2.24-2.33 (m, 1H), 1.94-2.05 (m, 2H), 1.16-1.25 (m, 4H), 1.04-1.10 (m, 2H), 0.96-1.04 (m, 2H)

35  MS (ESI) m/z: 580.3 (M + H)⁺; ¹H NMR (500 MHz, CD$_3$OD) δ 8.78-8.89 (m, 1H), 8.10 (br s, 1H), 7.93 (br d, J = 7.43 Hz, 1H), 7.72-7.81 (m, 1H), 7.50 (br s, 1H), 7.22 (br s, 1H), 6.85 (br s, 1H), 6.21 (br d, J = 15.96 Hz, 1H), 5.81 (br dd, J = 7.98, 15.96 Hz, 1H), 4.27 (br s, 2H), 3.75 (br s, 2H), 2.70 (br s, 2H), 2.39 (br s, 2H), 2.16-2.32 (m, 1H), 2.01 (br d, J = 9.90 Hz, 1H), 1.19 (br s, 4H)

36  MS (ESI) m/z: 578.2 (M + H)⁺; ¹H NMR (500 MHz, CD$_3$OD) δ 8.76 (s, 2H), 8.29 (br d, J = 8.80 Hz, 1H), 7.94 (s, 1H), 7.15 (d, J = 9.63 Hz, 1H), 6.13 (d, J = 15.41 Hz, 1H), 5.62 (dd, J = 7.15, 15.96 Hz, 1H), 4.46 (s, 2H), 4.26 (br s, 2H), 4.23-4.25 (m, 3H), 2.93 (br d, J = 7.98 Hz, 1H), 2.45-2.52 (m, 2H), 2.25-2.34 (m, 1H), 2.02-2.11 (m, 2H), 1.20-1.24 (m, 2H), 1.17 (br dd, J = 1.93, 4.95 Hz, 2H)

37  MS (ESI) m/z: 577.2 (M + H)⁺; ¹H NMR (400 MHz, CD$_3$OD) δ 8.96-9.06 (m, 1H), 8.72 (s, 1H), 8.10 (br d, J = 9.24 Hz, 1H), 7.93 (d, J = 5.28 Hz, 1H), 7.70 (s, 1H), 7.26 (br d, J = 2.20, 9.24 Hz, 1H), 6.85 (d, J = 2.20 Hz, 1H), 6.07 (dd, J = 1.10, 16.07 Hz, 1H), 5.62 (dd, J = 7.15, 16.18 Hz, 1H), 4.32 (s, 3H), 4.08 (s, 2H), 3.86 (s, 2H), 2.91 (br d, J = 8.14 Hz, 1H), 2.43 (ddd, J = 2.42, 8.03, 10.23 Hz, 2H), 2.17-2.33 (m, 1H), 1.94-2.09 (m, 2H), 1.14-1.23 (m, 4H)

38  MS (ESI) m/z: 635.2 (M + H)⁺; ¹H NMR (500 MHz, CD$_3$OD) δ 8.77 (s, 2H), 8.13 (d, J = 9.35 Hz, 1H), 7.49 (s, 1H), 7.31 (dd, J = 2.48, 9.35 Hz, 1H), 6.88 (d, J = 2.48 Hz, 1H), 6.14 (dd, J = 1.24, 16.09 Hz, 1H), 5.61 (dd, J = 7.43, 15.96 Hz, 1H), 5.52 (br dd, J = 3.85, 7.15 Hz, 1H), 5.32-5.48 (m, 1H), 4.11 (s, 2H), 3.89 (s, 2H), 2.79-3.01 (m, 5H), 2.42-2.51 (m, 2H), 2.23-2.33 (m, 1H), 1.97-2.06 (m, 2H), 1.19-1.25 (m, 2H), 1.15-1.19 (m, 2H)

39  MS (ESI) m/z: 603.1 (M + H)⁺; ¹H NMR (500 MHz, CD$_3$OD) δ 8.77 (s, 2H), 8.13 (br d, J = 9.35 Hz, 1H), 8.04 (s, 1H), 7.28 (br d, J = 8.25 Hz, 1H), 6.78-6.82 (m, 1H), 6.13 (dd, J = 1.10, 16.23 Hz, 1H), 5.62 (dd, J = 7.43, 15.96 Hz, 1H), 4.39 (br s, 1H), 4.07 (s, 2H), 3.85 (s, 2H), 2.88-2.96 (m, 1H), 2.41-2.49 (m, 2H), 2.24-2.31 (m, 1H), 1.95-2.04 (m, 2H), 1.21 (td, J = 2.85, 8.32 Hz, 2H), 1.14-1.18 (m, 2H), 1.10 (br d, J = 5.23 Hz, 2H), 1.04 (br s, 2H)

-continued

| Ex. No. | Structure | Method |
|---|---|---|

40. MS (ESI) m/z: 635.2 (M + H)+; 1H NMR (500 MHz, CD3OD) δ 8.77 (s, 2H), 8.14 (br s, 1H), 7.53 (br s, 1H), 7.22-7.36 (m, 1H), 6.90 (br s, 1H), 6.09-6.18 (m, 1H), 5.63 (br d, J = 7.15 Hz, 1H), 5.03 (br dd, J = 6.19, 12.52 Hz, 1H), 4.93-4.99 (m, 2H), 4.11 (br s, 2H), 3.89 (br s, 2H), 2.86-3.00 (m, 1H), 2.55-2.71 (m, 2H), 2.38-2.55 (m, 3H), 2.24-2.33 (m, 1H), 1.96-2.08 (m, 2H), 1.15-1.25 (m, 4H)

41. MS (ESI) m/z: 595.2 (M + H)+; 1H NMR (500 MHz, CD3OD) δ 8.77 (s, 2H), 7.59 (s, 1H), 6.81-6.91 (m, 1H), 6.66 (d, J = 1.93 Hz, 1H), 6.12 (dd, J = 1.24, 16.09 Hz, 1H), 5.57-5.68 (m, 1H), 4.16 (s, 3H), 4.03 (s, 2H), 3.81 (s, 2H), 2.92 (br d, J = 7.98 Hz, 1H), 2.38-2.48 (m, 2H), 2.29 (s, 1H), 1.96-2.05 (m, 2H), 1.20-1.24 (m, 2H), 1.18 (dd, J = 2.20, 5.23 Hz, 2H)

42. MS (ESI) m/z: 526.2 (M + H)+; 1H NMR (400 MHz, CD3OD) δ 8.76 (s, 2H), 6.95 (dd, J = 1.32, 2.42 Hz, 1H), 6.71-6.79 (m, 1H), 6.21 (t, J = 2.20 Hz, 1H), 6.10 (dd, J = 1.32, 16.07 Hz, 1H), 5.63 (s, 1H), 3.87 (s, 2H), 3.80 (s, 3H), 3.67 (s, 2H), 2.85-2.95 (m, 1H), 2.36-2.45 (m, 2H), 2.22-2.32 (m, 1H), 1.90-1.99 (m, 2H), 1.13-1.24 (m, 4H)

43. MS (ESI) m/z: 584.1 (M + H)+; 1H NMR (500 MHz, CDCl3) δ 8.67 (s, 2H), 7.89 (d, J = 9.08 Hz, 1H), 7.30 (s, 1H), 6.97 (dd, J = 2.61, 9.22 Hz, 1H), 6.69 (d, J = 2.48 Hz, 1H), 5.99 (dd, J = 1.10, 15.96 Hz, 1H), 5.60 (dd, J = 7.02, 16.09 Hz, 1H), 4.04 (s, 2H), 3.91-4.01 (m, 1H), 3.85 (s, 2H), 2.90 (q, J = 8.07 Hz, 1H), 2.36-2.50 (m, 2H), 2.13 (tt, J = 4.99, 8.36 Hz, 1H), 1.97-2.04 (m, 2H), 1.27-1.29 (m, 2H), 1.25-1.30 (m, 2H), 1.17-1.20 (m, 2H), 0.93-1.00 (m, 4H)

44. MS (ESI) m/z: 603.2 (M + H)+; 1H NMR (500 MHz, CD3OD) δ 9.00 (d, J = 5.2 Hz, 1H), 8.73 (s, 1H), 8.12 (br d, J = 8.5 Hz, 1H), 8.03 (s, 1H), 7.93 (d, J = 5.2 Hz, 1H), 7.28 (br d, J = 8.5 Hz, 1H), 6.78 (d, J = 2.2 Hz, 1H), 6.06 (dd, J = 16.0, 1.1 Hz, 1H), 5.62 (dd, J = 16.1, 7.3 Hz, 1H), 4.39 (br s, 1H), 4.08 (s, 2H), 3.86 (s, 2H), 2.95-2.86 (m, 1H), 2.42 (ddd, J = 10.2, 8.0, 2.2 Hz, 2H), 2.30-2.22 (m, 1H), 2.05-1.97 (m, 2H), 1.20 (td, J = 5.5, 2.8 Hz, 2H), 1.17 (br d, J = 1.9 Hz, 2H), 1.10 (br d, J = 5.8 Hz, 2H), 1.04 (br s, 2H)

45. MS (ESI) m/z: 529.1 [M + H]+; EC50 = 24; 1H NMR (500 MHz, DMSO-d6) δ = 8.84 (d, J = 2.4 Hz, 2H), 6.10-6.00 (m, 2H), 5.54 (dd, J = 7.4, 16.1 Hz, 1H), 4.00 (d, J = 6.6 Hz, 2H), 2.83-2.70 (m, 1H), 2.58 (s, 3H), 2.39-2.27 (m, 1H), 2.24-2.01 (m, 4H), 1.96-1.80 (m, 2H), 1.74-1.59 (m, 3H), 1.23-1.14 (m, 2H), 1.12-1.03 (m, 2H).

46. MS (ESI) m/z: 644.0 [M + H]+; EC50 = 22; 1H NMR (500 MHz, DMSO-d6) δ = 8.83 (d, J = 4.3 Hz, 2H), 8.31 (s, 1H), 8.24 (brd, J = 9.3 Hz, 1H), 7.67 (brdd, J = 2.2, 9.3 Hz, 1H), 7.32 (brs, 1H), 6.04 (d, J = 16.1 Hz, 1H), 5.55 (dd, J = 7.3, 16.1 Hz, 1H), 4.11 (br d, J = 6.5 Hz, 2H), 2.86-2.76 (m, 1H), 2.67-2.58 (m, 1H), 2.40-2.29 (m, 1H), 2.26-2.05 (m, 3H), 2.01-1.88 (m, 2H), 1.83-1.60 (m, 3H), 1.21-1.14 (m, 2H), 1.12-1.02 (m, 2H)

47. MS (ESI) m/z: 525.1 [M + H]+; EC50 = 40; 1H NMR (500 MHz, DMSO-d6) δ = 8.86 (d, J = 2.4 Hz, 2H), 7.49 (brd, J = 7.6 Hz, 1H), 7.42-7.32 (m, 2H), 7.11 (brd, J = 7.3 Hz, 1H), 6.06 (brd, J = 15.9 Hz, 1H), 5.51 (dd, J = 7.5, 16.0 Hz, 1H), 3.90 (brd, J = 6.4 Hz, 2H), 2.84-2.74 (m, 1H), 2.57-2.47 (m, 1H), 2.40-2.30 (m, 1H), 2.24-2.03 (m, 3H), 1.96-1.79 (m, 2H), 1.75-1.60 (m, 3H), 1.22-1.13 (m, 2H), 1.12-1.02 (m, 2H).

48. MS (ESI) m/z: 523.1 [M + H]+; EC50 = 214; 1H NMR (500 MHz, DMSO-d6) δ = 8.03-7.85 (m, 2H), 7.84-7.68 (m, 2H), 7.52-7.39 (m, 2H), 7.38-7.26 (m, 3H), 7.03 (br d, J = 7.3 Hz, 1H), 5.94 (br d, J = 15.9 Hz, 1H), 5.43 (br dd, J = 7.6, 16.2 Hz, 1H), 3.88 (br d, J = 6.1 Hz, 2H), 2.75-2.60 (m, 1H), 2.56-2.42 (m, 1H), 2.33-2.21 (m, 1H), 2.18-1.99 (m, 3H), 1.94-1.74 (m, 2H), 1.71-1.51 (m, 3H), 1.18-1.09 (m, 2H), 1.06-0.97 (m, 2H).

49. MS (ESI) m/z: 537.2 [M + H]+; EC50 = 178; 1H NMR (500 MHz, DMSO-d6) δ = 7.92 (br d, J = 7.6 Hz, 1H), 7.83-7.72 (m, 2H), 7.48 (br d, J = 7.3 Hz, 1H), 7.38 (br s, 1H), 7.13 (br d, J = 7.9 Hz, 2H), 6.80 (br d, J = 8.2 Hz, 3H), 5.95 (br d, J = 16.2 Hz, 1H), 5.43 (br dd, J = 7.6, 16.2 Hz, 1H), 3.80 (br d, J = 6.7 Hz, 2H), 3.26 (s, 2H), 2.75-2.67 (m, 1H), 2.49-2.41 (m, 1H), 2.33-2.24 (m, 1H), 2.17-1.97 (m, 3H), 1.91-1.73 (m, 2H), 1.65-1.52 (m, 3H), 1.19-1.09 (m, 2H), 1.08-1.00 (m, 2H)

50. MS (ESI) m/z: 539.5 [M + H]+; EC50 = 142; 1H NMR (500 MHz, DMSO-d6) δ = 8.08 (br s, 1H), 7.92 (br d, J = 7.6 Hz, 1H), 7.84-7.69 (m, 2H), 7.48 (br d, J = 7.3 Hz, 1H), 7.28 (br s, 1H), 5.95 (br d, J = 16.2 Hz, 1H), 5.43 (br dd, J = 7.3, 16.2 Hz, 1H), 3.97 (br d, J = 6.4 Hz, 2H), 2.75-2.65 (m, 1H), 2.55-2.42 (m, 4H), 2.33-2.20 (m, 1H), 2.18-1.97 (m, 3H), 1.94-1.75 (m, 2H), 1.69-1.47 (m, 3H), 1.19-1.11 (m, 2H), 1.07-1.00 (m, 2H).

51. MS (ESI) m/z: 528.1 [M + H]+; EC50 = 99; 1H NMR (500 MHz, DMSO-d6) δ = 7.92 (br d, J = 7.6 Hz, 1H), 7.84-7.66 (m, 2H), 7.48 (br d, J = 7.6 Hz, 1H), 6.05 (s, 1H), 5.95 (br d, J = 16.2 Hz, 1H), 5.43 (br dd, J = 7.5, 16.0 Hz, 1H), 3.98 (br d, J = 6.4 Hz, 2H), 2.75-2.65 (m, 1H), 2.57-2.45 (m, 4H), 2.34-2.22 (m, 1H), 2.18-1.96 (m, 3H), 1.92-1.75 (m, 2H), 1.71-1.47 (m, 3H), 1.19-1.12 (m, 2H), 1.07-1.00 (m, 2H).

52. MS (ESI) m/z: 643.1 [M + H]+; EC50 = 82; 1H NMR (500 MHz, DMSO-d6) δ = 8.31 (s, 1H), 8.24 (br d, J = 9.5 Hz, 1H), 7.91 (br d, J = 7.6 Hz, 1H), 7.84-7.72 (m, 2H), 7.66 (br d, J = 8.9 Hz, 1H), 7.49 (br d, J = 7.3 Hz, 1H), 7.28 (br s, 1H), 5.95 (br d, J = 16.2 Hz, 1H), 5.45 (br dd, J = 7.3, 15.9 Hz, 1H), 4.08 (br d, J = 6.4 Hz, 2H), 2.78-2.67 (m, 1H), 2.62-2.45 (m, 1H), 2.33-2.24 (m, 1H), 2.21-2.12 (m, 2H), 2.09-2.01 (m, 1H), 1.95-1.85 (m, 2H), 1.78-1.54 (m, 3H), 1.18-1.09 (m, 2H), 1.10-1.00 (m, 2H).

| Ex. No. | Structure | Method |
|---|---|---|
| 53 | MS (ESI) m/z: 575.2 [M + H]$^+$; EC$_{50}$ = 187: $^1$H NMR (500 MHz, DMSO-d$_6$) δ = 8.31 (br d, J = 8.5 Hz, 1H), 8.08-7.99 (m, 2H), 7.92 (br d, J = 7.6 Hz, 1H), 7.85-7.69 (m, 2H), 7.49 (br d, J = 7.3 Hz, 1H), 7.43 (br d, J = 9.2 Hz, 1H), 7.39 (br s, 1H), 5.96 (br d, J = 15.9 Hz, 1H), 5.45 (br dd, J = 7.3, 16.2 Hz, 1H), 4.02 (br d, J = 6.7 Hz, 2H), 2.82-2.68 (m, 1H), 2.63-2.52 (m, 1H), 2.36-2.23 (m, 1H), 2.22-2.11 (m, 2H), 2.10-1.99 (m, 1H), 1.96-1.80 (m, 2H), 1.74-1.53 (m, 3H), 1.17-1.11 (m, 2H), 1.10-1.00 (m, 2H). | |
| 54 | MS (ESI) m/z: 576.1 [M + H]$^+$; EC$_{50}$ = 122; $^1$H NMR (500 MHz, DMSO-d$_6$) δ = 8.65-8.49 (m, 1H), 8.12-8.03 (m, 1H), 7.92 (s, 1H), 7.83-7.68 (m, 3H), 7.50 (br d, J = 7.9 Hz, 2H), 5.96 (br d, J = 16.2 Hz, 1H), 5.46 (br dd, J = 7.6, 15.9 Hz, 1H), 4.15 (br d, J = 6.1 Hz, 2H), 2.80-2.70 (m, 1H), 2.67-2.56 (m, 1H), 2.35-2.25 (m, 1H), 2.22-2.12 (m, 2H), 2.15-2.04 (m, 1H), 2.00-1.85 (m, 2H), 1.77-1.53 (m, 3H), 1.20-1.10 (m, 2H), 1.08-0.98 (m, 2H). | |
| 55 | MS (ESI) m/z: 594.0 [M + H]$^+$; EC$_{50}$ = 50; $^1$H NMR (500 MHz, DMSO-d$_6$) δ = 8.82 (d, J = 2.6 Hz, 2H), 8.41 (br s, 1H), 7.59 (s, 1H), 6.03 (d, J = 16.1 Hz, 1H), 5.54 (dd, J = 7.4, 16.1 Hz, 1H), 4.06 (br d, J = 6.6 Hz, 2H), 2.83-2.69 (m, 1H), 2.60-2.45 (m, 1H), 2.35-2.25 (m, 1H), 2.24-2.03 (m, 3H), 1.96-1.78 (m, 2H), 1.75-1.56 (m, 3H), 1.25-1.15 (m, 2H), 1.12-1.01 (m, 2H). | |
| 56 | MS (ESI) m/z: 593.2 [M + H]$^+$; EC$_{50}$ = 95; $^1$H NMR (500 MHz, DMSO-d$_6$) δ = 8.39 (br s, 1H), 7.89 (br d, J = 7.7 Hz, 1H), 7.83-7.70 (m, 2H), 7.57 (s, 1H), 7.45 (br d, J = 7.4 Hz, 1H), 5.91 (d, J = 16.2 Hz, 1H), 5.48 (dd, J = 7.4, 16.2 Hz, 1H), 4.04 (br d, J = 6.6 Hz, 2H), 2.76-2.67 (m, 1H), 2.61-2.50 (m, 1H), 2.28-2.20 (m, 1H), 2.20-2.01 (m, 3H), 1.94-1.79 (m, 2H), 1.72-1.54 (m, 3H), 1.18-1.10 (m, 2H), 1.06-0.98 (m, 2H). | |
| 57 | MS (ESI) m/z: 576.9 [M + H]$^+$; EC$_{50}$ = 75; $^1$H NMR (500 MHz, DMSO-d$_6$) δ = 8.86 (d, J = 3.7 Hz, 2H), 8.73-8.63 (m, 1H), 8.13 (d, J = 9.2 Hz, 1H), 7.82 (br s, 1H), 7.55 (dd, J = 2.1, 8.9 Hz, 1H), 6.07 (d, J = 16.2 Hz, 1H), 5.51 (dd, J = 7.5, 16.0 Hz, 1H), 4.17 (br d, J = 5.5 Hz, 2H), 2.90-2.74 (m, 1H), 2.71-2.58 (m, 1H), 2.43-2.31 (m, 1H), 2.27-2.05 (m, 3H), 2.00-1.85 (m, 2H), 1.83-1.59 (m, 3H), 1.22-1.14 (m, 2H), 1.12-1.04 (m, 2H). | |
| 58 | MS (ESI) m/z: 596.0 [M + H]$^+$; EC$_{50}$ = 22; $^1$H NMR (500 MHz, DMSO-d$_6$) δ = 8.86 (br d, J = 3.4 Hz, 2H), 7.82 (br s, 1H), 7.22 (br s, 1H), 6.06 (br d, J = 16.2 Hz, 1H), 5.50 (br dd, J = 7.5, 16.0 Hz, 1H), 4.80 (br t, J = 6.9 Hz, 1H), 3.99 (br d, J = 6.4 Hz, 2H), 2.79-2.68 (m, 1H), 2.45-2.35 (m, 2H), 2.35-2.25 (m, 1H), 2.22-1.98 (m, 5H), 1.94-1.74 (m, 4H), 1.72-1.52 (m, 4H), 1.19-1.12 (m, 2H), 1.09-1.00 (m, 2H). | |
| 59 | MS (ESI) m/z: 570.9 [M + H]$^+$; EC$_{50}$ = 85; $^1$H NMR (500 MHz, DMSO-d$_6$) δ = 8.83 (d, J = 2.3 Hz, 2H), 6.02 (d, J = 16.1 Hz, 1H), 5.54 (dd, J = 7.4, 16.1 Hz, 1H), 5.38-5.20 (m, 1H), 4.02 (d, J = 6.6 Hz, 2H), 2.84-2.75 (m, 1H), 2.59-2.44 (m, 1H), 2.36-2.25 (m, 1H), 2.23-2.04 (m, 3H), 1.98 (s, 3H), 1.91 (s, 2H), 1.73-1.58 (m, 3H), 1.29 (d, J = 6.5 Hz, 6H), 1.22-1.14 (m, 2H), 1.11-1.03 (m, 2H). | |
| 60 | MS (ESI) m/z: 555.1 [M + H]$^+$; EC$_{50}$ = 34; $^1$H NMR (500 MHz, DMSO-d$_6$) δ = 8.83 (s, 2H), 6.03 (d, J = 16.1 Hz, 1H), 5.93 (s, 1H), 5.54 (dd, J = 7.3, 16.2 Hz, 1H), 3.99 (d, J = 6.5 Hz, 2H), 3.45-3.36 (m, 1H), 2.83-2.76 (m, 1H), 2.58-2.50 (m, 1H), 2.36-2.28 (m, 1H), 2.24-2.04 (m, 3H), 1.95-1.82 (m, 2H), 1.77-1.59 (m, 3H), 1.21-1.13 (m, 2H), 1.13-1.07 (m, 2H), 1.04-0.97 (m, 2H), 0.96-0.89 (m, 2H). | |
| 61 | MS (ESI) m/z: 581.2 [M + H]$^+$; EC$_{50}$ = 16; $^1$H NMR (500 MHz, DMSO-d$_6$) δ = 7.98-7.89 (m, 1H), 7.85-7.54 (m, 3H), 7.49 (br d, J = 7.3 Hz, 1H), 7.26 (br s, 1H), 5.95 (br d, J = 16.2 Hz, 1H), 5.44 (br dd, J = 7.3, 16.2 Hz, 1H), 4.00 (br d, J = 6.4 Hz, 2H), 3.97-3.90 (m, 1H), 2.76-2.68 (m, 1H), 2.57-2.43 (m, 1H), 2.34-2.25 (m, 1H), 2.21-1.99 (m, 3H), 1.94-1.75 (m, 2H), 1.72-1.51 (m, 3H), 1.18-1.10 (m, 2H), 1.08-1.00 (m, 2H), 0.84-0.75 (m, 2H), 0.70-0.60 (m, 2H). | |
| 62 | MS (ESI) m/z: 595.2 [M + H]$^+$; EC$_{50}$ = 36; $^1$H NMR (500 MHz, DMSO-d$_6$) δ = 7.99-7.88 (m, 1H), 7.86-7.71 (m, 3H), 7.50 (br d, J = 7.3 Hz, 1H), 6.84 (br s, 1H), 5.95 (br d, J = 16.2 Hz, 1H), 5.45 (br dd, J = 7.5, 16.0 Hz, 1H), 4.86-4.74 (m, 1H), 3.99 (br d, J = 6.4 Hz, 2H), 2.78-2.66 (m, 1H), 2.45-2.35 (m, 2H), 2.32-2.22 (m, 1H), 2.19-1.98 (m, 5H), 1.94-1.73 (m, 4H), 1.71-1.50 (m, 4H), 1.20-1.10 (m, 2H), 1.09-1.10 (m, 2H). | |
| 63 | MS (ESI) m/z: 594.2 [M + H]$^+$; EC$_{50}$ = 393; $^1$H NMR (500 MHz, DMSO-d$_6$) δ = 7.99-7.87 (m, 1H), 7.85-7.67 (m, 3H), 7.56-7.42 (m, 2H), 7.35-7.09 (m, 1H), 6.82 (s, 1H), 5.95 (br d, J = 15.9 Hz, 1H), 5.44 (br dd, J = 7.5, 16.0 Hz, 1H), 4.79 (br t, J = 7.2 Hz, 1H), 3.98 (br d, J = 6.4 Hz, 2H), 2.79-2.68 (m, 1H), 2.45-2.35 (m, 2H), 2.35-2.25 (m, 1H), 2.22-1.98 (m, 5H), 1.94-1.74 (m, 4H), 1.72-1.52 (m, 4H), 1.19-1.12 (m, 2H), 1.09-1.00 (m, 2H). | |
| 64 | MS (ESI) m/z: 580.2 [M + H]$^+$; EC$_{50}$ = 667; $^1$H NMR (500 MHz, DMSO-d$_6$) δ = 7.95-7.89 (m, 1H), 7.86 (br s, 1H), 7.83-7.72 (m, 2H), 7.52-7.44 (m, 2H), 7.30 (br s, 1H), 7.19 (br s, 1H), 5.96 (br d, J = 16.2 Hz, 1H), 5.45 (br dd, J = 7.5, 16.0 Hz, 1H), 4.02 (br d, J = 6.7 Hz, 2H), 3.99-3.93 (m, 1H), 2.79-2.69 (m, 1H), 2.58-2.44 (m, 1H), 2.34-2.24 (m, 1H), 2.21-2.10 (m, 2H), 2.08-1.97 (m, 1H), 1.93-1.79 (m, 2H), 1.72-1.54 (m, 3H), 1.19-1.11 (m, 2H), 1.08-1.00 (m, 2H), 0.85-0.76 (m, 2H), 0.73-0.65 (m, 2H). | |
| 65 | MS (ESI) m/z: 595.1 [M + H]$^+$; EC$_{50}$ = 153; $^1$H NMR (500 MHz, DMSO-d$_6$) δ = 8.86 (br d, J = 3.4 Hz, 2H), 7.82 (br s, 1H), 7.55 (s, 1H), 7.22 (s, 1H), 6.83 (br s, 1H), 6.06 (br d, J = 16.2 Hz, 1H), 5.50 (br dd, J = 7.5, 16.0 Hz, 1H), 4.80 (br t, J = 6.9 Hz, 1H), 3.99 (br d, J = 6.4 Hz, 2H), 2.85-2.72 (m, 1H), 2.60-2.46 (m, 1H), | |

| Ex. No. | Structure | Method |
|---|---|---|
| | 2.45-2.31 (m, 3H), 2.22-2.00 (m, 5H), 1.96-1.74 (m, 3H), 1.72-1.54 (m, 4H), 1.21-1.14 (m, 2H), 1.12-1.04 (m, 2H). | |
| 66 | MS (ESI) m/z: 674.1.1 [M + H]$^+$; EC$_{50}$ = 188; $^1$H NMR (500 MHz, DMSO-d$_6$) δ = 8.86 (br d, J = 4.3 Hz, 2H), 8.05 (br d, J = 9.2 Hz, 1H), 7.58 (s, 1H), 7.47 (br d, J = 9.2 Hz, 1H), 7.21 (br s, 1H), 6.07 (br d, J = 15.9 Hz, 1H), 5.51 (br dd, J = 7.6, 16.2 Hz, 1H), 4.07 (br d, J = 6.1 Hz, 2H), 2.93-2.69 (m, 9H), 2.66-2.55 (m, 1H), 2.5 (s, 3H), 2.40-2.30 (m, 1H), 2.25-2.05 (m, 3H), 2.00-1.84 (m, 2H), 1.80-1.58 (m, 3H), 1.21-1.13 (m, 2H), 1.10-1.03 (m, 2H). | |
| 67 | MS (ESI) m/z: 673.3 [M + H]$^+$; EC$_{50}$ = 302; $^1$H NMR (500 MHz, DMSO-d$_6$) δ = 8.05 (br d, J = 9.5 Hz, 1H), 7.94 (br d, J = 12.8 Hz, 1H), 7.85-7.72 (m, 2H), 7.59 (s, 1H), 7.49 (br s, 1H), 7.21 (s, 1H), 7.04-6.98 (m, 1H), 5.97 (br d, J = 15.3 Hz, 1H), 5.48 (br dd, J = 7.6, 16.2 Hz, 1H), 4.08 (br d, J = 6.4 Hz, 2H), 3.20-2.70 (m, 9H), 2.63-2.57 (m, 1H), 2.50 (s, 3H), 2.33-2.28 (m, 1H), 2.23-2.13 (m, 2H), 2.12-2.01 (m, 1H), 1.96-1.85 (m, 2H), 1.79-1.57 (m, 3H), 1.19-1.10 (m, 2H), 1.08-1.00 (m, 2H). | |

Biological Evaluation

The exemplified compounds of the present invention were tested in the transient human FXR/Gal4-luciferase reporter assay, and assay results were reported in Table 1 and Examples 1 to 3 together with other analytical data.

A Gal4-hFXR fusion construct reporter system was used as the primary assay to characterize compound activity. A construct including 5 copies of the Gal4 promoter response element upstream of a firefly luciferase reporter cDNA was stably expressed in HEK293 cells. This reporter cell line was maintained in Dulbecco's Modified Eagle's medium (DMEM; Gibco) supplemented with 1% penicillin-streptomycin (P/S) solution, 500 μg/mL Zeocin and 10% charcoal/dextran-treated fetal bovine serum (cs-FBS) at 37° C. in a humidified 5% $CO_2$ atmosphere. Another plasmid was constructed in which the human cytomegalovirus promoter in the pcDNA3.1 vector directs the expression of the cDNA encoding a fusion protein comprised of the DNA binding domain from the Gal4 transcription factor fused to the ligand binding domain from human FXR.

The day prior to transfection, the reporter cells in culture are detached from the plate with trypsin and plated into a T75 flask at a sufficient density to achieve approximately 90% confluence the next morning. The transfection reagents are prepared by separately diluting 25 μg of the pcDNA3.1-Gal4-FXR plasmid into 1.87 mL of Opti-MEM (Thermo-Fisher), and 40 μL of Lipofectamine 2000 (Thermo-Fisher) into 1.87 mL of Opti-MEM, and then adding the diluted DNA solution into the diluted Lipofectamine 2000 solution and incubating at room temperature for 15-20 minutes. The mixture is further diluted with 10 mL of a solution comprised of DMEM, 10% cs-FBS, and 1% P/S immediately prior to transferring to the cells. The maintenance culture media is aspirated from the cells and the final transfection mixture is added before the cells are incubated overnight at 37° C. in a humidified 5% $CO_2$ atmosphere. This protocol can be scaled up, and the transiently transfected cells can be cryopreserved in an assay-ready format.

For compound testing, 100 nL of the compounds (serial dilutions in DMSO) are dispensed with an Echo acoustic dispenser (Labcyte) into the wells of a Corning/Costar clear bottom 384-well white plate. The transfected cells are harvested, counted, and diluted such that 10-25,000 cells in 25 μL are plated into each well of the 384-well compound assay plate. The compound-treated cells are incubated overnight at 37° C. in a humidified 5% $CO_2$ atmosphere. The next morning 25 μL of Steady-Glo (Promega) are added to each well of the plate, the mixture is incubated for 15 min. with shaking, and luminescence is measured on an Envision (Perkin Elmer) plate reader. Background counts from cells treated with DMSO alone are subtracted from all raw counts, and the corrected values are converted to a percentage of the control response attained with 8 μM GW-4064. These data are fit to a 4-parameter log agonist-response equation to calculate an EC50 value.

In Vivo Testing Example: Acute Mouse PK/PD

Male, C57BL6/NTac mice, weighing 25-28 g, are purchased from Taconic Labs (Hudson, N.Y.) and maintained on Teklad Global 18% Protein Rodent Diet (Harlan Laboratories). After 1 week acclimation, mice are sorted into groups based upon body weight. Mice are administered a single oral dose of vehicle or experimental compound. Systemic compound exposure is evaluated in plasma derived from blood collected via the submandibular vein at 1 hour post-dose, and at study termination (6 h). At study termination, the animals are euthanized and rapidly dissected. The medial lobe of the liver is divided, with one half being homogenized and analyzed for compound exposure, and the other half saved in RNAlater (Thermo-Fisher Scientific). The ileum is also dissected and preserved in RNAlater. Tissue samples in RNAlater are homogenized with MP Biomedicals' beads. RNA is extracted using the MagMax-96 Total RNA Isolation kit (Thermo-Fisher Scientific) according to the manufacturer's protocol. RNA Concentration is determined with the Nano-Drop 8000 Spectrophotometer (Thermo Fisher). Reverse transcription is done with Invitrogen's SuperScript® VILO cDNA Synthesis Kit according to the manufacturer's protocol. Real time PCR is done with Applied Biosystems' Taqman PCR master mixture according to the manufacturer's protocol. All primers are purchased from Thermo-Fisher Scientific. Mouse genes analyzed include Nr0b2 (which encodes the small heterodimer partner, SHP), Abcb11 (which encodes the bile salt excretion pump, BSEP), Cyp7a1, & Cyp8b1 in liver, and Fgf15, Fabp6 (which encodes ileal bile acid binding protein, I-BABP), Slc51a (which encodes organic solute transporter alpha subunit, OSTA), and Slc51b (which encodes organic solute transporter beta subunit, OSTB) in the ileum. The statistical significant changes in FGF15 gene expression are expressed as fold increase and $CYP_{7A1}$ expression as a percent reduction relative to vehicle control.

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

What is claimed is:

1. A compound of Formula (I):

or a stereoisomer, a tautomer, or a pharmaceutically acceptable salt or solvate thereof; wherein
$X^1$ is C;
$X^2$ is N;
$X^3$ is O;
$X^4$ is C
Y is $CR^7$, or N;
m and n are each independently an integer of 0, 1, or 2;
h and g are each independently an integer of 1 or 2;
d and f are each independently an integer of 0, 1, 2, or 3;
Z is 6- to 10-membered aryl, 5- to 10-membered heteroaryl, 3- to 10-membered carbocyclyl, or 4- to 10-membered heterocyclyl, wherein the aryl, heteroaryl carbocyclyl, and heterocyclyl are independently substituted with 0 to 5 $R^8$;
$L^1$ is a covalent bond, O, S, $NR^{17}$, $—S(O)_2$, $C_{1-3}$ alkylene, $C_{1-3}$ heteroalkylene, $C_{2-4}$ alkenylene, $C_{2-4}$ alkynylene, aryl, or a 5- to 6-membered heteroaryl containing 1 to 4 heteroatoms independently selected from N, O, and S; wherein the alkylene, heteroalkylene, aryl, and heteroaryl are each independently substituted with 0 to 3 $R^{11}$;
$L^2$ is a covalent bond, O, S, $NR^{18}$, $C_{1-3}$ alkylene, or $C_{1-3}$ heteroalkylene, wherein the alkylene and heteroalkylene are independently substituted with 0 to 3 $R^{16}$;
$R^X$ is $-L^3-R^Z$;
$L^3$ is a covalent bond, $C_{1-3}$ alkylene, or $—C(O)NR^{12}—CH_2-$, wherein the $C_{1-3}$ alkylene is substituted with 0 to 3 $R^{15}$;
$R^Z$ is $—CN$, $—C(O)OR^{13}$, $—C(O)NR^{14a}R^{14b}$, $R^e$ is $C_{1-6}$ alkyl, $C_{3-6}$ cycloalkyl, haloalkyl, hydroxyalkyl, aminoalkyl, alkoxyalkyl, or haloalkoxyalkyl;
$R^{Y1}$ and $R^{Y2}$ are each independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy; or alternatively two $R^{Y1}$, together with the carbon atoms to which they are attached, form a bridge moiety; and with the proviso that when Y is N and $R^{Y1}$ is attached to a carbon atom adjacent to Y, then $R^{Y1}$ is not halo, cyano, hydroxyl, amino, alkoxy, or haloalkoxy;
$R^1$ is $C_{1-6}$ alkyl, $C_{3-5}$ cycloalkyl, or C4-6 heterocyclyl, wherein the alkyl and cycloalkyl are independently substituted with 0 to 3 $R^9$;
$R^2$ is 6- to 10-membered aryl, 5- to 10-membered heteroaryl, 3- to 10-membered carbocyclyl, or 4- to 10-membered heterocyclyl, wherein the aryl, heteroaryl, carbocyclyl, and heterocyclyl are independently substituted with 0 to 5 $R^{10}$;
$R^3$ and $R^4$ are each independently hydrogen, $C_{1-6}$ alkyl, haloalkyl, hydroxyalkyl, aminoalkyl, alkoxyalkyl, or haloalkoxyalkyl;
$R^5$ and $R^7$ are each independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy;
$R^6$, $R^{17}$ and $R^{18}$ are each independently hydrogen, $C_{1-6}$ alkyl, haloalkyl, hydroxyalkyl, aminoalkyl, alkoxyalkyl, haloalkoxyalkyl, alkoxy, or haloalkoxy;
$R^8$ and $R^{10}$ are each independently halo, cyano, hydroxyl, amino, oxo, $—OR^a$, $—SR^a$, =S, $—NR^cR^c$, =NH, =N—OH, =$NR^a$, =N—$OR^a$, $—NO_2$, $—S(O)_2R^a$, $—S(O)_2NHR^b$, $—S(O)_2NR^cR^c$, $—S(O)_2OR^b$, $—OS(O)_2R^b$, $—OS(O)_2OR^b$, $—P(O)(OR^b)(OR^b)$, $—C(O)R^b$, $—C(NR^b)R^b$, $—C(O)OR^b$, $—C(O)NR^cR^c$, $—C(NR^b)NR^cR^c$, $—OC(O)R^b$, $—NR^bC(O)R^b$, $—OC$ (O)OR$^b$, —NR$^b$C(O)OR$^b$, —OC(O)NR$^c$R$^c$, —NR$^b$C(O)NR$^c$R$^c$, —NR$^b$C(NR$^b$)R$^b$, —NR$^b$C(NR$^b$)NR$^c$ N$^c$, C$_{1-6}$ alkyl, C$_{1-6}$ haloalkyl, aryl, arylalkyl, heteroaryl, carbocyclyl, or heterocyclyl; wherein the alkyl, aryl, heteroaryl, carbocyclyl, and heterocyclyl, by themselves or as part of another group, are each independently substituted with 0 to 5 R$^d$;

R$^a$ is each independently C$_{1-6}$ alkyl, haloalkyl, hydroxyalkyl, aminoalkyl, alkoxyalkyl, haloalkoxyalkyl, aryl, arylalkyl, heteroaryl, heteroarylalkyl, carbocyclyl, carbocyclylalkyl, heterocyclyl, or heterocyclylalkyl;

R$^b$ is each independently hydrogen or R$^a$;

R$^c$ is each independently R$^b$ or alternatively, the two R$^c$ are taken together with the nitrogen atom to which they are bonded form a 4-, 5-, 6- or 7-membered heterocyclyl;

R$^d$ is each independently R$^a$, alkoxy, haloalkoxy, alkylamino, cycloalkylamino, heterocyclylamino, haloalkyl, hydroxyalkyl, aminoalkyl, cycloalkoxy, heterocyclyloxy, haloalkoxy, alkoxyalkoxy, haloalkylamino, alkoxyalkylamino, haloalkoxyalkylamino, arylamino, aralkylamino, aryloxy, aralkyloxy, heteroaryloxy, heteroarylalkyloxy, alkylthio, halo, cyano, hydroxyl, amino, oxo, —OR$^a$, —SR$^a$, =S, —NR$^c$R$^c$, =NH, =N—OH, =NR$^a$, =N—OR$^a$, —NO$_2$, —S(O)$_2$R$^a$, —S(O)$_2$NHR$^b$, —S(O)$_2$NR$^c$R$^c$, —S(O)$_2$OR$^b$, —OS(O)$_2$OR$^b$, —OS(O)$_2$OR$^b$, —P(O)(OR$^b$)(OR$^b$), —C(O)R$^b$, —C(NR$^b$)R$^b$, —C(O)OR$^b$, —C(O)NR$^c$R$^c$, —C(NR$^b$)NR$^c$R$^c$, —OC(O)R$^b$, —NR$^b$C(O)R$^b$, —OC(O)OR$^b$, —NR$^b$C(O)OR$^b$, —NR$^b$C(O)NR$^c$R$^c$, —NR$^b$C(NR$^b$)R$^b$, or NR$^b$(NR$^b$)NR$^c$R$^c$;

R$^9$ is each independently halo, cyano, hydroxyl, amino, or C$_{1-6}$ alkyl;

R$^{11}$ and R$^{16}$ are each independently halo, oxo, cyano, hydroxyl, amino, C$_{1-6}$ alkyl, C$_{3-6}$ cycloalkyl, C$_{4-6}$ heterocyclyl, alkylamino, haloalkyl, hydroxyalkyl, aminoalkyl, alkoxyalkyl, haloalkoxyalkyl, alkoxy, or haloalkoxy;

R$^{12}$ are each independently hydrogen or C$_{1-4}$ alkyl; and

R$^{13}$ is hydrogen, C$_{1-10}$ alkyl, or glycosyl;

R$^{14a}$ and R$^{14b}$ are each independently hydrogen, C$_{1-6}$ alkyl, C$_{3-6}$ cycloalkyl, C$_{4-6}$ heterocyclyl, alkylamino, haloalkyl, hydroxyalkyl, aminoalkyl, alkoxyalkyl, haloalkoxyalkyl, alkoxy, or haloalkoxy; and R$^{15}$ are each independently halo, oxo, cyano, hydroxyl, amino, alkyl, alkoxy, or alkylamino; or alternatively, two R$^{15}$, taken together with the atom(s) to which they are attached, form a carbocyclyl or heterocyclyl moiety.

2. The compound of claim 1, wherein the

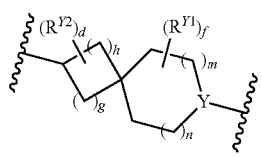

moiety is:

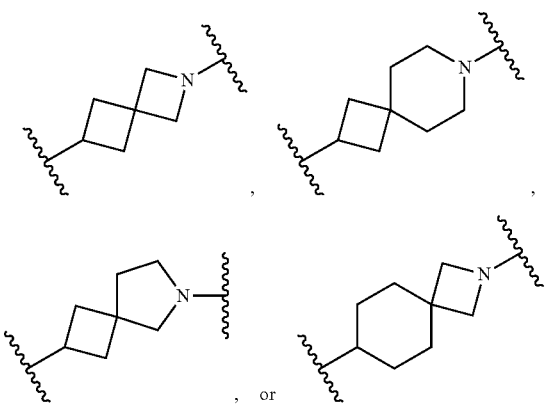

3. The compound of claim 1, wherein Z is phenyl or 5- to 10-membered heteroaryl, wherein the phenyl and heteroaryl are independently substituted with 0 to 5 R$^8$.

4. The compound of claim 1, wherein:

L$^1$ is a covalent bond; and

—Z—R$^x$ is selected from:

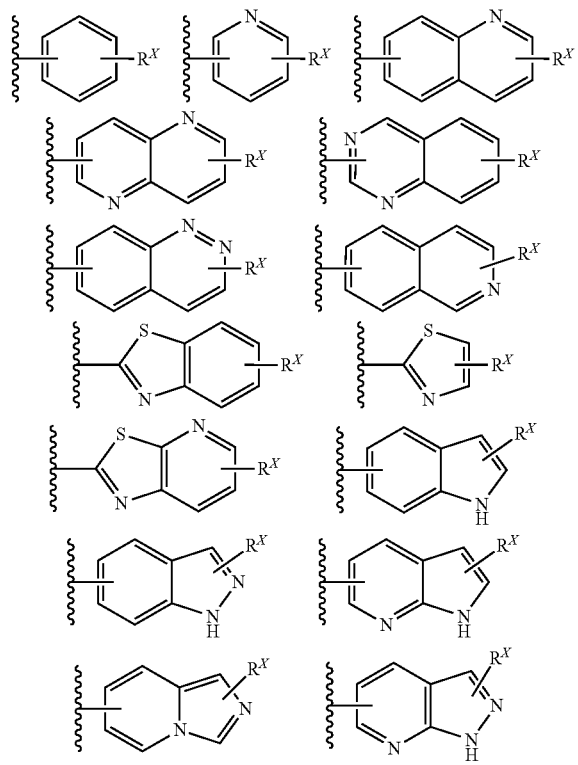

wherein the Z moiety is further substituted with 0 to 3 R$^8$.

5. The compound of claim 1, wherein:

L$^2$ is a covalent bond; and

R$^2$ is phenyl or 6-membered heteroaryl, wherein the phenyl and heteroaryl are independently substituted with 0 to 5 R$^{10}$.

6. The compound of claim 1, which is represented by Formula (II):

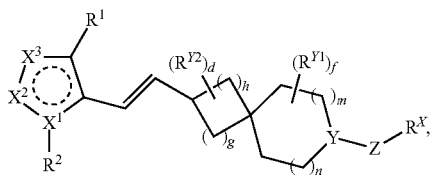
(II)

Z is phenyl or a 5- to 10-membered heteroaryl, wherein the phenyl and heteroaryl are independently substituted with 0 to 3 $R^8$;
$R^X$ is —C(O)$OR^{13}$;
each $R^Y$ is independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy;
f is an integer of 0, 1, or 2;
$R^1$ is $C_{1-6}$ alkyl or $C_{3-5}$ cycloalkyl, wherein the alkyl and cycloalkyl are independently substituted with 0 to 3 $R^9$;
$R^2$ is phenyl or 6-membered heteroaryl, wherein the phenyl and heteroaryl are independently substituted with 0 to 3 $R^{10}$.

7. The compound according to claim 1, wherein:

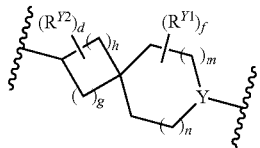

moiety is

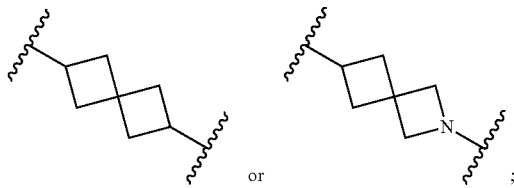 [SMILES: *C1CC2(C1)CC(*)C2 ; *C1CC2(C1)CN(*)C2]

$L^1$ is a covalent bond or —CH$_2$O—;
Z is phenyl, pyrazolyl, pyridinyl, benzo[d]thiazolyl, thiazolo[5,4-b]pyridinyl, quinolinyl, isoquinolinyl, cinnolinyl, or naphthyridinyl, each substituted with 0 to 2 $R^8$;
$R^x$ is —CN, —C(O)OH, —CH$_2$C(O)OH, or —C(O)NH$_2$;
$R^1$ is cyclopropyl;
$L^2$ is a covalent bond;
$R^2$ is phenyl or pyridinyl, each substituted with 1 or 2 $R^{10}$;
$R^3$ is hydrogen;
$R^4$ is hydrogen;
$R^8$ is each independently F, —CH$_3$, —CH$_2$CH$_3$, —CH(CH$_3$)$_2$, —CF$_3$, —CH$_2$OCH$_3$, —OCH$_3$, —OCD$_3$, —OCH$_2$CH$_3$, —OCH(CH$_3$)$_2$, cyclopropyl, methylpiperazinyl, —O(cyclopropyl), —O(cyclobutyl), —O(fluorocyclobutyl), —O(oxetanyl), or —O(tetrahydrofuranyl); and
$R^{10}$ is each independently Cl or —CF$_3$.

8. The compound of claim 1 or a pharmaceutically acceptable salt thereof;
(E)-6-(6-(2-(5-Cyclopropyl-3-(3,5-dichloropyridin-4-yl)isoxazol-4-yl)vinyl)-2-azaspiro[3.3]heptan-2-yl)-4-methoxyquinoline-2-carboxylic acid (1);
(E)-6-(6-(2-(3-(3-chloropyridin-4-yl)-5-cyclopropylisoxazol-4-yl)vinyl)-2-azaspiro[3.3]heptan-2-yl)-4-methoxyquinoline-2-carboxylic acid (2);
(E)-4-Cyclobutoxy-6-(6-(2-(5-cyclopropyl-3-(2-(trifluoromethyl)pyridin-3-yl)isoxazol-4-yl) vinyl)-2-azaspiro[3.3]heptan-2-yl)quinoline-2-carboxylic acid (3);
(E)-6-(6-(2-(5-cyclopropyl-3-(2,6-dichlorophenyl)isoxazol-4-yl)vinyl)-2-azaspiro[3.3]heptan-2-yl)-4-(trifluoromethyl)quinoline-2-carboxylic acid (4);
(E)-4-(6-(2-(5-cyclopropyl-3-(2,6-dichlorophenyl)isoxazol-4-yl)vinyl)-2-azaspiro[3.3]heptan-2-yl)benzoic acid (5);
(E)-6-(6-(2-(3-(3-chloropyridin-4-yl)-5-cyclopropylisoxazol-4-yl)vinyl)-2-azaspiro[3.3]heptan-2-yl)-4-(trifluoromethyl)quinoline-2-carboxylic acid (6);
(E)-6-(6-(2-(5-cyclopropyl-3-(3,5-dichloropyridin-4-yl)isoxazol-4-yl)vinyl)-2-azaspiro[3.3]heptan-2-yl)-4-(trifluoromethyl)quinoline-2-carboxylic acid (7);
(E)-6-(6-(2-(5-cyclopropyl-3-(2-(trifluoromethyl)phenyl)isoxazol-4-yl)vinyl)-2-azaspiro[3.3]heptan-2-yl)-4-(trifluoromethyl)quinoline-2-carboxylic acid (8);
(E)-2-(6-(2-(5-cyclopropyl-3-(2-(trifluoromethyl)phenyl)isoxazol-4-yl)vinyl)-2-azaspiro[3.3]heptan-2-yl)-7-methylthiazolo[5,4-b]pyridine-5-carboxylic acid (9);
(E)-2-(6-(2-(5-cyclopropyl-3-(3,5-dichloropyridin-4-yl)isoxazol-4-yl)vinyl)-2-azaspiro[3.3]heptan-2-yl)-4-fluorobenzo[d]thiazole-6-carboxylic acid (10);
(E)-6-(6-(2-(5-cyclopropyl-3-(3,5-dichloropyridin-4-yl)isoxazol-4-yl)vinyl)-2-azaspiro[3.3]heptan-2-yl)-4-isopropoxyquinoline-2-carboxylic acid (11);
(E)-6-(6-(2-(5-cyclopropyl-3-(2-(trifluoromethyl)phenyl)isoxazol-4-yl)vinyl)-2-azaspiro[3.3]heptan-2-yl)-4-isopropoxyquinoline-2-carboxylic acid (12);
(E)-7-(6-(2-(5-cyclopropyl-3-(3,5-dichloropyridin-4-yl)isoxazol-4-yl)vinyl)-2-azaspiro[3.3]heptan-2-yl)-1-methylisoquinoline-3-carboxylic acid (13);
(E)-7-(6-(2-(5-cyclopropyl-3-(3,5-dichloropyridin-4-yl)isoxazol-4-yl)vinyl)-2-azaspiro[3.3]heptan-2-yl)-1-ethylisoquinoline-3-carboxylic acid (14);
(E)-6-(6-(2-(5-cyclopropyl-3-(3-(trifluoromethyl)pyridin-2-yl)isoxazol-4-yl)vinyl)-2-azaspiro[3.3]heptan-2-yl)-4-isopropoxyquinoline-2-carboxylic acid (15);
(E)-6-(6-(2-(5-cyclopropyl-3-(2-(trifluoromethyl)phenyl)isoxazol-4-yl)vinyl)-2-azaspiro[3.3]heptan-2-yl)-4-methoxyquinoline-2-carboxylic acid (16);
(E)-4-cyclobutoxy-6-(6-(2-(5-cyclopropyl-3-(3,5-dichloropyridin-4-yl)isoxazol-4-yl)vinyl)-2-azaspiro[3.3]heptan-2-yl)quinoline-2-carboxylic acid (17);
(E)-6-(6-(2-(5-cyclopropyl-3-(2-(trifluoromethyl)phenyl)isoxazol-4-yl)vinyl)-2-azaspiro[3.3]heptan-2-yl)-4-(oxetan-3-yloxy)quinoline-2-carboxylic acid (18);
(E)-7-(6-(2-(5-cyclopropyl-3-(2-(trifluoromethyl)phenyl)isoxazol-4-yl)vinyl)-2-azaspiro[3.3]heptan-2-yl)-1-methoxyisoquinoline-3-carboxylic acid (19);
(R,E)-6-(6-(2-(5-cyclopropyl-3-(2-(trifluoromethyl)phenyl)isoxazol-4-yl)vinyl)-2-azaspiro[3.3]heptan-2-yl)-4-((tetrahydrofuran-3-yl)oxy)quinoline-2-carboxylic acid (20);
(S,E)-6-(6-(2-(5-cyclopropyl-3-(2-(trifluoromethyl)phenyl)isoxazol-4-yl)vinyl)-2-azaspiro[3.3]heptan-2-yl)-4-((tetrahydrofuran-3-yl)oxy)quinoline-2-carboxylic acid (21);

(E)-6-(6-(2-(5-cyclopropyl-3-(2-(trifluoromethyl)pyridin-3-yl)isoxazol-4-yl) vinyl)-2-azaspiro[3.3]heptan-2-yl)-4-methoxyquinoline-2-carboxylic acid (22);

(E)-6-(6-(2-(5-cyclopropyl-3-(2-(trifluoromethyl)pyridin-3-yl)isoxazol-4-yl) vinyl)-2-azaspiro[3.3]heptan-2-yl)-4-(oxetan-3-yloxy)quinoline-2-carboxylic acid (23);

(E)-6-(6-(2-(5-cyclopropyl-3-(3,5-dichloropyridin-4-yl)isoxazol-4-yl)vinyl)-2-azaspiro[3.3]heptan-2-yl)-4-(oxetan-3-yloxy)quinoline-2-carboxylic acid (24);

(E)-6-(6-(2-(5-cyclopropyl-3-(2-(trifluoromethyl)pyridin-3-yl)isoxazol-4-yl)vinyl)-2-azaspiro[3.3]heptan-2-yl)-4-ethoxyquinoline-2-carboxylic acid (25);

(R,E)-6-(6-(2-(5-cyclopropyl-3-(2-(trifluoromethyl)pyridin-3-yl)isoxazol-4-yl) vinyl)-2-azaspiro[3.3]heptan-2-yl)-4-((tetrahydrofuran-3-yl)oxy)quinoline-2-carboxylic acid (26);

(E)-6-(6-(2-(5-cyclopropyl-3-(3,5-dichloropyridin-4-yl)isoxazol-4-yl)vinyl)-2-azaspiro[3.3]heptan-2-yl)-4-(methoxymethyl)quinoline-2-carboxylic acid (27);

(E)-6-(6-(2-(5-cyclopropyl-3-(3,5-dichloropyridin-4-yl)isoxazol-4-yl)vinyl)-2-azaspiro[3.3]heptan-2-yl)-4-methoxy-1,5-naphthyridine-2-carboxylic acid (28);

(E)-546-(2-(5-Cyclopropyl-3-(3,5-dichloropyridin-4-yl)isoxazol-4-yl)vinyl)spiro[3,3] heptan-2-yl)methoxy)-3-methylpicolinic acid (29);

(E)-5-((6-(2-(5-Cyclopropyl-3-(2-(trifluoromethyl)phenyl)isoxazol-4-yl)vinyl)spiro[3.3]heptan-2-yl)methoxy)-3-methylpicolinic acid (30-31);

(E)-5-((6-(2-(5-Cyclopropyl-3-(2-(trifluoromethyl)phenyl)isoxazol-4-yl)vinyl)spiro[3,3] heptan-2-yl)methoxy)-3-isopropoxypicolinic acid (32);

(E)-5-((6-(2-(5-Cyclopropyl-3-(2-(trifluoromethyl)phenyl)isoxazol-4-yl)vinyl)spiro[3,3] heptan-2-yl)methoxy)-3-isopropoxypicolinamide (33);

(E)-4-cyclopropoxy-6-(6-(2-(5-cyclopropyl-3-(3,5-dichloropyridin-4-yl)isoxazol-4-yl)vinyl)-2-azaspiro[3.3]heptan-2-yl)quinoline-2-carboxamide (34);

(E)-6-(6-(2-(5-cyclopropyl-3-(3,5-dichloropyridin-4-yl)isoxazol-4-yl) vinyl)-2-azaspiro[3.3]heptan-2-yl)-4-(methoxy-d3)quinoline-2-carboxylic acid (35);

(E)-6-(6-(2-(5-cyclopropyl-3-(3,5-dichloropyridin-4-yl) vinyl)-2-azaspiro[3.3]heptan-2-yl)-4-methoxy-1,5-naphthyridine-2-carboxylic acid (36);

(E)-6-(6-(2-(5-cyclopropyl-3-(4-(trifluoromethyl)pyridin-3-yl) isoxazol-4-yl)vinyl)-2-azaspiro[3.3]heptan-2-yl)-4-methoxyquinoline-2-carboxylic acid (37);

6-(64(E)-2-(5-cyclopropyl-3-(3,5-dichloropyridin-4-yl)isoxazol-4-yl)vinyl)-2-azaspiro[3.3]heptan-2-yl)-4-((lr,30-3-fluorocyclobutoxy)quinoline-2-carboxylic acid (38);

(E)-4-cyclopropoxy-6-(6-(2-(5-cyclopropyl-3-(3,5-dichloropyridin-4-yl)isoxazol-4-yl)vinyl)-2-azaspiro[3.3]heptan-2-yl)quinoline-2-carboxylic acid (39);

6-(64(E)-2-(5-cyclopropyl-3-(3,5-dichloropyridin-4-yl)isoxazol-4-yl)vinyl)-2-azaspiro[3.3]heptan-2-yl)-4-((1s,3s)-3-fluorocyclobutoxy)quinoline-2-carboxylic acid (40);

(E)-6-(6-(2-(5-cyclopropyl-3-(3,5-dichloropyridin-4-yl)isoxazol-4-yl)vinyl)-2-azaspiro[3.3]heptan-2-yl)-8-fluoro-4-methoxyquinoline-2-carboxylic acid (41);

(E)-3-(6-(2-(5-cyclopropyl-3-(3,5-dichloropyridin-4-yl)isoxazol-4-yl)vinyl)-2-azaspiro[3.3]heptan-2-yl)-5-methoxybenzoic acid (42);

(E)-4-cyclopropoxy-6-(6-(2-(5-cyclopropyl-3-(3,5-dichloropyridin-4-yl)isoxazol-4-yl)vinyl)-2-azaspiro[3.3]heptan-2-yl)quinoline-2-carbonitrile (43);

(E)-4-cyclopropoxy-6-(6-(2-(5-cyclopropyl-3-(4-(trifluoromethyl)pyridin-3-yl)isoxazol-4-yl) vinyl)-2-azaspiro[3.3]heptan-2-yl)quinoline-2-carboxylic acid (44);

(E)-5-((6-(2-(5-cyclopropyl-3-(3,5-dichloropyridin-4-yl)isoxazol-4-yl)vinyl) spiro[3.3]heptan-2-yl)methoxy)-1-methyl-1H-pyrazole-3-carboxylic acid (45);

(E)-6-((6-(2-(5-cyclopropyl-3-(3,5-dichloropyridin-4-yl)isoxazol-4-yl)vinyl) spiro[3.3]heptan-2-yl)methoxy)-4-(trifluoromethyl) quinoline-2-carboxylic acid (46);

(E)-3-((6-(2-(5-cyclopropyl-3-(3,5-dichloropyridin-4-yl)isoxazol-4-yl)vinyl) spiro[3.3]heptan-2-yl)methoxy) benzoic acid (47);

(E)-3-((6-(2-(5-cyclopropyl-3-(2-(trifluoromethyl)phenyl)isoxazol-4-yl)vinyl) spiro[3.3]heptan-2-yl)methoxy)benzamide (48);

(E)-2-(4-((6-(2-(5-cyclopropyl-3-(2-(trifluoromethyl) phenyl) isoxazol-4-yl)vinyl) spiro[3.3]heptan-2-yl)methoxy)phenyl)acetamide (49);

(E)-5-((6-(2-(5-cyclopropyl-3-(2-(trifluoromethyl)phenyl)isoxazol-4-yl)vinyl) spiro[3.3]heptan-2-yl)methoxy)-3-methylpicolinic acid (50);

(E)-5-((6-(2-(5-cyclopropyl-3-(2-(trifluoromethyl)phenyl)isoxazol-4-yl)vinyl) spiro[3.3]heptan-2-yl)methoxy)-1-methyl-1H-pyrazole-3-carboxylic acid (51);

(E)-6-((6-(2-(5-cyclopropyl-3-(2-(trifluoromethyl)phenyl)isoxazol-4-yl)vinyl) spiro[3.3]heptan-2-yl)methoxy)-4-(trifluoromethyl)quinoline-2-carboxylic acid (52);

(E)-6-((6-(2-(5-cyclopropyl-3-(2-(trifluoromethyl)phenyl)isoxazol-4-yl)vinyl) spiro[3.3]heptan-2-yl)methoxy)quinoline-2-carboxylic acid (53);

(E)-7-((6-(2-(5-cyclopropyl-3-(2-(trifluoromethyl)phenyl)isoxazol-4-yl)vinyl) spiro[3.3]heptan-2-yl)methoxy)cinnoline-3-carboxylic acid (54);

(E)-54(6-(2-(5-cyclopropyl-3-(3,5-dichloropyridin-4-yl)isoxazol-4-yl) vinyl) spiro[3.3]heptan-2-yl)methoxy)-3-(trifluoromethyl)picolinic acid (55);

(E)-5-((6-(2-(5-cyclopropyl-3-(2-(trifluoromethyl)phenyl)isoxazol-4-yl)vinyl) spiro[3.3]heptan-2-yl)methoxy)-3-(trifluoromethyl)picolinic acid (56);

(E)-7-((6-(2-(5-cyclopropyl-3-(3,5-dichloropyridin-4-yl)isoxazol-4-yl)vinyl) spiro[3.3]heptan-2-yl)methoxy) cinnoline-3-carboxylic acid (57);

(E)-3-cyclobutoxy-5-((6-(2-(5-cyclopropyl-3-(3,5-dichloropyridin-4-yl)isoxazol-4-yl)vinyl) spiro[3.3]heptan-2-yl)methoxy)picolinic acid (58);

(E)-34(6-(2-(5-cyclopropyl-3-(3,5-dichloropyridin-4-yl) isoxazol-4-yl) vinyl) spiro[3.3]heptan-2-yl)methoxy)-1-isopropyl-4-methyl-1H-pyrazole-5-carboxylic acid (59);

(E)-1-cyclopropyl-5-((6-(2-(5-cyclopropyl-3-(3,5-dichloropyri din-4-yl) isoxazol-4-yl) vinyl)spiro[3.3]heptan-2-yl)methoxy)-1H-pyrazole-3-carboxylic acid (60);

(E)-3-cyclopropoxy-5-((6-(2-(5-cyclopropyl-3-(2-(trifluoromethyl) phenyl)isoxazol-4-yl) vinyl)spiro[3.3] heptan-2-yl)methoxy)picolinic acid (61);

(E)-3-cyclobutoxy-5-((6-(2-(5-cyclopropyl-3-(2-(trifluoromethyl) phenyl)isoxazol-4-yl) vinyl)spiro[3.3]heptan-2-yl)methoxy)picolinic acid (62);

(E)-3-cyclobutoxy-5-((6-(2-(5-cyclopropyl-3-(2-(trifluoromethyl) phenyl)isoxazol-4-yl) vinyl)spiro[3.3]heptan-2-yl)methoxy) picolinamide (63);

(E)-3-cyclopropoxy-5-((6-(2-(5-cyclopropyl-3-(2-(trifluoromethyl) phenyl)isoxazol-4-yl) vinyl)spiro[3.3]heptan-2-yl)methoxy) picolinamide (64);

(E)-3-cyclobutoxy-5-((6-(2-(5-cyclopropyl-3-(3,5-dichloropyridin-4-yl)isoxazol-4-yl) vinyl)spiro[3.3]heptan-2-yl)methoxy)picolinamide (65);

(E)-6-((6-(2-(5-cyclopropyl-3-(3,5-dichloropyridin-4-yl)isoxazol-4-yl)vinyl) spiro[3.3]heptan-2-yl)methoxy)-4-(4-methylpiperazin-1-yl) quinoline-2-carboxylic acid (66); or E)-6-((6-(2-(5-cyclopropyl-3-(2-(trifluoromethyl)phenyl)isoxazol-4-yl)vinyl) spiro[3.3]heptan-2-yl)methoxy)-4-(4-methylpiperazin-1-yl) quinoline-2-carboxylic acid (67).

9. A pharmaceutical composition comprising a pharmaceutically acceptable carrier and a compound according to claim 1, or a pharmaceutically acceptable salt thereof.

10. A method of treating a disease or disorder, comprising administering to a mammalian patient a compound according to claim 1 or a pharmaceutically acceptable salt thereof, wherein said disease or disorder is pathological fibrosis.

11. The method according to claim 10, wherein the pathological fibrosis is liver fibrosis, renal fibrosis, biliary fibrosis, pancreatic fibrosis, nonalcoholic steatohepatitis (NASH), non-alcoholic fatty liver disease (NAFLD), chronic kidney disease, diabetic kidney disease, primary sclerosing cholangitis (PSC), primary biliary cirrhosis (PBC), or idiopathic fibrosis (IPF).

12. A method of treating a disease or disorder, comprising administering to a mammalian patient a compound according to claim 1 or a pharmaceutically acceptable salt thereof, wherein said disease of disorder is nonalcoholic steatohepatitis (NASH), non-alcoholic fatty liver disease (NAFLD), chronic kidney disease, diabetic kidney disease, primary sclerosing cholangitis (PSC), or primary biliary cirrhosis (PBC).

13. A method of treating a disease or disorder, comprising administering to a mammalian patient a compound according to claim 1 or a pharmaceutically acceptable salt thereof, wherein said disease of disorder is idiopathic pulmonary fibrosis (IPF).

* * * * *

UNITED STATES PATENT AND TRADEMARK OFFICE
CERTIFICATE OF CORRECTION

PATENT NO. : 11,286,252 B2
APPLICATION NO. : 16/760810
DATED : March 29, 2022
INVENTOR(S) : Jianxin Feng et al.

Page 1 of 2

It is certified that error appears in the above-identified patent and that said Letters Patent is hereby corrected as shown below:

In the Specification

Column 1, Line 4 (Approx.), delete "CROSS REFERENCE" and insert -- CROSS REFERENCE TO RELATED APPLICATIONS --.

In the Claims

Claim 1, Column 121, Line 30, delete "C:" and insert -- C; --.

Claim 1, Column 121, Line 31, delete "N:" and insert -- N; --.

Claim 1, Column 121, Line 32, delete "O:" and insert -- O; --.

Claim 1, Column 121, Line 33, delete "C" and insert -- C; --.

Claim 1, Column 121, Line 44, delete "—S(O)$_2$," and insert -- —S(O)$_2$—, --.

Claim 1, Column 122, Line 43, delete "C4-6" and insert -- C$_{4-6}$ --.

Claim 1, Column 123, Line 2, delete "—NR$^b$C(NR$^b$)NR$^c$ N$^c$," and insert -- —NR$^b$C(NR$^b$)NR$^c$N$^c$, --.

Claim 1, Column 123, Lines 29-30 (Approx.), delete "—OS(O)$_2$OR$^b$," and insert -- —OS(O)$_2$R$^b$, --.

Claim 1, Column 123, Line 34. delete "NR$^b$(NR$^b$)NR$^c$R$^c$;" and insert -- —NR$^b$C(NR$^b$)NR$^c$R$^c$; --.

Claim 4, Column 124, Line 27 (Approx.), delete "R$^x$" and insert -- R$^X$ --.

Claim 7, Column 125, Line 55 (Approx.), delete "R$^x$" and insert -- R$^X$ --.

Claim 8, Column 127, Line 25, delete "(E)-546" and insert -- (E)-5-((6 --.

Signed and Sealed this
Thirtieth Day of September, 2025

John A. Squires
*Director of the United States Patent and Trademark Office*

CERTIFICATE OF CORRECTION (continued)
U.S. Pat. No. 11,286,252 B2

Claim 8, Column 127, Line 44, delete "(methoxy-d3)" and insert -- (methoxy-$d_3$) --.

Claim 8, Column 127, Line 51, delete "6-(64(E)" and insert -- 6-(6-((E) --.

Claim 8, Column 127, Line 53, delete "((lr,30-" and insert -- ((1r,3r)- --.

Claim 8, Column 127, Line 58, delete "6-(64(E)" and insert -- 6-(6-((E) --.

Claim 8, Column 128, Line 40, delete "(E)-54(6-" and insert -- (E)-5-((6- --.

Claim 8, Column 128, Line 52, delete "(E)-34(6-" and insert -- (E)-3-((6- --.

Claim 8, Column 128, Lines 56-57, delete "(3,5-dichloropyri din-4-yl)" and insert -- (3,5-dichloropyridin-4-yl) --.

Claim 8, Column 129, Line 11, delete "E)" and insert -- (E) --.